United States Patent [19]

Domagala et al.

[11] Patent Number: 5,461,165

[45] Date of Patent: Oct. 24, 1995

[54] INDIVIDUAL STEREOISOMERS OF INTERMEDIATES OF 7-[3-(1-AMINOALKYL)-1-PYRROLIDINYL]-QUINOLONES AND NAPHTHYRIDONES AS ANTIBACTERIAL AGENTS

[75] Inventors: John M. Domagala, Canton; John S. Kiely, Ann Arbor; Mel C. Schroeder, Dexter, all of Mich.

[73] Assignee: Warner-Lambert Company, Morris Plains, N.J.

[21] Appl. No.: 221,146

[22] Filed: Mar. 30, 1994

Related U.S. Application Data

[62] Division of Ser. No. 84,044, Jun. 28, 1993, Pat. No. 5,344,940, which is a division of Ser. No. 966,651, Oct. 26, 1992, Pat. No. 5,258,528, which is a division of Ser. No. 731,825, Jul. 15, 1991, abandoned, which is a continuation-in-part of Ser. No. 621,201, Nov. 30, 1990, abandoned.

[51] Int. Cl.$^6$ .................................................. C07D 207/09
[52] U.S. Cl. ........................... 548/566; 546/123; 546/156
[58] Field of Search ............................................... 548/566

[56] References Cited

U.S. PATENT DOCUMENTS 4,665,079  5/1987  Culbertson et al. ................ 514/312
4,780,468 10/1988  Bridges et al. ..................... 514/312
5,043,450  8/1991  Masuzawa et al. ................. 546/156
5,098,912  3/1992  Hayakawa et al. ................. 514/312

FOREIGN PATENT DOCUMENTS 0207420  1/1987  European Pat. Off. .
0393400 10/1990  European Pat. Off. .
63-166876 7/1988  Japan .
372476  3/1991  Japan .

OTHER PUBLICATIONS

Kimura et al., International Congress of Anti-Microbial Agents and Chemotherapy, Paper No. 1192, Houston, Texas (1989).

*Primary Examiner*—Bernard Dentz
*Attorney, Agent, or Firm*—Ronald A. Daignault; Charles W. Ashbrook

[57] ABSTRACT

Individual stereoisomers of 7-[3-(1-aminoalkyl)-1-pyrrolidinyl]-quinolones and naphthyridones are described, their therapeutic advantages as antibacterial agents, as well as a novel method for the preparation and isolation of such stereoisomers.

4 Claims, No Drawings

INDIVIDUAL STEREOISOMERS OF INTERMEDIATES OF 7-[3-(1-AMINOALKYL)-1-PYRROLIDINYL]-QUINOLONES AND NAPHTHYRIDONES AS ANTIBACTERIAL AGENTS

This is a divisional of U.S. application Ser. No. 08/084,044 filed Jun. 28, 1993, now U.S. Pat. No. 5,344,940, which is a divisional of U.S. application Ser. No. 07/966,651 filed Oct. 26, 1992, now U.S. Pat. No. 5,258,528, which is a divisional of U.S. application Ser. No. 07/731,825 filed Jul. 15, 1991, now abandoned, which is a continuation-in-part of U.S. application Ser. No. 07/621,201 filed Nov. 30, 1990, now abandoned.

BACKGROUND OF THE INVENTION

The identification and selection of an antibacterial chemotherapeutic agent for development depends on several properties. These include in vitro potency against bacteria, in vivo efficacy in animals and man, pharmacokinetic parameters such as good plasma levels and favorable metabolism, and reduced side effects and toxicity. The ideal agent should have the best blend of these properties.

Within the quinolone/naphthyridone class of antibacterials efforts are directed toward increasing in vitro and in vivo efficacy while lowering certain side effects such as phototoxicity and cytotoxicity and reducing general toxicity as well.

It is also known that within the chiral environment of living organisms, individual stereoisomers/enantiomers of drugs may show unique properties relative to the racemic mixtures. When this occurs, the optimal properties of the drug can only be obtained when the most favorable stereoisomer is utilized in its pure chiral form.

U.S. Pat. No. 4,665,079 shows quinolones and naphthyridones by structural formula to have 7-[3-(1-aminoalkyl)-1-pyrrolidinyl]side chains. These compounds of formula A, where $R_1$ or $R_2$

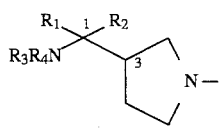

are alkyl or hydrogen were revealed to have good antibacterial in vitro potency. European Patent Publication 207,420 describes such compounds having the two asymmetric centers in the $C_7$ side chain of the quinolone/naphthyridone and the preparation of two diastereomeric mixtures, each containing two nonseparable enantiomers of formula B and C.

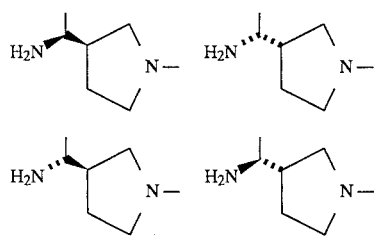

The mixtures B and C were described to possess improved in vivo activity relative to unsubstituted compounds (Formula A, where $R_1$ and $R_2$ are hydrogen). All data reported were for the mixtures, and no method of separation of the mixtures was described. At the International Congress of Antimicrobial Agents and Chemotherapy (ICAAC) in Houston, Tex., 1989, there were reported certain individual enantiomers of 1-ethyl and 1-cyclopropyl-6,8-difluoro-quinolone-3-carboxylic acids. The 3-(R)-1'-(S) stereoisomers were disclosed to have the most potent activity in vitro. One stereoisomer (3R,1'S) was shown to have improved in vivo efficacy relative to an unsubstituted analog. Except for the in vitro data, no other comparisons among the pure stereoisomers were provided. The method employed to prepare and isolate the individual enantiomers involved putting a chiral auxiliary, N-tosylproline, on the amine side chain and performing a separation, removing the N-tosylproline, then replacing it with a conventional protecting group.

It has now been found that overall therapeutic value, i.e. efficacy and safety, of individual enantiomers of various 7-[3-(1-aminoalkyl)-1-pyrrolidinyl]quinolones and naphthyridones cannot be predicted until all of the enantiomers are made, separated, and tested.

It has also been found, further, that the use of a chiral auxiliary, such as (S)- or (R)-α-methyl-benzylamine, as a protecting group, permits separation of diastereomeric amines, thus saving two costly steps in the overall synthesis of all four stereoisomers of 7-[3-(1-aminoalkyl)-1-pyrrolidinyl]quinolones and naphthyridines.

SUMMARY OF THE INVENTION

Accordingly, the present invention includes all four novel enantiomers of the formula I

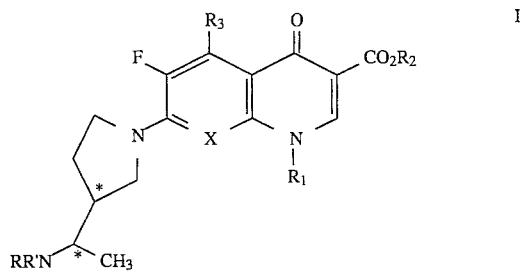

wherein
* denotes an asymmetric carbon atom;
X is C—H, C—F, C—Cl, C—OR, C—$CF_3$ or N;
$R_1$ is ethyl, cyclopropyl, or 2,4-difluorophenyl;
$R_2$ is hydrogen, alkyl of 1–4 carbon atoms or a cation;
$R_3$ is hydrogen, amino, or methyl;
R and R' are each independently hydrogen or alkyl of 1–3 carbon atoms, or a pharmaceutically acceptable acid addition salt thereof; with the proviso that when X is C—F, $R_3$ is amino or $R^1$ is 2,4-difluorophenyl.

The invention also includes a pharmaceutical composition which comprises an antibacterially effective amount of a compound having structural formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

The invention in another aspect includes a process for the preparation of a compound of formula I which comprises reacting a compound of the formula II

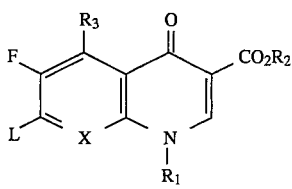

wherein L is fluorine or chlorine or other leaving groups with an individual stereoisomer of the amine of formula III

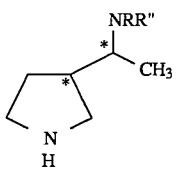

wherein * denotes an asymmetric carbon atom;
R is hydrogen or alkyl of 1–3 carbon atoms; and
R" is hydrogen, alkyl of 1–3 carbon atoms or an amino protecting group which can be removed, if necessary, according to known methods.

The invention in still another aspect includes novel stereoisomers as intermediates which are:
(a) stereoisomers of the formula III

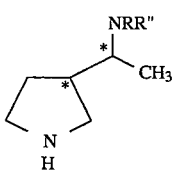

wherein * denotes asymmetric carbon atoms;
R and R" are independently hydrogen or alkyl of 1–3 carbon atoms or an amino protecting group which can be removed by known methods;
(b) stereoisomers of the formula IV

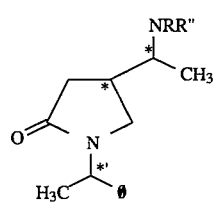

wherein * and *' denote asymmetric carbon atoms;
R is hydrogen or alkyl of 1–3 carbon atoms; and
R" is hydrogen, alkyl of 1–3 carbon atoms, acetyl, trifluoroacetyl or t-butyloxycarbonyl;
(c) stereoisomers of the formula V

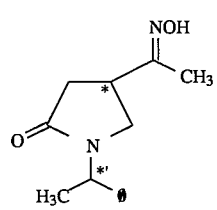

wherein * and *' denote asymmetric carbon atoms.

Finally, the invention includes a process for the preparation of the individual enantiomers of the formula III

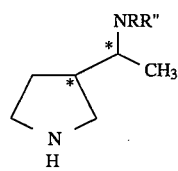

wherein * denotes asymmetric carbon atoms and R and R" are independently hydrogen or alkyl of 1–3 carbon atoms which comprises:

(a) converting a chirally fixed pyrrolidin-5-one-3-carboxylic acid of the formula VI

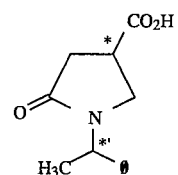

wherein * and *' is either R or S by known methods to a diastereomeric pair of oximes of the formula

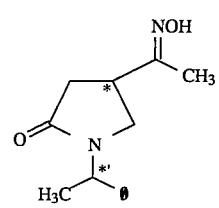

wherein * and *' are asymmetric carbon atoms;
(b) separating the diastereomers by column chromatography;
(c) reducing each diastereomeric oxime by known means to a diastereomeric pair of amines of the formula VIII

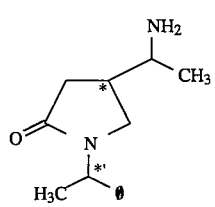

(d) separating each of these diastereomeric pairs into the individual diastereomers by column chromatography;

(e) reducing the 5-pyrrolidinone by known methods and protecting the free amino group with a suitable protecting group (such as BOC, Acetate etc.) by known methods, if desired;

(f) removing the chiral α-methylbenzyl protecting group by hydrogenolysis, thereby liberating the four, separated diastereomers of formulae IIIa–d, and (g) converting, if desired, by known means the resulting compounds of formula VIII or III where R is hydrogen to those where R is independently hydrogen or alkyl of 1–3 carbon atoms. The entire overall process can be summarized in Scheme A.

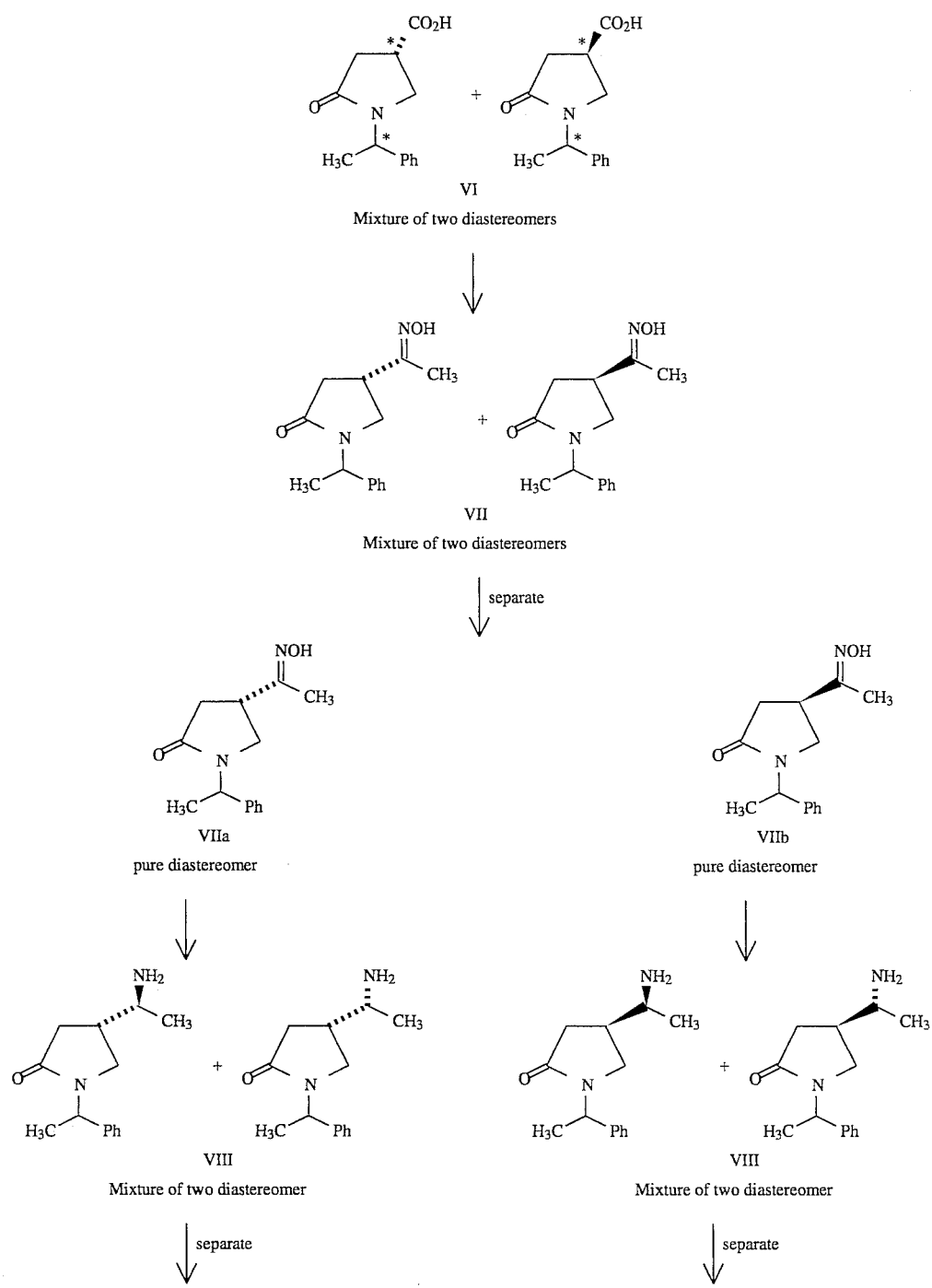
SCHEME A

-continued
SCHEME A

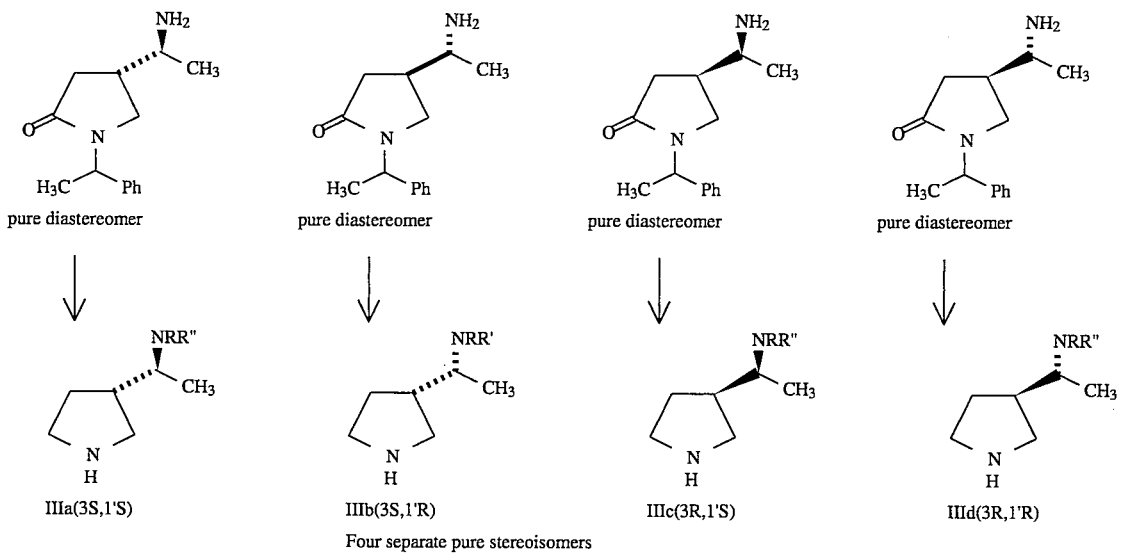

Four separate pure stereoisomers

DETAILED DESCRIPTION AND PREFERRED EMBODIMENTS

The quinolones and naphthyridones of the present invention have 7-[3-(1-aminoalkyl)-1-pyrrolidinyl] as a side chain. This moiety has two asymmetric centers and thus is capable of existing in four stereoisomeric forms. These are illustrated as IIIa–d in Scheme A.

Of the four possible stereoisomers of the quinolones and naphthyridones of the present invention, it has been found that the 3R,1S stereoisomers are generally more potent in vitro, the 3R,1R stereoisomers being second best. However, in vivo efficacy shows the 3R,1S as the generally preferred stereoisomer with the 3S,1R and the 3R,1R alternating for second best. Nevertheless, when considering overall safety and efficacy, i.e. taking potential side effects such as phototoxicity and cytotoxicity into account, the 3S,1R stereoisomers can become overall preferred.

Particularly valuable quinolones and naphthyridones are:

3R,1S-7-[3-(1-aminoethyl)-1-pyrrolidinyl]-1-cyclopropyl-6-fluoro-1,4-dihydro-4-oxo-1,8-naphthyridine-3-carboxylic acid, 3R,1S-7-[3-(1-aminoethyl)-1-pyrrolidinyl]-8-chloro-1-cyclopropyl-6-fluoro-1,4-dihydro-4-oxo-3-quinolinecarboxylic acid, 3R,1S-7-[3-(1-aminoethyl)-1-pyrrolidinyl]-1-cyclopropyl-6-fluoro-1,4-dihydro-4-oxo-3-quinolinecarboxylic acid, 3R,1S-5-amino-7-[3-(1-aminoethyl)-1-pyrrolidinyl]-1-cyclopropyl-6,8-difluoro-1,4-dihydro-4-oxo-3-quinolinecarboxylic acid, 3R,1S-7-[3-(1-aminoethyl)-1-pyrrolidinyl]-1-cyclopropyl-6-fluoro-1,4-dihydro-8-methoxy-4-oxo-3-quinolinecarboxylic acid, 3R,1S-5-amino-7-[3-(1-aminoethyl)-1-pyrrolidinyl]-1-cyclopropyl-6-fluoro-1,4-dihydro-8-methoxy-4-oxo-3-quinolinecarboxylic acid, 3R,1S-7-[3-(1-aminoethyl)-1-pyrrolidinyl]-1-cyclopropyl-6-fluoro-1,4-dihydro-4-oxo-8-trifluoromethyl-3-quinolinecarboxylic acid, 3R,1S-7-[3-(1-aminoethyl)-1-pyrrolidinyl]-1-(2,4-difluorophenyl)-6-fluoro-1,4-dihydro-5-methyl-4-oxo-3-quinolinecarboxylic acid, 3R,1S-7-[3-(1-aminoethyl)-1-pyrrolidinyl]-1-(2,4-difluorophenyl)-6-fluoro-1,4-dihydro-4-oxo-1,8-naphthyridine-3-carboxylic acid, 3R,1S-7-[3-(1-aminoethyl)-1-pyrrolidinyl]-1-(2,4-difluorophenyl)-6-fluoro-1,4-dihydro-4-oxo-3-quinolinecarboxylic acid, 3R,1S-5-amino-7-[3-(1-aminoethyl)-1-pyrrolidinyl]-1-cyclopropyl-6-fluoro-1,4-dihydro-4-oxo-3-quinolinecarboxylic acid, 3R,1S-7-[3-(1-aminoethyl)-1-pyrrolidinyl]-1-cyclopropyl-6-fluoro-1,4-dihydro-5-methyl-4-oxo-3-quinolinecarboxylic acid, 3R,1S-7-[3-(1-aminoethyl)-1-pyrrolidinyl]-1-cyclopropyl-8-ethoxy-6-fluoro-1,4-dihydro-4-oxo-3-quinolinecarboxylic acid, 3R,1S-1-cyclopropyl-6-fluoro-1,4-dihydro-7-[3-[1-(methylamino)ethyl]-1-pyrrolidinyl]-1,8-naphthyridine-3-carboxylic acid, 3R,1S-8-chloro-1-cyclopropyl-6-fluoro-1,4-dihydro-7-[3-[1-(methylamino)ethyl]-1-pyrrolidinyl]-4-oxo-3-quinolinecarboxylic acid, 3R,1S-5-amino-1-cyclopropyl-6,8-difluoro-1,4-dihydro-7-[3-[1-(methylamino)ethyl]-1-pyrrolidinyl]-4-oxo-3-quinolinecarboxylic acid, 3R,1S-1-cyclopropyl-6-fluoro-1,4-dihydro-7-[3-[1-(methylamino)ethyl]-1-pyrrolidinyl]-4-oxo-3-quinolinecarboxylic acid, 3R,1S-1-cyclopropyl-6-fluoro-1,4-dihydro-8-methoxy-7-[3-[1-(methylamino)ethyl]-1-pyrrolidinyl]-4-oxo-3-quinolinecarboxylic acid, 3R,1S-5-amino-1-cyclopropyl-6-fluoro-1,4-dihydro-8-methoxy-7-[3-[1-(methylamino)ethyl]-1-pyrrolidinyl]-4-oxo-3-quinolinecarboxylic acid, 3R,1S-1-cyclopropyl-6-fluoro-1,4-dihydro-7-[3-[1-(methylamino)ethyl]-1-pyrrolidinyl]-4-oxo-8-trifluoromethyl-3-quinolinecarboxylic acid, 3R,1S-1-(2,4-difluorophenyl)-6-fluoro-1,4-dihydro-5-methyl-7-[3-[1-(methylamino)ethyl]-1-pyrrolidinyl]-4-oxo-3-quinolinecarboxylic acid, 3R,1S-1-(2,4-difluorophenyl)-6-fluoro-1,4-dihydro-7-[3-[1-(methylamino)ethyl]-1-pyrrolidinyl]-4-oxo-1,8-naphthyridine-3-carboxylic acid, 3R,1S-1-(2,4-difluorophenyl)-6-fluoro-1,4-dihydro-7-3-[1-(methylamino)ethyl]-1-pyrrolidinyl]-4-oxo-3-quinolinecarboxylic acid, 3R,1S-5-amino-1-cyclopropyl-6-fluoro-1,4-dihydro-7-[3-[1-(methylamino)ethyl]-1-pyrrolidinyl]-4-oxo-3-quinolinecarboxylic acid, 3R,1S-1-cyclopropyl-6-fluoro-1,4-dihydro-5-methyl-7-[3-[1-(methylamino)ethyl]-1-pyrrolidinyl]-4-oxo-3-quinolinecarboxylic acid, 3R,1S-1-cyclopropyl-8-ethoxy-6-fluoro-1,4-dihydro-7-[3-[1-(methylamino)ethyl]-1-pyrrolidinyl]-4-oxo-3-quinolinecarboxylic acid, 3R,1S-1-cyclopropyl-7-[3-[1-(ethylamino)ethyl]-1-pyrrolidinyl]-6-fluoro-1,4-dihydro-4-oxo-1,8-naphthyridine-3-carboxylic acid, 3R,1S-8-chloro-1-cyclopropyl-7-[3-[1-(ethylamino)ethyl]-1-pyrrolidinyl]-6-fluoro-1,4-dihydro-4-oxo-3-quinolinecarboxylic acid, 3R,1S-1-cyclopropyl-7-[3-[1-(ethylamino)ethyl]-1-pyrrolidinyl]-6-fluoro-1,4-dihydro-8-methoxy-4-oxo-3-quinolinecarboxylic acid, 3R,1S-5-amino-1-cyclopropyl-7-[3-[1-(ethylamino)ethyl]-1-pyrrolidinyl]-6,8-difluoro-1,4-dihydro-4-oxo-3-quinolinecarboxylic acid, 3R,1S-1-cyclopropyl-7-[3-[1-(ethylamino)ethyl]-1-pyrrolidinyl]-6-fluoro-1,4-dihydro-4-oxo-3-quinolinecarboxylic acid, 3R,1S-5-amino-1-cyclopropyl-7-[3-[1-(ethylamino)ethyl]-1-pyrrolidinyl]-6-fluoro-1,4-dihydro-8-methoxy-4-oxo-3-quinolinecarboxylic acid, 3R,1S-1-(2,4-difluorophenyl)-7-[3-[1-(ethylamino)ethyl]-1-pyrrolidinyl]-6-fluoro-1,4-dihydro-5-methyl-4-oxo-3-quinolinecarboxylic acid, 3R,1S-1-cyclopropyl-7-[3-[1-(ethylamino)ethyl]-1-pyrrolidinyl]-6-fluoro-1,4-dihydro-4-oxo-8-trifluoromethyl-3-quinolinecarboxylic acid, 3R,1S-1-(2,4-difluorophenyl)-7-[3-[1-(ethylamino)ethyl]-1-pyrrolidinyl]-6-fluoro-1,4-dihydro-4-oxo-3-quinolinecarboxylic acid, 3R,1S-1-(2,4-difluorophenyl)-7-[3-[1-(ethylamino)ethyl]-1-pyrrolidinyl]-6-fluoro-1,4-dihydro-4-oxo-1,8-naphthyridine-3-carboxylic acid, 3R,1S-5-amino-1-cyclopropyl-7-[3-[1-(ethylamino)-ethyl]-1-pyrrolidinyl]-6-fluoro-1,4-dihydro-4-oxo-3-quinolinecarboxylic acid, 3R,1S-1-cyclopropyl-7-[3-[1-(ethylamino)ethyl]-1-pyrrolidinyl]-6-fluoro-1,4-dihydro-5-methyl-4-oxo-3-quinolinecarboxylic acid, 3R,1S-1-cyclopropyl-8-ethoxy-7-[3-[1-(ethylamino)-ethyl]-1-pyrrolidinyl]-6-fluoro-1,4-dihydro-4-oxo-3-quinolinecarboxylic acid, 3R,1S-1-cyclopropyl-7-[3-[1-(dimethylamino)ethyl]-1-pyrrolidinyl]-6-fluoro-1,4-dihydro-4-oxo-1,8-naphthyridine-3-carboxylic acid, 3R,1S-1-cyclopropyl-7-[3-[1-(dimethylamino)ethyl]-1-pyrrolidinyl]-6-fluoro-1,4-dihydro-8-methoxy-4-oxo-3-quinolinecarboxylic acid, 3R,1S-5-amino-1-cyclopropyl-7-[3-[1-(dimethylamino)ethyl]-1-pyrrolidinyl]-6,8-difluoro-1,4-dihydro-4-oxo-3-quinolinecarboxylic acid, 3R,1S-1-cyclopropyl-7-[3-[1-(dimethylamino)ethyl]-1-pyrrolidinyl]-6-fluoro-1,4-dihydro-4-oxo-3-quinolinecarboxylic acid, 3R,1S-8-chloro-1-cyclopropyl-7-[3-[1-(dimethylamino)ethyl]-1-pyrrolidinyl]-6-fluoro-1,4-dihydro-4-oxo-3-quinolinecarboxylic acid, 3R,1S-5-amino-1-cyclopropyl-7-[3-[1-(dimethylamino)ethyl]-1-pyrrolidinyl]-6-fluoro-1,4-dihydro-8-methoxy-4-oxo-3-quinolinecarboxylic acid, 3R,1S-1-cyclopropyl-7-[3-[1-(dimethylamino)ethyl]-1-pyrrolidinyl]-6-fluoro-1,4-dihydro-8-trifluoromethyl-4-oxo-3-quinolinecarboxylic acid, 3R,1S-1-(2,4-difluorophenyl)-7-[3-[1-(dimethylamino)ethyl]-1-pyrrolidinyl]-6-fluoro-1,4-dihydro-4-oxo-3-quinolinecarboxylic acid, 3R,1S-1-(2,4-difluorophenyl)-7-[3-[1-(dimethylamino)ethyl]-1-pyrrolidinyl]-6-fluoro-1,4-dihydro-4-oxo-1,8-naphthyridine-3-carboxylic acid, 3R,1S-1-(2,4-difluorophenyl)-7-[3-[1-(dimethylamino)ethyl]-1-pyrrolidinyl]-6-fluoro-1,4-dihydro-5-methyl-4-oxo-3-quinolinecarboxylic acid, 3R,1S-5-amino-1-cyclopropyl-7-[3-[1-(dimethylamino)ethyl]-1-pyrrolidinyl]-6-fluoro-1,4-dihydro-4-oxo-3-quinolinecarboxylic acid, 3R,1S-1-cyclopropyl-7-[3-[1-(dimethylamino)ethyl]-1-pyrrolidinyl]-6-fluoro-1,4-dihydro-5-methyl-4-oxo-3-quinolinecarboxylic acid, 3R,1S-1-cyclopropyl-7-[3-[1-(dimethylamino)ethyl]-1-pyrrolidinyl]-8-ethoxy-6-fluoro-1,4-dihydro-4-oxo-3-quinolinecarboxylic acid, 3S,1R-7-[3-(1-aminoethyl)-1-pyrrolidinyl]-1-cyclopropyl-6-fluoro-1,4-dihydro-4-oxo-1,8-naphthyridine-3-carboxylic acid, 3S,1R-7-[3-(1-aminoethyl)-1-pyrrolidinyl]-8-chloro-1-cyclopropyl-6-fluoro-1,4-dihydro-4-oxo-3-quinolinecarboxylic acid, 3S,1R-7-[3-(1-aminoethyl)-1-pyrrolidinyl]-1-cyclopropyl-6-fluoro-1,4-dihydro-4-oxo-3-quinolinecarboxylic acid, 3S,1R-5-amino-7-[3-(1-aminoethyl)-1-pyrrolidinyl]-1-cyclopropyl-6,8-difluoro-1,4-dihydro-4-oxo-3-quinolinecarboxylic acid, 3S,1R-7-[3-(1-aminoethyl)-1-pyrrolidinyl]-1-cyclopropyl-6-fluoro-1,4-dihydro-8-methoxy-4-oxo-3-quinolinecarboxylic acid, 3S,1R-5-amino-7-[3-(1-aminoethyl)-1-pyrrolidinyl]-1-cyclopropyl-6-fluoro-1,4-dihydro-8-methoxy-4-oxo-3-quinolinecarboxylic acid, 3S,1R-7-[3-(1-aminoethyl)-1-pyrrolidinyl]-1-cyclopropyl-6-fluoro-1,4-dihydro-4-oxo-8-trifluoromethyl-3-quinolinecarboxylic acid, 3S,1R-7-[3-(1-aminoethyl)-1-pyrrolidinyl]-1-(2,4-difluorophenyl)-6-fluoro-1,4-dihydro-5-methyl-4-oxo-3-quinolinecarboxylic acid, 3S,1R-7-[3-(1-aminoethyl)-1-pyrrolidinyl]-1-(2,4-difluorophenyl)-6-fluoro-1,4-dihydro-4-oxo-1,8-naphthyridine-3-carboxylic acid, 3S,1R-7-[3-(1-aminoethyl)-1-pyrrolidinyl]-1-(2,4-difluorophenyl)-6-fluoro-1,4-dihydro-4-oxo-3-quinolinecarboxylic acid, 3S,1R-5-amino-7-[3-(1-aminoethyl)-1-pyrrolidinyl]-1-cyclopropyl-6-fluoro-1,4-dihydro-4-oxo-3-quinolinecarboxylic acid, 3S,1R-7-[3-(1-aminoethyl)-1-pyrrolidinyl]-1-cyclopropyl-6-fluoro-1,4-dihydro-5-methyl-4-oxo-3-quinolinecarboxylic acid, 3S,1R-7-[3-(1-aminoethyl)-1-pyrrolidinyl]-1-cyclopropyl-8-ethoxy-6-fluoro-1,4-dihydro-4-oxo-3-quinolinecarboxylic acid, 3S,1R-1-cyclopropyl-6-fluoro-1,4-dihydro-7-[3-[1-(methylamino)ethyl]-1-pyrrolidinyl]-1,8-naphthyridine-3-carboxylic acid, 3S,1R-8-chloro-1-cyclopropyl-6-fluoro-1,4-dihydro-7-[3-[1-(methylamino)ethyl]-1-pyrrolidinyl]-4-oxo-3-quinolinecarboxylic acid, 3S,1R-5-amino-1-cyclopropyl-6,8-difluoro-1,4-dihydro-7-[3-[1-(methylamino)ethyl]-1-pyrrolidinyl]-4-oxo-3-quinolinecarboxylic acid, 3S,1R-1-cyclopropyl-6-fluoro-1,4-dihydro-7-[3-[1-(methylamino)ethyl]-1-pyrrolidinyl]-4-oxo-3-quinolinecarboxylic acid, 3S,1R-1-cyclopropyl-6-fluoro-1,4-dihydro-8-methoxy-7-[3-[1-(methylamino)ethyl]-1-pyrrolidinyl]-4-oxo-3-quinolinecarboxylic acid, 3S,1R-5-amino-1-cyclopropyl-6-fluoro-1,4-dihydro-8-methoxy-7-[3-[1-(methylamino)ethyl]-1-pyrrolidinyl]-4-oxo-3-quinolinecarboxylic acid, 3S,1R-1-cyclopropyl-6-fluoro-1,4-dihydro-7-[3-[1-(methylamino)ethyl]-1-pyrrolidinyl]-4-oxo-8-trifluoromethyl-3-quinolinecarboxylic acid, 3S,1R-1-(2,4-difluorophenyl)-6-fluoro-1,4-dihydro-5-methyl-7-[3-[1-(methylamino)ethyl]-1-pyrrolidinyl]-4-oxo-3-quinolinecarboxylic acid, 3S,1R-1-(2,4-difluorophenyl)-6-fluoro-1,4-dihydro-7-[3-[1-(methylamino)ethyl]-1-pyrrolidinyl]-4-oxo-1,8-naphthyridine-3-carboxylic acid, 3S,1R-1-(2,4-difluorophenyl)-6-fluoro-1,4-dihydro-7-[3-[1-(methylamino)ethyl]-1-pyrrolidinyl]-4-oxo-3-quinolinecarboxylic acid, 3S,1R-5-amino-1-cyclopropyl-6-fluoro-1,4-dihydro-7-[3-[1-(methylamino)ethyl]-1-pyrrolidinyl]-4-oxo-3-quinolinecarboxylic acid, 3S,1R-1-cyclopropyl-6-fluoro-1,4-dihydro-5-methyl-7-[3-[1-(methylamino)ethyl]-1-pyrrolidinyl]-4-oxo-3-quinolinecarboxylic acid, 3S,1R-1-cyclopropyl-8-ethoxy-6-fluoro-1,4-dihydro-7-[3-[1-(methylamino)ethyl]-1-pyrrolidinyl]-4-oxo-3-quinolinecarboxylic acid, 3S,1R-1-cyclopropyl-7-[3-[1-(ethylamino)ethyl]-1-pyrrolidinyl]-6-fluoro-1,4-dihydro-4-oxo-1,8-naphthyridine-3-carboxylic acid, 3S,1R-8-chloro-1-cyclopropyl-7-[3-[1-(ethylamino)ethyl]-1-pyrrolidinyl]-6-fluoro-1,4-dihydro-4-oxo-3-quinolinecarboxylic acid, 3S,1R-1-cyclopropyl-7-[3-[1-(ethylamino)ethyl]-1-pyrrolidinyl]-6-fluoro-1,4-dihydro-8-methoxy-4-oxo-3-quinolinecarboxylic acid, 3S,1R-5-amino-1-cyclopropyl-7-[3-[1-(ethylamino)ethyl]-1-pyrrolidinyl]-6,8-difluoro-1,4-dihydro-4-oxo-3-quinolinecarboxylic acid, 3S,1R-1-cyclopropyl-7-[3-[1-(ethylamino)ethyl]-1-pyrrolidinyl]-6-fluoro-1,4-dihydro-4-oxo-3-quinolinecarboxylic acid, 3S,1R-5-amino-1-cyclopropyl-7-[3-[1-(ethylamino)ethyl]-1-pyrrolidinyl]-6-fluoro-1,4-dihydro-8-methoxy-4-oxo-3-quinolinecarboxylic acid, 3S,1R-1-(2,4-difluorophenyl)-7-[3-[1-(ethylamino)ethyl]-1-pyrrolidinyl]-6-fluoro-1,4-dihydro-5-methyl-4-oxo-3-quinolinecarboxylic acid, 3S,1R-1-cyclopropyl-7-[3-[1-(ethylamino)ethyl]-1-pyrrolidinyl]-6-fluoro-1,4-dihydro-4-oxo-8-trifluoromethyl-3-quinolinecarboxylic acid, 3S,1R-1-(2,4-difluorophenyl)-7-[3-[1-(ethylamino)ethyl]-1-pyrrolidinyl]-6-fluoro-1,4-dihydro-4-oxo-3-quinolinecarboxylic acid, 3S,1R-1-(2,4-difluorophenyl)-7-[3-[1-(ethylamino)ethyl]-1-pyrrolidinyl]-6-fluoro-1,4-dihydro-4-oxo-1,8-naphthyridine-3-carboxylic acid, 3S,1R-5-amino-1-cyclopropyl-7-[3-[1-(ethylamino)-ethyl]-1-pyrrolidinyl]-6-fluoro-1,4-dihydro-4-oxo-3-quinolinecarboxylic acid, 3S,1R-1-cyclopropyl-7-[3-[1-(ethylamino)ethyl]-1-pyrrolidinyl]-6-fluoro-1,4-dihydro-5-methyl-4-oxo-3-quinolinecarboxylic acid, 3S,1R-1-cyclopropyl-8-ethoxy-7-[3-[1-(ethylamino)ethyl]-1-pyrrolidinyl]-6-fluoro-1,4-dihydro-4-oxo-3-quinolinecarboxylic acid, 3S,1R-1-cyclopropyl-7-[3-[1-(dimethylamino)ethyl]-1-pyrrolidinyl]-6-fluoro-1,4-dihydro-4-oxo-1,8-naphthyridine-3-carboxylic acid, 3S,1R-1-cyclopropyl-7-[3-[1-(dimethylamino)ethyl]-1-pyrrolidinyl]-6-fluoro-1,4-dihydro-8-methoxy-4-oxo-3-quinolinecarboxylic acid, 3S,1R-5-amino-1-cyclopropyl-7-[3-[1-(dimethylamino)ethyl]-1-pyrrolidinyl]-6,8-difluoro-1,4-dihydro-4-oxo-3-quinolinecarboxylic acid, 3S,1R-1-cyclopropyl-7-[3-[1-(dimethylamino)ethyl]-1-pyrrolidinyl]-6-fluoro-1,4-dihydro-4-oxo-3-quinolinecarboxylic acid, 3S,1R-8-chloro-1-cyclopropyl-7-[3-[1-(dimethylamino)ethyl]-1-pyrrolidinyl]-6-fluoro-1,4-dihydro-4-oxo-3-quinolinecarboxylic acid, 3S,1R-1-cyclopropyl-7-[3-[1-(dimethylamino)ethyl]-1-pyrrolidinyl]-6-fluoro-1,4-dihydro-8-methoxy-4-oxo-3-quinolinecarboxylic acid, 3S,1R-1-cyclopropyl-7-[3-[1-(dimethylamino)ethyl]-1-pyrrolidinyl]-6-fluoro-1,4-dihydro-8-trifluoromethyl-3-quinolinecarboxylic acid, 3S,1R-1-(2,4-difluorophenyl)-7-[3-[1-(dimethylamino)ethyl]-1-pyrrolidinyl]-6-fluoro-1,4-dihydro-4-oxo-3-quinolinecarboxylic acid, 3S,1R-1-(2,4-difluorophenyl)-7-[3-[1-(dimethylamino)ethyl]-1-pyrrolidinyl]-6-fluoro-1,4-dihydro-4-oxo-1,8-naphthyridine-3-carboxylic acid, 3S,1R-1-(2,4-difluorophenyl)-7-[3-[1-(dimethylamino)ethyl]-1-pyrrolidinyl]-6-fluoro-1,4-dihydro-5-methyl-4-oxo-3-quinolinecarboxylic acid, 3S,1R-5-amino-1-cyclopropyl-7-[3-[1-(dimethylamino)ethyl]-1-pyrrolidinyl]-6-fluoro-1,4-dihydro-4-oxo-3-quinolinecarboxylic acid, 3S,1R-1-cyclopropyl-7-[3-[1-(dimethylamino)ethyl]-1-pyrrolidinyl]-6-fluoro-1,4-dihydro-5-methyl-4-oxo-3-quinolinecarboxylic acid, 3S,1R-1-cyclopropyl-7-[3-[1-(dimethylamino)ethyl]-1-pyrrolidinyl]-8-ethoxy-6-fluoro-1,4-dihydro-4-oxo-3-quinolinecarboxylic acid, 3R,1R-7-[3-(1-aminoethyl)-1-pyrrolidinyl]-1-cyclopropyl-6-fluoro-1,4-dihydro-4-oxo-1,8-naphthyridine-3-carboxylic acid, 3R,1R-7-[3-(1-aminoethyl)-1-pyrrolidinyl]-8-chloro-1-cyclopropyl-6-fluoro-1,4-dihydro-4-oxo-3-quinolinecarboxylic acid, 3R,1R-7-[3-(1-aminoethyl)-1-pyrrolidinyl]-1-cyclopropyl-6-fluoro-1,4-dihydro-4-oxo-3-quinolinecarboxylic acid, 3R,1R-5-amino-7-[3-(1-aminoethyl)-1-pyrrolidinyl]-1-cyclopropyl-6,8-difluoro-1,4-dihydro-4-oxo-3-quinolinecarboxylic acid, 3R,1R-7-[3-(1-aminoethyl)-1-pyrrolidinyl]-1-cyclopropyl-6-fluoro-1,4-dihydro-8-methoxy-4-oxo-3-quinolinecarboxylic acid, 3R,1R-5-amino-7-[3-(1-aminoethyl)-1-pyrrolidinyl]-1-cyclopropyl-6-fluoro-1,4-dihydro-8-methoxy-4-oxo-3-quinolinecarboxylic acid, 3R,1R-7-[3-(1-aminoethyl)-1-pyrrolidinyl]-1-cyclopropyl-6-fluoro-1,4-dihydro-4-oxo-8-trifluoromethyl-3-quinolinecarboxylic acid, 3R,1R-7-[3-(1-aminoethyl)-1-pyrrolidinyl]-1-(2,4-difluorophenyl)-6-fluoro-1,4-dihydro-5-methyl-4-oxo-3-quinolinecarboxylic acid, 3R,1R-7-[3-(1-aminoethyl)-1-pyrrolidinyl]-1-(2,4-difluorophenyl)-6-fluoro-1,4-dihydro-4-oxo-1,8-naphthyridine-3-carboxylic acid, 3R,1R-7-[3-(1-aminoethyl)-1-pyrrolidinyl]-1-(2,4-difluorophenyl)-6-fluoro-1,4-dihydro-4-oxo-3-quinolinecarboxylic acid, 3R,1R-5-amino-7-[3-(1-aminoethyl)-1-pyrrolidinyl]-1-cyclopropyl-6-fluoro-1,4-dihydro-4-oxo-3-quinolinecarboxylic acid, 3R,1R-7-[3-(1-aminoethyl)-1-pyrrolidinyl]-1-cyclopropyl-6-fluoro-1,4-dihydro-5-methyl-4-oxo-3-quinolinecarboxylic acid, 3R,1R-7-[3-(1-aminoethyl)-1-pyrrolidinyl]-1-cyclopropyl-8-ethoxy-6-fluoro-1,4-dihydro-4-oxo-3-quinolinecarboxylic acid, 3R,1R-1-cyclopropyl-6-fluoro-1,4-dihydro-7-[3-[1-(methylamino)ethyl]-1-pyrrolidinyl]-1,8-naphthyridine-3-carboxylic acid, 3R,1R-8-chloro-1-cyclopropyl-6-fluoro-1,4-dihydro-7-[3-[1-(methylamino)ethyl]-1-pyrrolidinyl]-4-oxo-3-quinolinecarboxylic acid, 3R,1R-5-amino-1-cyclopropyl-6,8-difluoro-1,4-dihydro-7-[3-[1-(methylamino)ethyl]-1-pyrrolidinyl]-4-oxo-3-quinolinecarboxylic acid, 3R,1R-1-cyclopropyl-6-fluoro-1,4-dihydro-7-[3-[1-(methylamino)ethyl]-1-pyrrolidinyl]-4-oxo-3-quinolinecarboxylic acid, 3R,1R-1-cyclopropyl-6-fluoro-1,4-dihydro-8-methoxy-7-[3-[1-(methylamino)ethyl]-1-pyrrolidinyl]-4-oxo-3-quinolinecarboxylic acid, 3R,1R-5-amino-1-cyclopropyl-6-fluoro-1,4-dihydro-8-methoxy-7-[3-[1-(methylamino)ethyl]-1-pyrrolidinyl]-4-oxo-3-quinolinecarboxylic acid, 3R,1R-1-cyclopropyl-6-fluoro-1,4-dihydro-7-[3-[1-(methylamino)ethyl]-1-pyrrolidinyl]-4-oxo-8-trifluoromethyl-3-quinolinecarboxylic acid, 3R,1R-1-(2,4-difluorophenyl)-6-fluoro-1,4-dihydro-5-methyl-7-[3-[1-(methylamino)ethyl]-1-pyrrolidinyl]-4-oxo-3-quinolinecarboxylic acid, 3R,1R-1-(2,4-difluorophenyl)-6-fluoro-1,4-dihydro-7-[3-[1-(methylamino)ethyl]-1-pyrrolidinyl]-4-oxo-1,8-naphthyridine-3-carboxylic acid, 3R,1R-1-(2,4-difluorophenyl)-6-fluoro-1,4-dihydro-7-[3-[1-(methylamino)ethyl]-1-pyrrolidinyl]-4-oxo-3-quinolinecarboxylic acid, 3R,1R-5-amino-1-cyclopropyl-6-fluoro-1,4-dihydro-7-[3-[1-(methylamino)ethyl]-1-pyrrolidinyl]-4-oxo-3-quinolinecarboxylic acid, 3R,1R-1-cyclopropyl-6-fluoro-1,4-dihydro-5-methyl-7-[3-[1-(methylamino)ethyl]-1-pyrrolidinyl]-4-oxo-3-quinolinecarboxylic acid, 3R,1R-1-cyclopropyl-8-ethoxy-6-fluoro-1,4-dihydro-7-[3-[1-(methylamino)ethyl]-1-pyrrolidinyl]-4-oxo-3-quinolinecarboxylic acid, 3R,1R-1-cyclopropyl-7-[3-[1-(ethylamino)ethyl]-1-pyrrolidinyl]-6-fluoro-1,4-dihydro-4-oxo-1,8-naphthyridine-3-carboxylic acid, 3R,1R-8-chloro-1-cyclopropyl-7-[3-[1-(ethylamino)ethyl]-1-pyrrolidinyl]-6-fluoro-1,4-dihydro-4-oxo-3-quinolinecarboxylic acid, 3R,1R-1-cyclopropyl-7-[3-[1-(ethylamino)ethyl]-1-pyrrolidinyl]-6-fluoro-1,4-dihydro-8-methoxy-4-oxo-3-quinolinecarboxylic acid, 3R,1R-5-amino-1-cyclopropyl-7-[3-[1-(ethylamino)ethyl]-1-pyrrolidinyl]-6,8-difluoro-1,4-dihydro-4-oxo-3-quinolinecarboxylic acid, 3R,1R-1-cyclopropyl-7-[3-[1-(ethylamino)ethyl]-1-pyrrolidinyl]-6-fluoro-1,4-dihydro-4-oxo-3-quinolinecarboxylic acid, 3R,1R-5-amino-1-cyclopropyl-7-[3-[1-(ethylamino)ethyl]-1-pyrrolidinyl]-6-fluoro-1,4-dihydro-8-methoxy-4-oxo-3-quinolinecarboxylic acid, 3R,1R-1-(2,4-difluorophenyl)-7-[3-[1-(ethylamino)ethyl]-1-pyrrolidinyl]-6-fluoro-1,4-dihydro-5-methyl-4-oxo-3-quinolinecarboxylic acid, 3R,1R-1-cyclopropyl-7-[3-[1-(ethylamino)ethyl]-1-pyrrolidinyl]-6-fluoro-1,4-dihydro-4-oxo-8-trifluoromethyl-3-quinolinecarboxylic acid, 3R,1R-1-(2,4-difluorophenyl)-7-[3-[1-(ethylamino)ethyl]-1-pyrrolidinyl]-6-fluoro-1,4-dihydro-4-oxo-3-quinolinecarboxylic acid, 3R,1R-1-(2,4-difluorophenyl)-7-[3-[1-(ethylamino)ethyl]-1-pyrrolidinyl]-6-fluoro-1,4-dihydro-4-oxo-1,8-naphthyridine-3-carboxylic acid, 3R,1R-5-amino-1-cyclopropyl-7-[3-[1-(ethylamino)ethyl]-1-pyrrolidinyl]-6-fluoro-1,4-dihydro-4-oxo-3-quinolinecarboxylic acid, 3R,1R-1-cyclopropyl-7-[3-[1-(ethylamino)ethyl]-1-pyrrolidinyl]-6-fluoro-1,4-dihydro-5-methyl-4-oxo-3-quinolinecarboxylic acid, 3R,1R-1-cyclopropyl-8-ethoxy-7-[3-[1-(ethylamino)ethyl]-1-pyrrolidinyl]-6-fluoro-1,4-dihydro-4-oxo-3-quinolinecarboxylic acid, 3R,1R-1-cyclopropyl-7-[3-[1-(dimethylamino)ethyl]-1-pyrrolidinyl]-6-fluoro-1,4-dihydro-4-oxo-1,8-naphthyridine-3-carboxylic acid, 3R,1R-1-cyclopropyl-7-[3-[1-(dimethylamino)ethyl]-1-pyrrolidinyl]-6-fluoro-1,4-dihydro-8-methoxy-4-oxo-3-quinolinecarboxylic acid, 3R,1R-5-amino-1-cyclopropyl-7-[3-[1-(dimethylamino)ethyl]-1-pyrrolidinyl]-6,8-difluoro-1,4-dihydro-4-oxo-3-quinolinecarboxylic acid, 3R,1R-1-cyclopropyl-7-[3-[1-(dimethylamino)ethyl]-1-pyrrolidinyl]-6-fluoro-1,4-dihydro-4-oxo-3-quinolinecarboxylic acid, 3R,1R-8-chloro-1-cyclopropyl-7-[3-[1-(dimethylamino)ethyl]-1-pyrrolidinyl]-6-fluoro-1,4-dihydro-4-oxo-3-quinolinecarboxylic acid, 3R,1R-5-amino-1-cyclopropyl-7-[3-[1-(dimethylamino)ethyl]-1-pyrrolidinyl]-6-fluoro-1,4-dihydro-8-methoxy-4-oxo-3-quinolinecarboxylic acid, 3R,1R-1-cyclopropyl-7-[3-[1-(dimethylamino)ethyl]-1-pyrrolidinyl]-6-fluoro-1,4-dihydro-8-trifluoromethyl-3-quinolinecarboxylic acid, 3R,1R-1-(2,4-difluorophenyl)-7-[3-[1-(dimethylamino)ethyl]-1-pyrrolidinyl]-6-fluoro-1,4-dihydro-4-oxo-3-quinolinecarboxylic acid, 3R,1R-1-(2,4-difluorophenyl)-7-[3-[1-(dimethylamino)ethyl]-1-pyrrolidinyl]-6-fluoro-1,4-dihydro-4-oxo-1,8-naphthyridine-3-carboxylic acid, 3R,1R-1-(2,4-difluorophenyl)-7-[3-[1-(dimethylamino)ethyl]-1-pyrrolidinyl]-6-fluoro-1,4-dihydro-5-methyl-4-oxo-3-quinolinecarboxylic acid, 3R,1R-5-amino-1-cyclopropyl-7-[3-[1-(dimethylamino)ethyl]-1-pyrrolidinyl]-6-fluoro-1,4-dihydro-4-oxo-3-quinolinecarboxylic acid, 3R,1R-1-cyclopropyl-7-[3-[1-(dimethylamino)ethyl]-1-pyrrolidinyl]-6-fluoro-1,4-dihydro-5-methyl-4-oxo-3-quinolinecarboxylic acid, and 3R,1R-1-cyclopropyl-7-[3-[1-(dimethylamino)ethyl]-1-pyrrolidinyl]-8-ethoxy-6-fluoro-1,4-dihydro-4-oxo-3-quinolinecarboxylic acid.

Particularly valuable enantiomers of 7-[3-(1 aminoalkyl)-1-pyrrolidines and additional novel intermediates used to prepare the 7-side chain for the final products are:

FINAL AMINES FOR COUPLING (3R,1'R)-3-(1'-aminoethyl)pyrrolidine
(3R,1'S)-3-(1'-aminoethyl)pyrrolidine
(3S,1'R)-3-(1'-aminoethyl)pyrrolidine
(3S,1'S)-3-(1'-aminoethyl)pyrrolidine (3R,1'R)-3-(1'-N-methylaminoethyl)pyrrolidine
(3R,1'S)-3-(1'-N-methylaminoethyl)pyrrolidine
(3S,1'R)-3-(1'-N-methylaminoethyl)pyrrolidine
(3S,1'S)-3-(1'-N-methylaminoethyl)pyrrolidine
(3R,1'R)-3-(1'-N-ethylaminoethyl)pyrrolidine
(3R,1'S)-3-(1'-N-ethylaminoethyl)pyrrolidine
(3S,1'R)-3-(1'-N-ethylaminoethyl)pyrrolidine
(3S,1'S)-3-(1'-N-ethylaminoethyl)pyrrolidine
(3R,1'R)-3-(1'-N,N-dimethylaminoethyl)pyrrolidine
(3R,1'S)-3-(1'-N,N-dimethylaminoethyl)pyrrolidine
(3S,1'R)-3-(1'-N,N-dimethylaminoethyl)pyrrolidine
(3S,1'S)-3-(1'-N,N-dimethylaminoethyl)pyrrolidine
(3R,1'R)-3-(1'-N-t-butyloxycarbonylaminoethyl)pyrrolidine
(3R,1'S)-3-(1'-N-t-butyloxycarbonylaminoethyl)pyrrolidine
(3S,1'R)-3-(1'-N-t-butyloxycarbonylaminoethyl)pyrrolidine
(3S,1'S)-3-(1'-N-t-butyloxycarbonylaminoethyl)pyrrolidine
(3R,1'R)-3-(1'-N-methyl-N-t-butyloxycarbonylaminoethyl)pyrrolidine
(3R,1'S)-3-(1'-N-methyl-N-t-butyloxycarbonylaminoethyl)pyrrolidine
(3S,1'R)-3-(1'-N-methyl-N-t-butyloxycarbonylaminoethyl)pyrrolidine
(3S,1'S)-3-(1'-N-methyl-N-t-butyloxycarbonylaminoethyl)pyrrolidine

N1 BENZYL INTERMEDIATES (3R,1'R)-3-(1'-aminoethyl)-1-(S-α-methylbenzyl)pyrrolidine
(3R,1'S)-3-(1'-aminoethyl)-1-(S-α-methylbenzyl)pyrrolidine
(3S,1'R)-3-(1'-aminoethyl)-1-(S-α-methylbenzyl)pyrrolidine
(3S,1'S)-3-(1'-aminoethyl)-1-(S-α-methylbenzyl)pyrrolidine
(3R,1'R)-3-(1'-N-methylaminoethyl)-1-(S-α-methylbenzyl)pyrrolidine
(3R,1'S)-3-(1'-N-methylaminoethyl)-1-(S-α-methylbenzyl)pyrrolidine
(3S,1'R)-3-(1'-N-methylaminoethyl)-1-(S-α-methylbenzyl)pyrrolidine
(3S,1'S)-3-(1'-N-methylaminoethyl)-1-(S-α-methylbenzyl)pyrrolidine
(3R,1'R)-3-(1'-N-ethylaminoethyl)-1-(S-α-methylbenzyl)pyrrolidine
(3R,1'S)-3-(1'-N-ethylaminoethyl)-1-(S-α-methylbenzyl)pyrrolidine
(3S,1'R)-3-(1'-N-ethylaminoethyl)-1-(S-α-methylbenzyl)pyrrolidine
(3S,1'S)-3-(1'-N-ethylaminoethyl)-1-(S-α-methylbenzyl)pyrrolidine
(3R,1'R)-3-(1'-N,N-dimethylaminoethyl)-1-(S-α-methylbenzyl)pyrrolidine
(3R,1'S)-3-(1'-N,N-dimethylaminoethyl)-1-(S-α-methylbenzyl)pyrrolidine
(3S,1'R)-3-(1'-N,N-dimethylaminoethyl)-1-(S-α-methylbenzyl)pyrrolidine
(3S,1'S)-3-(1'-N,N-dimethylaminoethyl)-1-(S-α-methylbenzyl)pyrrolidine
(3R,1'R)-3-(1'-N-t-butyloxycarbonylaminoethyl)-1-(S-α-methylbenzyl)pyrrolidine
(3R,1'S)-3-(1'-N-t-butyloxycarbonylaminoethyl)-1-(S-α-methylbenzyl)pyrrolidine
(3S,1'R)-3-(1'-N-t-butyloxycarbonylaminoethyl)-1-(S-α-methylbenzyl)pyrrolidine
(3S,1'S)-3-(1'-N-t-butyloxycarbonylaminoethyl)-1-(S-α-methylbenzyl)pyrrolidine
(3R,1'R)-3-(1'-N-methyl-N-t-butyloxycarbonylaminoethyl)-1-(S-α-methylbenzyl)pyrrolidine
(3R,1'S)-3-(1'-N-methyl-N-t-butyloxycarbonylaminoethyl)-1-(S-α-methylbenzyl)pyrrolidine
(3S,1'R)-3-(1'-N-methyl-N-t-butyloxycarbonylaminoethyl)-1-(S-α-methylbenzyl)pyrrolidine
(3S,1'S)-3-(1'-N-methyl-N-t-butyloxycarbonylaminoethyl)-1 -(S-α-methylbenzyl)pyrrolidine
(3R,1'R)-3-(1'-aminoethyl)-1-(R-α-methylbenzyl)pyrrolidine
(3R,1'S)-3-(1-aminoethyl)-1-(R-α-methylbenzyl)pyrrolidine
(3S,1'R)-3-(1'-aminoethyl)-1-(R-α-methylbenzyl)pyrrolidine
(3S,1'S)-3-(1'-aminoethyl)-1-(R-α-methylbenzyl)pyrrolidine
(3R,1'R)-3-(1'-N-methylaminoethyl)-1-(R-α-methylbenzyl)pyrrolidine
(3R,1'S)-3-(1'-N-methylaminoethyl)-1-(R-α-methylbenzyl)pyrrolidine
(3S,1'R)-3-(1'-N-methylaminoethyl)-1-(R-α-methylbenzyl)pyrrolidine
(3S,1'S)-3-(1'-N-methylaminoethyl)-1-(R-α-methylbenzyl)pyrrolidine
(3R,1'R)-3-(1'-N-ethylaminoethyl)-1-(R-α-methylbenzyl)pyrrolidine
(3R,1'S)-3-(1'-N-ethylaminoethyl)-1-(R-α-methylbenzyl)pyrrolidine
(3S,1'R)-3-(1'-N-ethylaminoethyl)-1-(R-α-methylbenzyl)pyrrolidine
(3S,1'S)-3-(1'-N-ethylaminoethyl)-1-(R-α-methylbenzyl)pyrrolidine
(3R,1'R)-3-(1'-N,N-dimethylaminoethyl)-1-(R-α-methylbenzyl)pyrrolidine
(3R,1'S)-3-(1'-N,N-dimethylaminoethyl)-1-(R-α-methylbenzyl)pyrrolidine
(3S,1'R)-3-(1'-N,N-dimethylaminoethyl)-1-(R-α-methylbenzyl)pyrrolidine
(3S,1'S)-3-(1'-N,N-dimethylaminoethyl)-1-(R-α-methylbenzyl)pyrrolidine
(3R,1'R)-3-(1'-N-t-butyloxycarbonylaminoethyl)-1-(R-α-methylbenzyl)pyrrolidine
(3S,1'S)-3-(1'-N-t-butyloxycarbonylaminoethyl)-1-(R-α-methylbenzyl)pyrrolidine
(3S,1'R)-3-(1'-N-t-butyloxycarbonylaminoethyl)-1-(R-α-methylbenzyl)pyrrolidine
(3S,1'S)-3-(1'-N-t-butyloxycarbonylaminoethyl)-1 (R-α-methylbenzyl)pyrrolidine
(3R,1'R)-3-(1'-N-methyl-N-t-butyloxycarbonylaminoethyl)-1-(R-α-methylbenzyl)pyrrolidine
(3R,1'S)-3-(1'-N-methyl-N-t-butyloxycarbonylaminoethyl)-1-(R-α-methylbenzyl)pyrrolidine
(3S,1'R)-3-(1'-N-methyl-N-t-butyloxycarbonylaminoethyl)-1-(R-α-methylbenzyl)pyrrolidine
(3S,1'S)-3-(1'-N-methyl-N-t-butyloxycarbonylaminoethyl)-1-(R-α-methylbenzyl)pyrrolidine

PYRROLIDINONES (3R,1'R)-3-(1'-aminoethyl)-1-(S-α-methylbenzyl)pyrrolidin-5-one
(3R,1'S)-3-(1'-aminoethyl)-1-(S-α-methylbenzyl)pyrrolidin-5-one
(3S,1'R)-3-(1'-aminoethyl)-1-(S-α-methylbenzyl)pyrrolidin-5-one
(3S,1'S)-3-(1'-aminoethyl)-1-(S-α-methylbenzyl)pyrrolidin-5-one (3R,1'R)-3-(1'-N,N-dimethylaminoethyl)-1-(S-α-methylbenzyl)pyrrolidin-5-one
(3R,1'S)-3-(1'-N,N-dimethylaminoethyl)-1-(S-α-methylbenzyl)pyrrolidin-5-one
(3S,1'R)-3-(1'-N,N-dimethylaminoethyl)-1-(S-α-methylbenzyl)pyrrolidin-5-one
(3S,1'S)-3-(1'-N,N-dimethylaminoethyl)-1-(S-α-methylbenzyl)pyrrolidin-5-one
(3R,1'R)-3-(1'-N-acetylaminoethyl)-1-(S-α-methylbenzyl)pyrrolidin-5-one
(3R,1'S)-3-(1'-N-acetylaminoethyl)-1-(S-α-methylbenzyl)pyrrolidin-5-one
(3S,1'R)-3-(1'-N-acetylaminoethyl)-1-(S-α-methylbenzyl)pyrrolidin-5-one
(3S,1'S)-3-(1'-N-acetylaminoethyl)-1-(S-α-methylbenzyl)pyrrolidin-5-one
(3R,1'R)-3-(1'-N-t-butyloxycarbonylaminoethyl)-1-(S-α-methylbenzyl)pyrrolidin-5-one
(3R,1'S)-3-(1'-N-t-butyloxycarbonylaminoethyl)-1-(S-α-methylbenzyl)pyrrolidin-5-one
(3S,1'R)-3-(1'-N-t-butyloxycarbonylaminoethyl)-1-(S-α-methylbenzyl)pyrrolidin-5-one
(3S,1'S)-3-(1'-N-t-butyloxycarbonylaminoethyl)-1-(S-α-methylbenzyl)pyrrolidin-5-one
(3R,1'R)-3-(1'-aminoethyl)-1-(R-α-methylbenzyl)pyrrolidin-5-one
(3R,1'S)-3-(1'-aminoethyl)-1-(R-α-methylbenzyl)pyrrolidin-5-one
(3S,1'R)-3-(1'-aminoethyl)-1-(R-α-methylbenzyl)pyrrolidin-5-one
(3S,1'S)-3-(1'-aminoethyl)-1-(R-α-methylbenzyl)pyrrolidin-5-one
(3R,1'R)-3-(1'-N,N-dimethylaminoethyl)-1-(R-α-methylbenzyl)pyrrolidin-5-one
(3R,1'S)-3-(1'-N,N-dimethylaminoethyl)-1-(R-α-methylbenzyl)pyrrolidin-5-one
(3S,1'R)-3-(1'-N,N-dimethylaminoethyl)-1-(R-α-methylbenzyl)pyrrolidin-5-one
(3S,1'S)-3-(1'-N,N-dimethylaminoethyl)-1-(R-(α-methylbenzyl)pyrrolidin-5-one
(3R,1'R)-3-(1'-N-acetylaminoethyl)-1-(R-α-methylbenzyl)pyrrolidin-5-one
(3R,1'S)-3-(1'-N-acetylaminoethyl)-1-(R-α-methylbenzyl)pyrrolidin-5-one
(3S,1'R)-3-(1'-N-acetylaminoethyl)-1-(R-α-methylbenzyl)pyrrolidin-5-one
(3S,1'S)-3-(1'-N-acetylaminoethyl)-1-(R-α-methylbenzyl)pyrrolidin-5-one
(3R,1'R)-3-(1'-N-t-butyloxycarbonylaminoethyl)-1-(R-α-methylbenzyl)pyrrolidin-5-one
(3R,1'S)-3-(1'-N-t-butyloxycarbonylaminoethyl)-1-(R-α-methylbenzyl)pyrrolidin-5-one
(3S,1'R)-3-(1'-N-t-butyloxycarbonylaminoethyl)-1-(R-α-methylbenzyl)pyrrolidin-5-one
(3S,1'S)-3-(1'-N-t-butyloxycarbonylaminoethyl)-1-(R-α-methylbenzyl)pyrrolidin-5-one

OXIMES 3R-3-(1'-hydroxyaminoethyl)-1-(S-α-methylbenzyl)pyrrolidin-5-one
3S-3-(1'-hydroxyaminoethyl)-1-(S-α-methylbenzyl)pyrrolidin-5-one
3R-3-(1'-hydroxyaminoethyl)-1-(R-α-methylbenzyl)pyrrolidin-5-one
3S-3-(1'-hydroxyaminoethyl)-1-(R-α-methylbenzyl)pyrrolidin-5-one

KETONES 3-(acetyl)-1-(S-α-methylbenzyl)pyrrolidin-5-one
3-(acetyl)-1-(R-α-methylbenzyl)pyrrolidin-5-one
3R-3-(acetyl)-1-(S-α-methylbenzyl)pyrrolidin-5-one
3S-3-(acetyl)-1-(S-α-methylbenzyl)pyrrolidin-5-one
3R-3-(acetyl)-1-(R-α-methylbenzyl)pyrrolidin-5-one
3S-3-(acetyl)-1-(R-α-methylbenzyl)pyrrolidin-5-one

BETA KETO ESTERS 3-(2'-(ethoxycarbonyl)acetyl)-1-(S-α-methylbenzyl)pyrrolidin-5-one
3-(2'-(ethoxycarbonyl)acetyl)-1-(R-α-methylbenzyl)pyrrolidin-5-one
3R-3-(2'-(ethoxycarbonyl)acetyl)-1-(S-α-methylbenzyl)pyrrolidin-5-one
3S-3-(2'-(ethoxycarbonyl)acetyl)-1-(S-α-methylbenzyl)pyrrolidin-5-one
3R-3-(2'-(ethoxycarbonyl)acetyl)-1-(R-α-methylbenzyl)pyrrolidin-5-one
3S-3-(2'-(ethoxycarbonyl)acetyl)-1-(R-α-methylbenzyl)pyrrolidin-5-one

OTHER COMPOUNDS POSSIBLE (3R,1'R)-3-(1'-N-t-butyloxycarbonyl-N-methylaminoethyl)-1-(S-α-methylbenzyl)pyrrolidin-5-one
(3R,1'S)-3-(1'-N-t-butyloxycarbonyl-N-methylaminoethyl)-1-(S-α-methylbenzyl)pyrrolidin-5-one
(3S,1'R)-3-(1'-N-t-butyloxycarbonyl-N-methylaminoethyl)-1-(S-α-methylbenzyl)pyrrolidin-5-one
(3S,1'S)-3-(1'-N-t-butyloxycarbonyl-N-methylaminoethyl)-1-(S-α-methylbenzyl)pyrrolidin-5-one
(3R,1'R)-3-(1'-N-t-butyloxycarbonyl-N-methylaminoethyl)-1-(R-α-methylbenzyl)pyrrolidin-5-one
(3R,1'S)-3-(1'-N-t-butyloxycarbonyl-N-methylaminoethyl)-1-(R-α-methylbenzyl)pyrrolidin-5-one
(3S,1'R)-3-(1'-N-t-butyloxycarbonyl-N-methylaminoethyl)-1-(R-α-methylbenzyl)pyrrolidin-5-one
(3S,1'S)-3-(1'-N-t-butyloxycarbonyl-N-methylaminoethyl)-1-(R-α-methylbenzyl)pyrrolidin-5-one
(3R,1'R)-3-(1'-N-trifluoroacetyl-N-methylaminoethyl)-1-(S-α-methylbenzyl)pyrrolidin-5-one
(3R,1'S)-3-(1'-N-trifluoroacetyl-N-methylaminoethyl)-1-(S-α-methylbenzyl)pyrrolidin-5-one
(3S,1'R)-3-(1'-N-trifluoroacetyl-N-methylaminoethyl)-1-(S-α-methylbenzyl)pyrrolidin-5-one
(3S,1'S)-3-(1'-N-trifluoroacetyl-N-methylaminoethyl)-1-(S-α-methylbenzyl)pyrrolidin-5-one
(3R,1'R)-3-(1'-N-trifluoroacetyl-N-methylaminoethyl)-1-(R-α-methylbenzyl)pyrrolidin-5-one
(3R,1'S)-3-(1'-N-trifluoroacetyl-N-methylaminoethyl)-1-(R-α-methylbenzyl)pyrrolidin-5-one
(3S,1'R)-3-(1'-N-trifluoroacetyl-N-methylaminoethyl)-1-(R-α-methylbenzyl)pyrrolidin-5-one
(3S,1'S)-3-(1'-N-trifluoroacetyl-N-methylaminoethyl)-1-(R-(α-methylbenzyl)pyrrolidin-5-one
(3R,1'R)-3-(1'-N-trifluoroacetylaminoethyl)-1-(S-α-methylbenzyl)pyrrolidin-5-one
(3R,1'S)-3-(1'-N-trifluoroacetylaminoethyl)-1-(S-α-methylbenzyl)pyrrolidin-5-one
(3S,1'R)-3-(1'-N-trifluoroacetylaminoethyl)-1-(S-α-methylbenzyl)pyrrolidin-5-one
(3S,1'S)-3-(1'-N-trifluoroacetylaminoethyl)-1-(S-α-methylbenzyl)pyrrolidin-5-one
(3R,1'R)-3-(1'-N-trifluoroacetylaminoethyl)-1-(R-(α-methylbenzyl)pyrrolidin-5-one (3R,1'S)-3-(1'-N-trifluoroacetylaminoethyl)-1-(R-(α-methylbenzyl)pyrrolidin-5-one
(3S,1'R)-3-(1'-N-trifluoroacetylaminoethyl)-1-(R-(α-methylbenzyl)pyrrolidin-5-one
(3S,1'S)-3-(1'-N-trifluoroacetylaminoethyl)-1-(R-(α-methylbenzyl)pyrrolidin-5-one The final products and intermediates of the present invention may be prepared as detailed hereafter and as illustrated by the following schemes.

Scheme 1

Equation 1

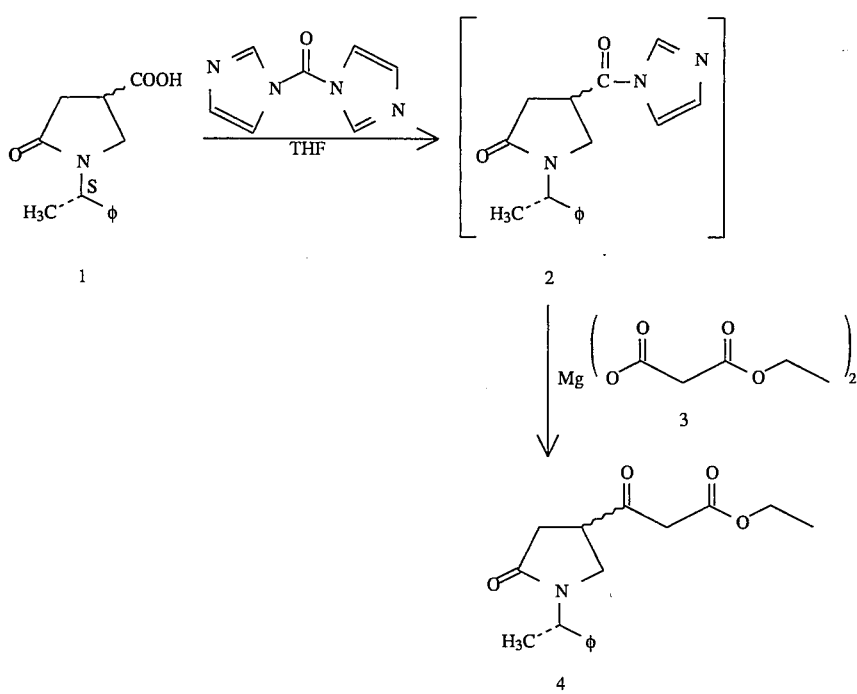

Equation 2

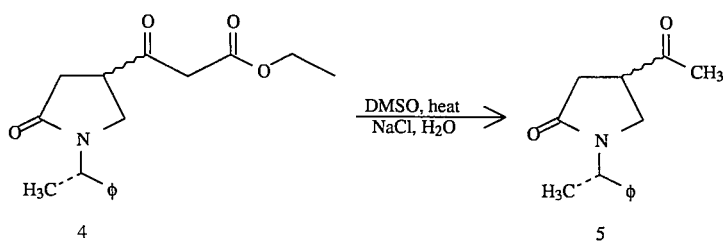

Equation 3

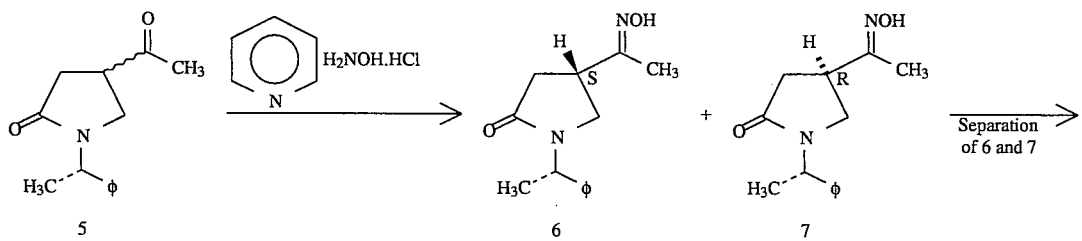

Equation 4

-continued
Scheme 1
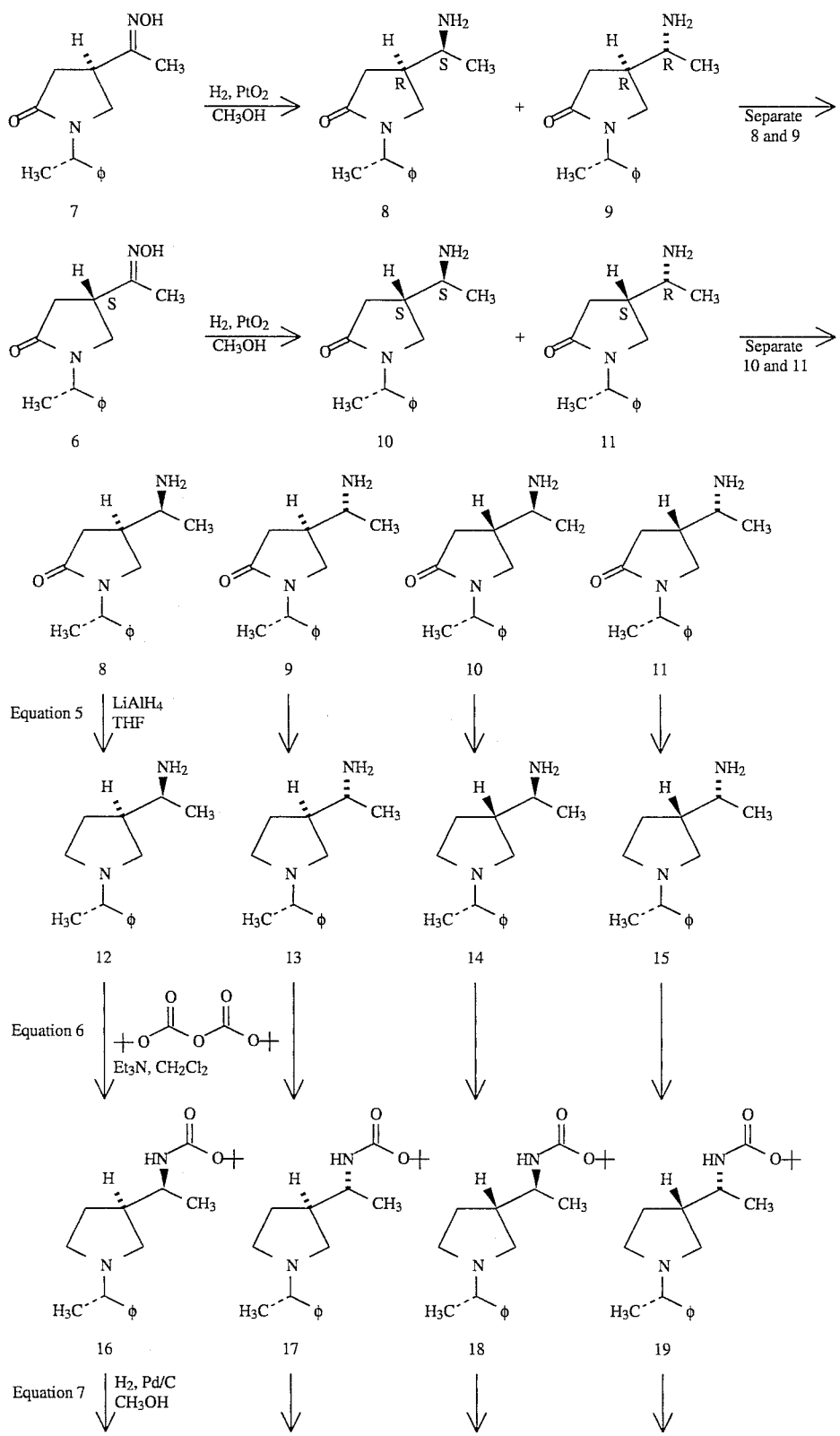

-continued
Scheme 1
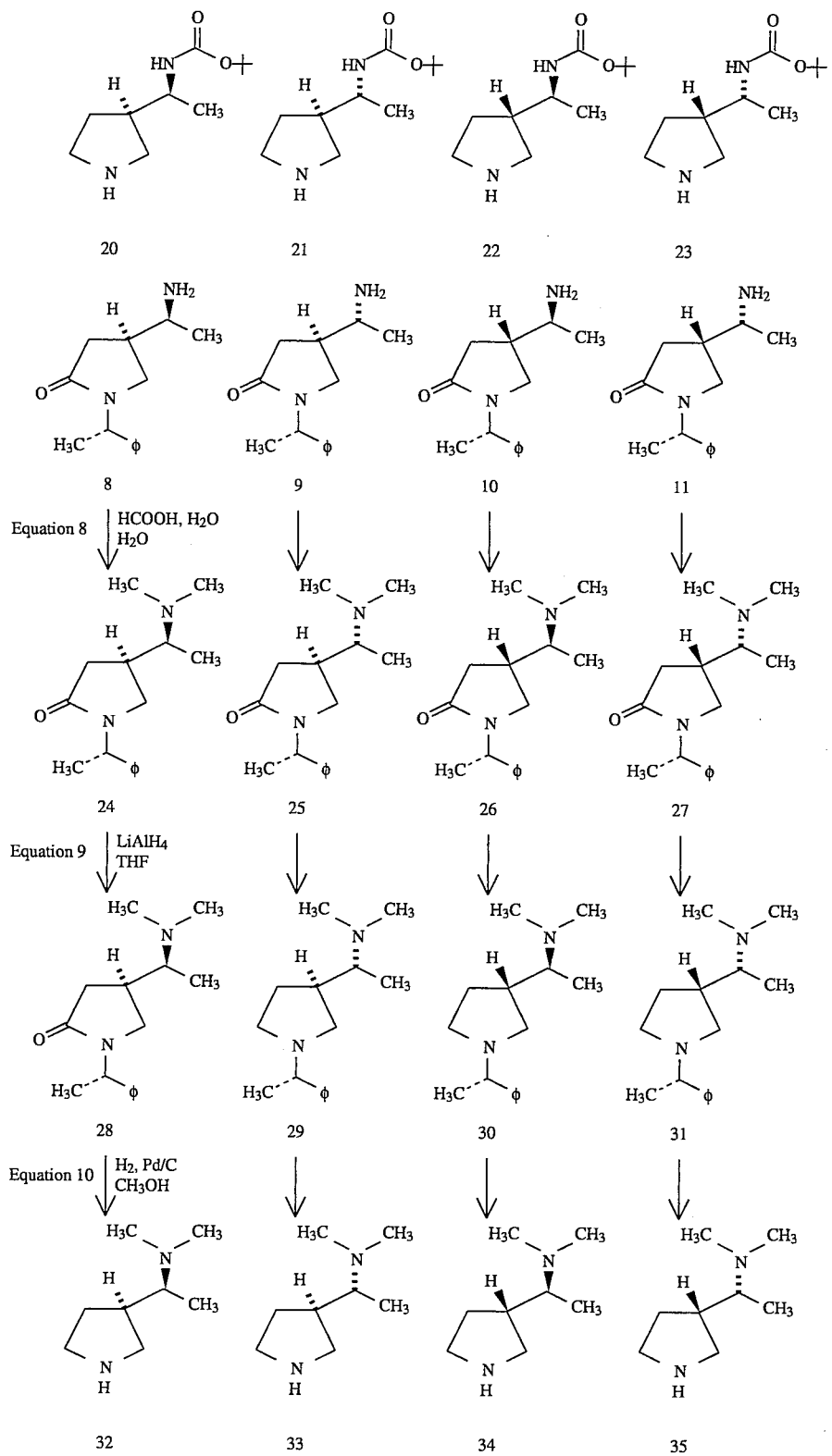

-continued
Scheme 1
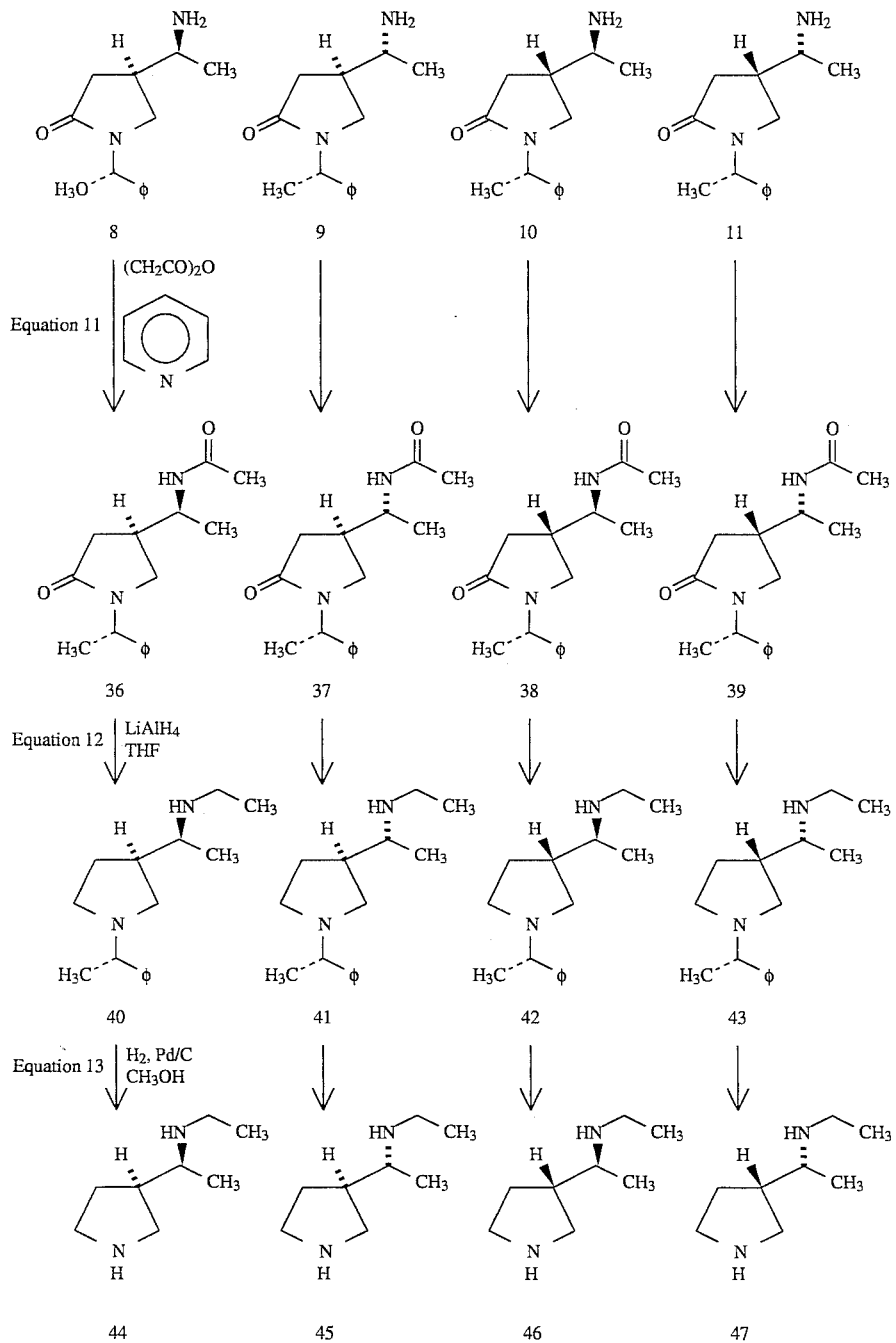

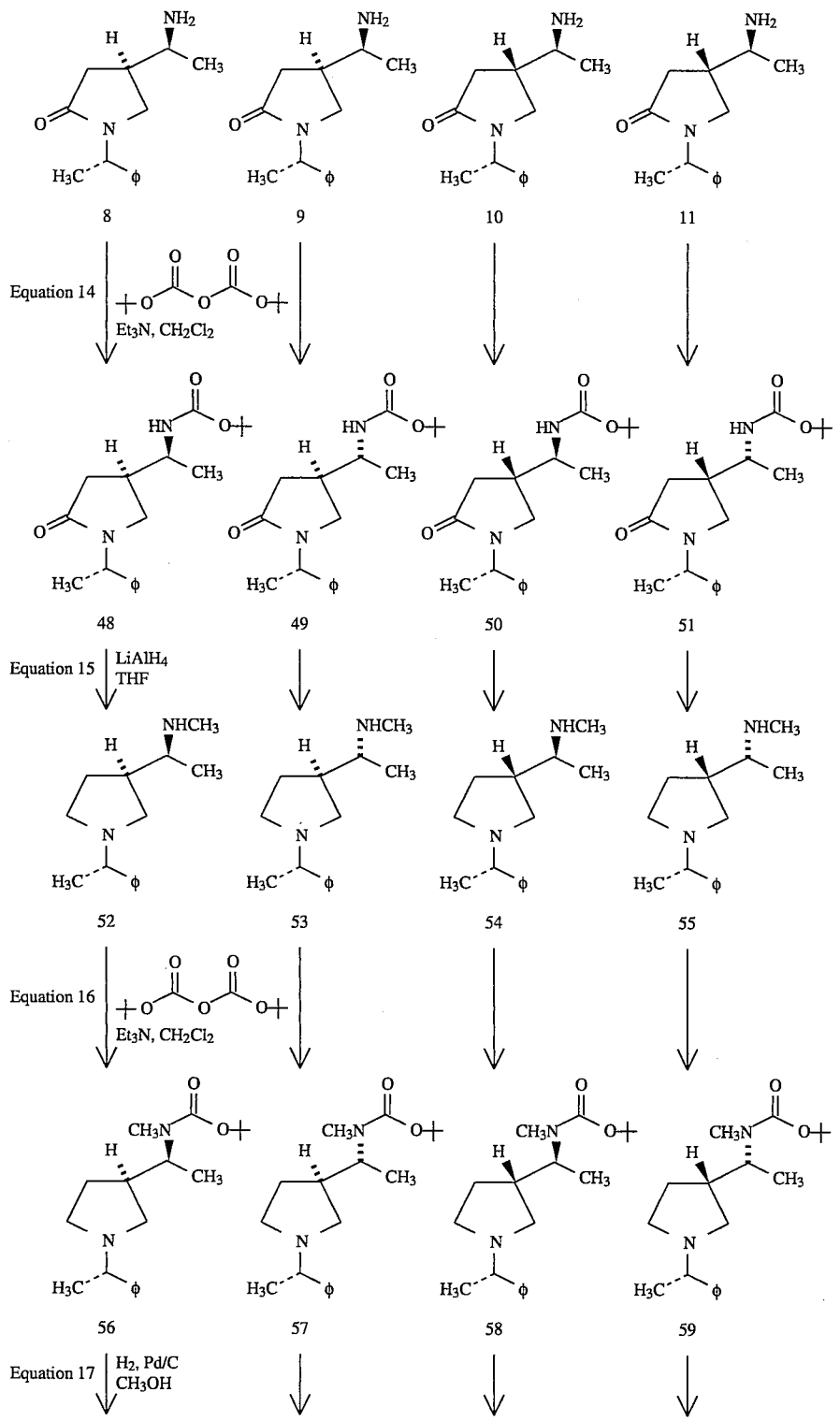

-continued
Scheme 1
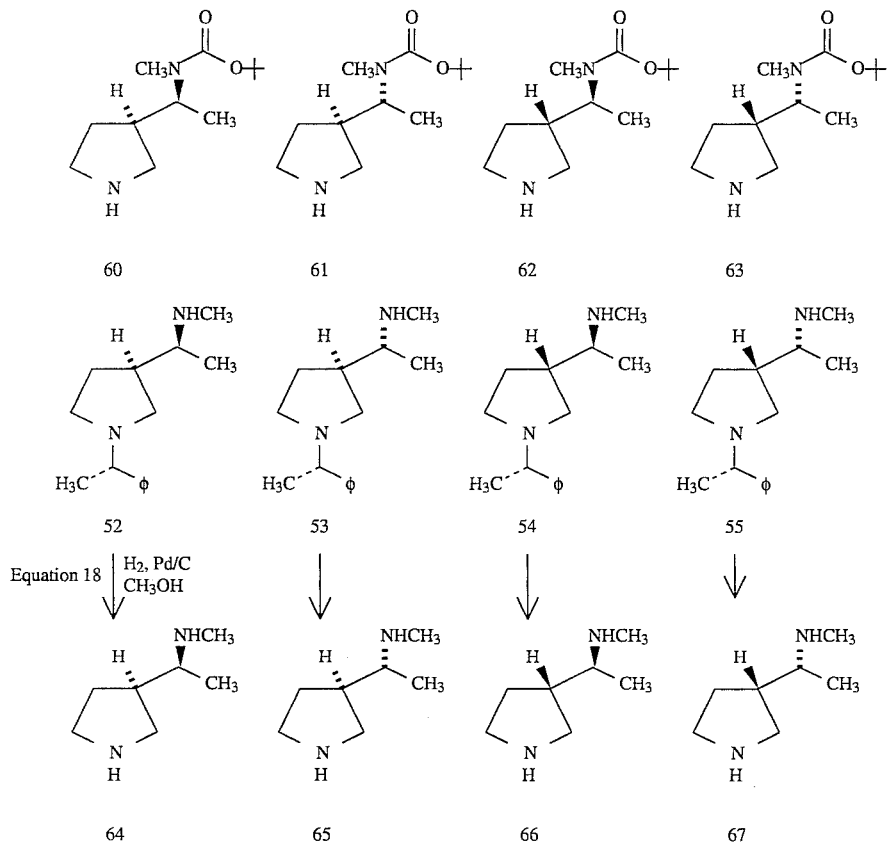
Equation 19
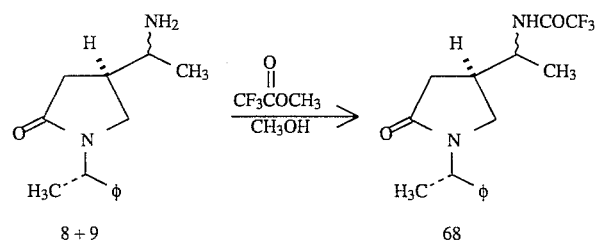
Equation 20
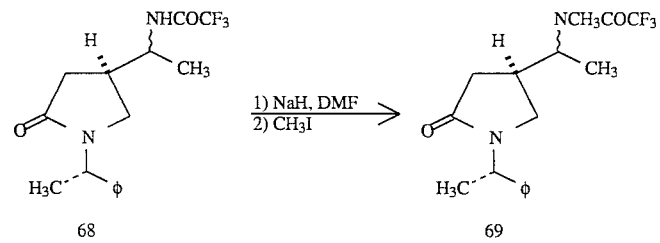

-continued
Scheme 1

Equation 21

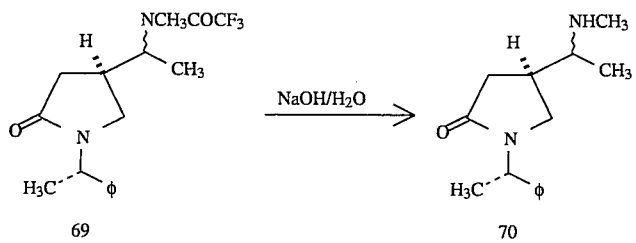

DETAILED DESCRIPTION

Starting from the previously prepared (J. Med. Chem., (1987), 30, 1711) 1-(S-α-methylbenzyl)-pyrrolidin- 5-one-3-carboxylic acid (1) conversion to an activated intermediate (2) is preferably done by reaction with carbonyl diimidazole in THF at 30°–50° C. for 18–30 hours, Equation 1. Alternative solvents include diethylether, dioxane and the like, chlorocarbon solvents, toluene or other aromatic solvents at room temperature to 100° C. for 1–72 hours. Alternative methods of carboxylic acid activation such as conversion to an acid chloride with thionyl chloride, phosphorus oxychloride, or the like or activation by conversion to a mixed anhydride with trifluoroacetic anhydride or the like are also suitable. The activated acid (2) is reacted in situ, preferably, or after isolation with an anion of diethylmalonate, preferably magnesium bis(ethylmalonate) (3) in THF at reflux temperature for 2–4 hours. The solvents employed above are also acceptable for this step at ambient temperatures to 150° C. The use of dilithio ethylmalonate, or the anion of diethylmalonate (cation=lithium, magnesium, sodium, calcium, or potassium) are also acceptable. In situ decarboxylation is accomplished next through the use of an aqueous workup or if desired an acidic workup to give 3-(2'-(ethoxycarbonyl)acetyl)-1-(S-α-methylbenzyl)pyrrolidin- 5-one (4). Acids useful for affecting decarboxylation are HCl, $H_2SO_4$, $H_3PO_4$ and the like, Equation 1.

This β-keto ester (4) is reacted preferably with sodium chloride in DMSO containing 100–1000 mol % water at 120°–220° C. to affect decarboxylation, preferably 200–400 mol % of NaCl at 103°–140° C. for 18–24 hours, giving 3-(acetyl)-1-(S-α-methylbenzyl)pyrrolidin-5-one (5), Equation 2.

The methyl ketone (5) was converted to 3-(1' -hydroxyiminoethyl)-1-(S-α-methylbenzyl)pyrrolidin-5 -one (6 and 7) via reaction with hydroxylamine hydrochloride in a suitable solvent at ambient temperature to 100° C. Preferably this is performed in ethanol/water at 40° C. to ambient temperature. Solvents such as pyridine, THF, and other alcohol solvents are also useful for the preparation of the oxime. The oxime (6 and 7) is separated into its individual diastereomers (6) and (7) by column chromatography on silica gel (70–230 or 230–400 mesh) using ethyl acetate, ethyl acetate-saturated hydrocarbon solvent, such as pentane, hexane, heptane, and isooctane. Final purification is through recrystallization of the purified diastereomers 3S-3 -(1'-hydroxyiminoethyl)-1-(S-α-methylbenzyl)pyrrolidin-5-one (6) and 3R-3-(1'RS-hydroxyiminoethyl)-1-(S-α -methylbenzyl)pyrrolidin-5-one (7) from ethyl acetate or a like solvent.

The individual oxime (7) is reduced to the primary amines, (3R,1RS)-3-(1'-aminoethyl)-1 -methylbenzyl)pyrrolidin-5-one (8 and 9) through the use of catalytic hydrogenation with hydrogen gas (Equation 4) or a hydrogen source such as ammonium formate, cyclohexene, or cyclohexadiene. The preferred catalysts being platinum oxide, varying percentages of rhodium on an inert support such as carbon, alumina, or Raney-nickel, or the like, in solvents such as methanol, ethanol, THF, ethyl acetate and the like at ambient temperatures to 40°–60° C., preferably at room temperature. The reduction produced a set of diastereomers (8 and 9) which were separated by column chromatography on silica gel (70–230 or 230–400 mesh) using a chlorocarbon solvent containing varying concentrations of a tertiary amine and an alcohol, preferably chloroform-triethylamine-ethanol giving 3R,1'S-3-(1'-aminoethyl)-1-(S-α-methylbenzyl)pyrrolidin-5-one (8) and 3R,1'R-3-(1' -aminoethyl)-1-(S-α-methylbenzyl)pyrrolidin-5-one (9), (Equation 4).

Likewise the oxime (6) could be reduced to give 3S,1'RS-(1'-aminoethyl)-1 -(S-α-methylbenzyl)-2pyrrolidin-5-one (10 and 11), Equation 4.

The individual diastereomeric pyrrolidone amines (8, 9, 10, 11) were reduced to the pyrrolidines through the action of a hydride reducing agent in an inert solvent at an elevated temperature, usually lithium aluminum hydride in an ether solvent such as THF at 50°–66° C. or the like, Equation 5. The primary amines (12, 13, 14, 15) individually were each protected as the t-butylcarbamate by reaction of the amine with a t-butyloxycarbonyl transfer reagent such as di-t-butylcarbonate and the like, Equation 6, giving 16, 17, 18, 19.

The BOC-protected aminoethylpyrrolidine (16–19) were subjected to varying de-α-methylbenzylations via hydrogenolysis using varying percentages of palladium on a inert support such as carbon, alumina, silica, or the like, preferably 20% palladium on carbon in an inert solvent such as methanol, ethanol, THF, or ethyl acetate. This provides the individual diastereomeric 3-(1'-aminoethyl)pyrrolidines (20, 21, 22, 23), (Equation 7) in a protected form suitable for coupling with a quinolone or naphthyridone substrate.

The individual 3-(1'-N,N-dimethylaminoethyl) pyrrolidines (32, 33, 34, 35) could be prepared by reacting the amine (8, 9, 10, 11) with paraformaldehyde in formic acid at an elevated temperature, preferably employing aqueous solutions of formaldehyde (20–80%, usually 35%) and aqueous formic acid (50–90%, usually 88%) beginning at 0°–5° C. and continuing at reflux temperature for 2–10 hours (preferably five hours). This provides the individual diastereomeric N,N-dimethylamines (24, 25, 26, 27), Equation 8. The carbonyl function of 24–27 was removed by reducing the pyrrolidin-5-one with a hydride reducing agent in an inert solvent. The preferred method was with lithium aluminum hydride in THF at reflux for 12–24 hours giving the pyrrolidines 28, 29, 30, 31, Equation 9. The 3-(1' -N,N-dimethylaminoethyl)pyrrolidines (28–31) were de-α-methylbenzylated via hydrogenolysis using varying percentages of palladium on a inert support such as carbon, alumina, silica, or the like, preferably 20% palladium on carbon in an inert solvent such as methanol, ethanol, THF, or ethyl acetate. This provides the individual diastereomeric 3-(1'-N,N-dimethylaminoethyl)pyrrolidines, 32, 33, 34, 35, (Equation 10) in a form suitable for coupling with a quinolone or naphthyridone substrate.

The 3-(1'-N-ethylaminoethyl)pyrrolidines (44, 45, 46, 47) were prepared by reacting the amines (8, 9, 10, 11) with an acetyl transfer agent such as acetic anhydride or acetyl chloride or the like in the presence of an acid scavenger such as a tertiary amine including pyridine, lutidine, triethylamine and the like either with or without an inert solvent such as an ether or chlorocarbon in a temperature range of room temperature to the reflux temperature of the reaction mixture for 6–72 hours, preferable in acetic anhydride-pyridine 4/1 at ambient temperature for 12–24 hours to give the 3-(N-acetyl-1' -aminoethyl)pyrrolidin-5-ones, 36, 37, 38, 39, Equation 11. The two amide functions of 36–39 were reduced by reacting the pyrrolidin-5-one with a hydride reducing agent in an inert solvent. The preferred method was with lithium aluminum hydride in THF at reflux for 12–24 hours giving the individual diastereomeric pyrrolidines, 40, 41, 42, 43, Equation 12. The individual diastereomeric 3-(1'-N-ethylaminoethyl) -(1-α -methylbenzyl)pyrrolidines (40–43) were de-α-methylbenzylated via hydrogenolysis using varying percentages of palladium on an inert support such as carbon, alumina, silica, or the like, preferably 20% palladium on carbon in an inert solvent such as methanol, ethanol, THF, or ethyl acetate. This provides the individual 3-(1'-N-ethylaminoethyl)pyrrolidines, 44, 45, 46, 47, (Equation 13) in a form suitable for coupling with a quinolone or naphthyridone substrate.

The 3-(N-t-butyloxycarbonyl-1'-N-methylaminoethyl)pyrrolidines (60, 61, 62, 63) were prepared by reacting the amines (8–11) with a t-butyloxycarbonyl transfer agent such as di-t-butylcarbonate or t-butyloxycarbonyl chloride or the like in the presence of an acid scavenger such as a tertiary amine including pyridine, lutidine, triethylamine and the like either with or without an inert solvent such as an ether or chlorocarbon in a temperature range of room temperature to the reflux temperature of the reaction mixture for 6–72 hours, preferable in dichloromethane and di-t-butylcarbonate at ambient temperature for 12–24 hours to give the 3 -(N-t-butyloxycarbonyl-1'-aminoethyl)-1-(S-α -methylbenzyl)pyrrolidin-5-ones, 48, 49, 50, 51, Equation 14. The two amides were removed by reacting the pyrrolidin-5-ones (48–51) with a hydride reducing agent in an inert solvent. The preferred method was with lithium aluminum hydride in THF at reflux for 12–24 hours giving the individual diastereomeric pyrrolidines, 52, 53, 54, 55, Equation 15. The reduced pyrrolidines, 52–55, could be protected by reacting the 3-N-methyl-1'-aminomethyl moiety with a t-butyloxycarbonyl transfer agent such as di-t-butylcarbonate or t-butyloxycarbonyl chloride or the like in the presence of an acid scavenger such as a tertiary amine including pyridine, lutidine, triethylamine and the like either with or without an inert solvent such as an ether or chlorocarbon in a temperature range of room temperature to the reflux temperature of the reaction mixture for 6–72 hours, preferably in dichloromethane and di-t-butyldicarbonate at ambient temperature for 12–24 hours to give the 1-(α-methylbenzyl)-3-(N-t-butyloxycarbonyl- 1'-N-methylaminoethyl)pyrrolidines, 56, 57, 58, 59, Equation 16. The 3-(N-t-butyloxycarbonyl- 1'-N-methylaminoethyl)pyrrolidines, 56–59 were de-α-methylbenzylated via hydrogenolysis using varying percentages of palladium on an inert support such as carbon, alumina, silica, or the like, preferably 20% palladium on carbon in an inert solvent such as methanol, ethanol, THF, or ethyl acetate. This provides the 3-(1'-N-t-butoxycarbonyl-1 '-N-methylaminoethyl)pyrrolidines, 60, 61, 62, 63 (Equation 17) in a form suitable for coupling with a quinolone or naphthyridone nucleus.

The 3-(1'-N-methylaminoethyl)pyrrolidines, 64–67, were prepared by the de-α-methylbenzylation, via hydrogenolysis using varying percentages of palladium on an inert support such as carbon, alumina, silica, or the like, preferably 20% palladium on carbon in an inert solvent such as methanol, ethanol, THF, or ethyl acetate, of the pyrrolidines, 52, 53, 54, 55, Equation 18. This provides the individual diastereomers 64, 65, 66, 67, 3-(1'-N-methylaminoethyl)pyrrolidines (Equation 18) in a form suitable for coupling with a quinolone or naphthyridone substrate.

Alternatively, the 3-(1'-aminoethyl)pyrrolidin-5 -one (8 and 9) were reacted with methyl trifluoroacetate in an inert solvent or alternatively with trifluoroacetic anhydride in the presence of an acid acceptor such as triethylamine or pyridine or the like at 0° C. to ambient temperature to give the 3-(N-trifluoroacetyl-1'-aminoethyl)pyrrolidin-5-ones, 68, Equation 19. These compounds were reacted with a hydrogen abstractor such as sodium hydride or a similar agent in an ether solvent such as THF followed by addition of a methylating agent like methyliodide to give the 3-(N-methyl-N-trifluoroacetyl-1' -aminoethyl)pyrrolidin-5-one, 69, Equation 20. The trifluoroacetyl group could be removed by hydrolysis using aqueous hydroxide, Equation 21. The resulting compounds 70 could be reduced as described above.

The pyrrolidines prepared could be coupled to the appropriate quinolone or naphthyridone substrate by published procedures including; Domagala, et al., *J. Medicinal Chemistry*, 31, 503 (1988), Sanchez, et al., *J. Medicinal Chemistry*, 31, 983, (1988), Itawa, et al., European Patent Application 8702813.8 1987, and British Patent 2,011,395A.

A representative group of quinolones is shown in FIG. 1.

FIG. 1

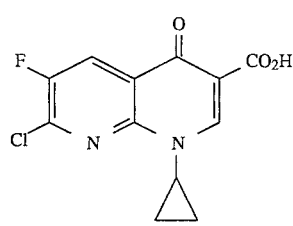

A

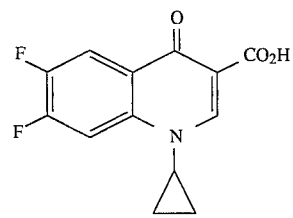

B

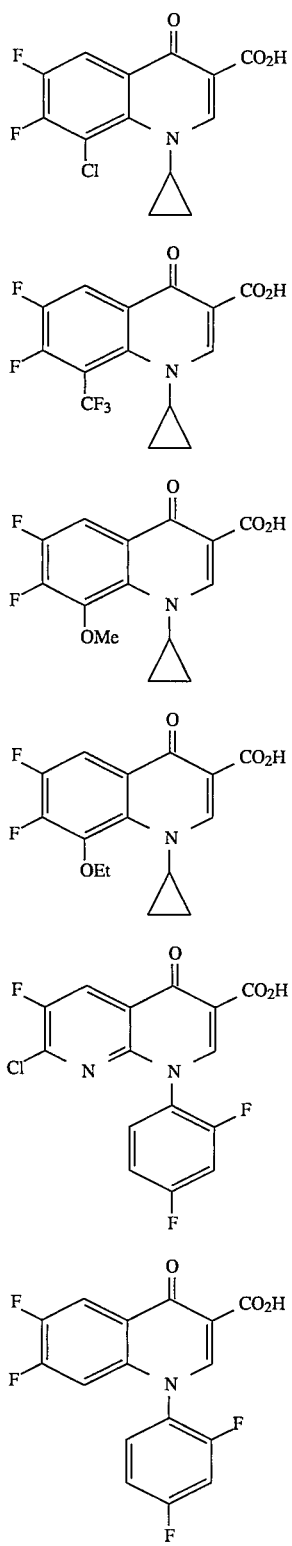
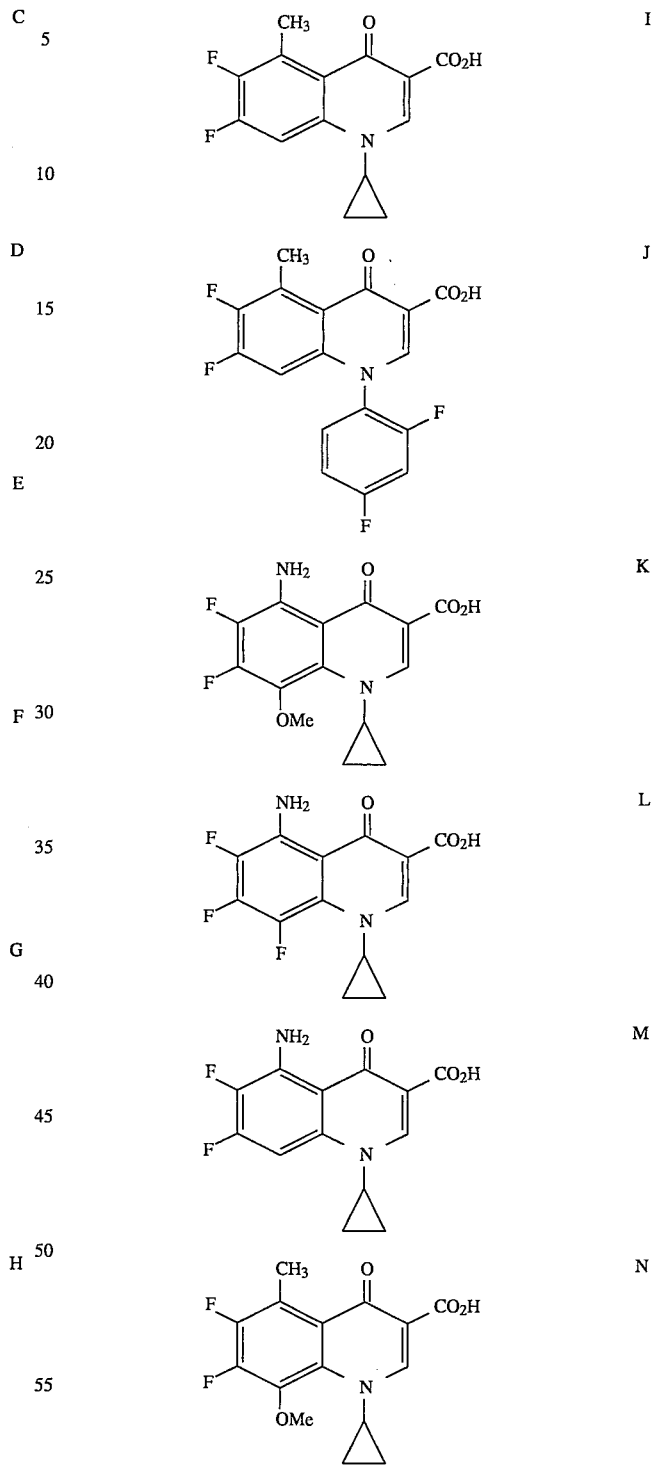
The enantiomeric quinolones and naphthyridones of the invention display potent antibacterial activity against gram negative and especially gram positive organisms both in vitro as well as in vivo. Their overall therapeutic advantages are also shown by including phototoxicity and cytotoxicity data as compared to compounds described in European Patent Publication 207,420.

The in vitro antibacterial activity, is obtained by the microtitration dilution method as described in Heifetz, et al., *Antimicr. Agents & Chemother.*, 6, 124 (1974), which is incorporated herein by reference.

The in vivo activity is obtained when the compounds are tested according to the procedure of Miller, et al (Proc. Soc. Exp. Biol. Med. 57, 261, 1944). The median protective dose (PD50) was determined in mice given lethal systemic infections. Single doses of compound were given at time of challenge.

The phototoxicity data is obtained using depilated mice. The compound was administered orally each day for four successive days, followed each day by 3 hours of UVA radiation. The mice were examined for any positive signs (redness, erythema) relative to control animals. The no effect dose and the 50% effect dose were determined.

The cytotoxicity data is obtained using hamster V-79 cells. The cells were suspended in tissue culture medium and grown overnight. Cells were treated with drug for 3 hours, washed free of drug and then replated, and the colonies counted after 5 days. The concentration of drug that reduced colones by 50% relative to control was recorded.

By use of the above methods, the following minimum inhibiting concentration values (MICs in μg/mL), $PD_{50}$'s in mg/kg, no effect phototoxicity dose in mg/kg and the cytotoxicity $IC_{50}$ in μg/mL were obtained for representative enantiomers of the invention and compounds of the prior art as shown in the table.

The in vivo data as $PD_{50}$s are reported below the line of MICs for the same compound.

| Example Number | | Ent. cloacae MA2646 | Esch. coli Vogel | Klebs. pneumoniae MGH-2 | Prot. rettgeri M 1771 | Pseud. aeruginosa UI-18 | Staph. aureus H 228 | Staph. aureus UC-76 | Strep. faecalis MGH-2 | Strep. pneumoniae SV-1 | Strep. pyogenes C-203 | Photo NED mg/kg | Cytotox µg/mL |
|---|---|---|---|---|---|---|---|---|---|---|---|---|---|
| 2 | PO | 0.2 | 0.2 | 0.4 | 0.8 | 1.6 | 0.8 | 0.1 | 0.4 | 0.2 | 0.1 | | 160 |
|  | SC |  | 100 |  |  |  |  |  |  | >100 |  |  |  |
|  |  |  | 4 |  |  |  |  |  |  | 12 |  |  |  |
| 1 | PO | 0.2 | 0.2 | 0.4 | 0.8 | 1.6 | 0.4 | 0.05 | 0.2 | 0.1 | 0.1 | | 160 |
|  | SC |  | 35 |  |  |  |  |  |  | >100 |  |  |  |
|  |  |  | 2 |  |  |  |  |  |  | 3 |  |  |  |
| 3 | PO | 0.05 | 0.05 | 0.1 | 0.2 | 0.4 | 0.05 | 0.003 | 0.025 | 0.003 | 0.003 | | 42 |
|  | SC |  | 4.7 |  |  |  |  |  |  | 11 |  |  |  |
|  |  |  | 0.9 |  |  |  |  |  |  | 0.7 |  |  |  |
| 4 | PO | 0.2 | 0.1 | 0.4 | 0.8 | 1.6 | 0.2 | 0.05 | 0.1 | 0.025 | 0.1 | | 140 |
|  | SC |  | 72 |  |  |  |  |  |  | 105 |  |  |  |
|  |  |  | 2 |  |  |  |  |  |  | 2 |  |  |  |
| Enantiomer Mixture (Mixture B) | | | | | | | | | | | | | |
| 5 | PO | 0.1 | 0.05 | 0.2 | 0.4 | 0.8 | 0.1 | 0.013 | 0.05 | 0.006 | 0.006 | | 60 |
|  | SC |  | 29 |  |  | 23 |  |  |  | 12 |  |  |  |
|  |  |  | 2 |  |  | 16 |  |  |  | 1 |  |  |  |
| 6 | PO | 0.05 | 0.05 | 0.1 | 0.2 | 1.6 | 0.2 | 0.025 | 0.1 | 0.05 | 0.05 | >100 | 84 |
|  | SC |  | 4 |  |  | 96 |  |  |  | 15 |  |  |  |
|  |  |  | 1 |  |  | 25 |  |  |  | 7 |  |  |  |
| 7 | PO | 0.05 | 0.05 | 0.2 | 0.4 | 1.6 | 0.2 | 0.025 | 0.1 | 0.05 | 0.05 | >100 | 77 |
|  | SC |  | 8 |  |  | 0.4 |  |  |  | 28 |  |  |  |
|  |  |  | 1 |  |  | 15 |  |  |  | 10 |  |  |  |
| 7 | PO | 0.025 | 0.025 | 0.05 | 0.1 | 0.4 | 0.025 | 0.03 | 0.025 | 0.006 | 0.013 | 30 | 33 |
|  | SC |  | 2 |  |  | 4 |  |  |  | 3 | 3 |  |  |
|  |  |  | 0.4 |  |  |  |  |  |  | 1 | 1 |  |  |
| 8 | PO | 0.05 | 0.05 | 0.1 | 0.4 | 0.8 | 0.05 | 0.06 | 0.05 | 0.006 | 0.013 | 55 | 100 |
|  | SC |  | 6 |  |  | 35 |  |  |  | 14 |  |  |  |
|  |  |  | 1 |  |  | 12 |  |  |  | 2 |  |  |  |
|  | PO SC | 0.05 | 0.02520.80.1 | 0.02520.80.1 | 0.2 | 0.8166 | 0.05 | 0.006 | 0.05 | 0.01352 | 0.01341 | 55 | 48 |

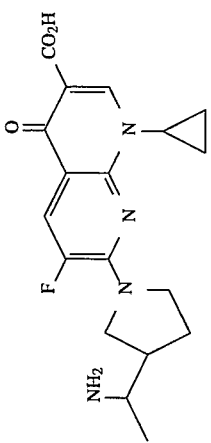

Enantiomeric Mixture (Mixture B)
Reference Example 5
EPO 207420 (Mixture C)

| | | | | | | | | | | | | | |
|---|---|---|---|---|---|---|---|---|---|---|---|---|---|
| 24 | PO | 0.4 | 0.05 | 0.2 | | | | 0.013 | 0.05 | 0.013 | 0.05 | | 150 |
|  | SC | 0.4 | 9 |  |  |  |  |  |  |  |  |  |  |
| 23 | PO | 0.1 | 0.2 | 0.4 | 0.8 | 3.1 | 0.8 | 0.2 | 0.8 | 0.4 | 0.4 | | |
|  | SC | 0.1 | 0.1 | 0.2 | 0.8 | 1.6 | 0.2 | 0.05 | 0.2 | 0.1 | 0.1 | | |
| 21 | | 0.1 | 0.1 | 0.2 | 0.4 | 1.6 | 0.05 | 0.0013 | 0.05 | 0.013 | 0.025 | | 130 |

-continued

| Example Number | | Ent. cloacae MA2646 | Esch. coli Vogel | Klebs. pneumoniae MGH-2 | Prot. rettgeri M 1771 | Pseud. aeruginosa UI-18 | Staph. aureus H 228 | Staph. aureus UC-76 | Strep. faecalis MGH-2 | Strep. pneumoniae SV-1 | Strep. pyogenes C-203 | Photo NED mg/kg | Cytotox µg/mL |
|---|---|---|---|---|---|---|---|---|---|---|---|---|---|
| 22 | PO | | 1.0 | | | | | | | | 2 | | |
|  | SC | | 0.5 | | | | | | | | 2 | | |
|  |  | 0.1 | 0.1 | 0.2 | 0.4 | 1.6 | 0.1 | 0.05 | 0.025 | 0.05 | 0.05 | | 88 |
|  | PO | | 4.6 | | | | | | | | 8 | | |
|  | SC | | 1.2 | | | | | | | | 5 | | |
|  | 0.05POSC | 0.0541 | | | | | | | | | 0.1116 | 140 | |
|  |  | 0.05 | | 0.1 | 0.8 | 1.6 | 0.1 | 0.025 | 0.1 | 0.05 | | | |

Enantiomer Mixture
(Mixture B)

Structure: quinolone with CO₂H, F, cyclopropyl N, and NHMe-substituted pyrrolidine

| Example Number | | Ent. cloacae MA2646 | Esch. coli Vogel | Klebs. pneumoniae MGH-2 | Prot. rettgeri M 1771 | Pseud. aeruginosa UI-18 | Staph. aureus H 228 | Staph. aureus UC-76 | Strep. faecalis MGH-2 | Strep. pneumoniae SV-1 | Strep. pyogenes C-203 | Photo NED mg/kg | Cytotox µg/mL |
|---|---|---|---|---|---|---|---|---|---|---|---|---|---|
| 42 |  | 0.025 | 0.025 | 0.05 | 0.1 | 0.8 | 0.006 | 0.003 | 0.013 | 0.006 | 0.006 | <30 | 11 |
|  | PO |  | 3 |  |  |  |  |  |  |  | 0.55 |  |  |
|  | SC |  | 0.4 |  |  |  |  |  |  |  | 0.25 |  |  |
| 41 |  | 0.05 | 0.05 | 0.1 | 0.2 | 0.8 | 0.006 | 0.003 | 0.013 | 0.006 | 0.006 | 30 | 33 |
|  | PO |  | 3 |  |  |  |  |  |  |  | 2 |  |  |
|  | SC |  | 2 |  |  |  |  |  |  |  | 0.7 |  |  |
| 81 |  | 0.8 | 0.4 | 0.8 | 3.1 | 6.3 | 0.8 | 0.4 | 0.8 | 0.2 | 0.4 |  |  |
| 80 |  | 0.2 | 0.2 | 0.4 | 1.6 | 3.1 | 0.2 | 0.1 | 0.2 | 0.1 | 0.4 |  |  |
| 79 |  | 0.1 | 0.1 | 0.2 | 0.8 | 1.6 | 0.1 | 0.025 | 0.05 | 0.025 | 0.05 |  |  |
| 78 |  | 0.4 | 0.1 | 0.2 | 1.6 | 1.6 | 0.05 | 0.025 | 0.05 | 0.025 | 0.05 |  |  |
|  | PO |  | 2 |  |  |  |  |  |  |  | 6 |  |  |
|  | SC |  | 1 |  |  |  |  |  |  |  | 4 |  |  |
| 20 |  | 0.4 | 0.8 | 1.6 | 3.1 | 6.3 | 0.2 | 0.05 | 0.4 | 0.2 | 0.2 |  |  |
| 19 |  | 0.1 | 0.4 | 0.8 | 1.6 | 6.3 | 0.1 | 0.05 | 0.1 | 0.013 | 0.025 |  |  |
| 18 |  | 0.1 | 0.1 | 0.2 | 0.4 | 3.1 | 0.013 | 0.003 | 0.025 | 0.006 | 0.006 | >100 | 110 |
|  | PO |  | 5 |  |  |  |  |  |  |  | 0.5 |  |  |
|  | SC |  | 2 |  |  |  |  |  |  |  | 0.2 |  |  |
| 17 |  | 0.2 | 0.2 | 0.4 | 0.8 | 3.1 | 0.013 | 0.003 | 0.013 | 0.003 | 0.003 | >100 | 130 |
|  | PO |  | 14 |  |  |  |  |  |  |  | 2 |  |  |
|  | SC |  | 4 |  |  |  |  |  |  |  | 0.6 |  |  |
| 36 |  | 0.05 | 0.05 | 0.1 | 0.2 | 0.8 | 0.013 | 0.013 | 0.025 | 0.013 | 0.003 | >100 | 33 |
|  | PO |  | 4 |  |  |  |  |  |  |  | 1 |  |  |
| 38 |  | 0.2 | 0.2 | 0.4 | 0.8 | 3.1 | 0.05 | 0.013 | 0.05 | 0.025 | 0.1 | — | 130 |
|  | SC |  | 1 |  |  |  |  |  |  |  | 0.025 |  |  |
| 44 |  | 0.05 | 0.025 | 0.05 | 0.05 | 0.4 | 0.006 | ≦0.003 | 0.006 | ≦0.003 | ≦0.003 |  |  |

-continued

| Example Number | | Ent. cloacae MA2646 | Esch. coli Vogel | Klebs. pneumoniae MGH-2 | Prot. rettgeri M 1771 | Pseud. aeruginosa UI-18 | Staph. aureus H 228 | Staph. aureus UC-76 | Strep. faecalis MGH-2 | Strep. pneumoniae SV-1 | Strep. pyogenes C-203 | Photo NED mg/kg | Cytotox µg/mL |
|---|---|---|---|---|---|---|---|---|---|---|---|---|---|
| 45 | | 0.05 | 0.05 | 0.1 | 0.2 | 0.8 | 0.25 | ≤0.03 | 0.025 | 0.013 | 0.013 | | |
| 46 | | 0.2 | 0.2 | 0.4 | 0.4 | 1.6 | 0.025 | 0.013 | 0.1 | 0.013 | 0.013 | | |
| 47 | | 0.1 | 0.1 | 0.1 | 0.2 | 0.0 | 0.025 | 0.003 | 0.025 | 0.003 | 0.003 | | |
| 48 | | 0.1 | 0.1 | 0.2 | 0.4 | 1.6 | 0.1 | 0.025 | 0.1 | 0.05 | 0.05 | | |
| | PO | | | | | | | | | 9 | | | |
| | SC | | | | | | | | | 3 | | | |
| 49 | | 0.2 | 0.1 | 0.2 | 0.2 | 1.6 | 0.013 | ≤0.003 | 0.025 | 0.006 | 0.006 | | |
| 43 | | 0.2 | 0.1 | 0.2 | 0.4 | 0.8 | 0.05 | 0.006 | 0.025 | 0.006 | 0.006 | >100 | 280 |
| | PO | 3.5 | 3.5 | | | | | | | 3 | 1 | | |
| | SC | 1 | 1 | | | | | | | 3 | 1 | | |
| 50 | | 0.8 | 0.4 | 0.8 | 1.6 | 3.1 | 0.05 | 0.013 | 0.2 | 0.1 | 0.1 | | |
| | PO | | | | | | | | | 2 | | | |
| | SC | | | | | | | | | 2 | | | |
| 51 | | 0.8 | 0.8 | 1.6 | 3.1 | >3.1 | 0.2 | 0.05 | 0.4 | 0.2 | 0.2 | | |
| 52 | | 0.4 | 0.4 | 0.4 | 1.6 | 3.1 | 0.05 | 0.013 | 0.05 | 0.05 | 0.05 | | |
| 53 | | 0.025 | 0.025 | 0.05 | 0.1 | 0.8 | ≤0.003 | ≤0.003 | 0.013 | ≤0.003 | ≤0.003 | — | |
| | PO | | 1.6 | | | | | | | | 0.3 | | |
| | SC | | 0.8 | | | | | | | | 0.3 | | |
| 54 | | 0.4 | 0.4 | 0.8 | 1.6 | 3.1 | 0.025 | 0.013 | 0.1 | 0.013 | 0.013 | | |
| 55 | | 0.1 | 0.1 | 0.2 | 0.8 | 1.6 | 0.05 | 0.025 | 0.05 | 0.013 | 0.013 | | |
| 56 | | 0.2 | 0.2 | 0.4 | 0.4 | 1.6 | 0.013 | 0.006 | 0.025 | 0.006 | 0.006 | | |
| 57 | | 0.4 | 0.4 | 0.4 | 0.8 | 3.1 | 0.003 | 0.013 | 0.05 | 0.025 | 0.025 | | 220 |
| 58 | | 0.013 | 0.013 | 0.013 | 0.025 | 0.4 | 0.003 | 0.003 | 0.003 | 0.003 | 0.003 | | |
| 59 | | 0.05 | 0.05 | 0.1 | 0.1 | 0.8 | 0.006 | 0.003 | 0.006 | 0.006 | 0.006 | | |
| 60 | | 0.2 | 0.2 | 0.2 | 0.4 | 1.6 | 0.013 | ≤0.003 | 0.025 | ≤0.003 | ≤0.003 | | |
| 61 | | 0.1 | 0.1 | 0.2 | 0.4 | 1.6 | 0.006 | 0.4 | 1.6 | 0.8 | 1.6 | | |
| 34 | | 0.4 | 0.4 | 0.8 | 1.6 | 3.1 | 0.8 | 0.05 | 1.6 | 0.2 | 0.2 | | |
| 35 | | 0.2 | 0.4 | 0.8 | 0.8 | 3.1 | 0.1 | 0.05 | 0.2 | 0.2 | 0.2 | | |
| 63 | | 0.4 | 0.4 | 0.4 | 1.6 | 3.1 | 0.1 | 0.05 | 0.2 | 0.2 | 0.2 | | |
| 64 | | 0.8 | 0.4 | 0.8 | 1.6 | 3.1 | 0.1 | 0.025 | 0.2 | 0.025 | 0.05 | | 310 |
| | PO | | 5 | | | | | | | | 4 | | |
| | SC | | 2 | | | | | | | | 2 | | |
| 65 | | 0.1 | 0.1 | 0.2 | 0.4 | 0.8 | 0.013 | 0.006 | 0.025 | 0.003 | 0.003 | | 10 |
| | PO | | | | | | | | | | 5 | | |
| | SC | | | | | | | | | | 0.6 | | |
| 67 | | 0.4 | 0.4 | 0.8 | 1.6 | 3.1 | 0.05 | 0.013 | 0.1 | 0.013 | 0.025 | | |
| | PO | | | | | | | | | | 29 | | |
| | SC | | | | | | | | | | 3 | | |
| 69 | | 0.1 | 0.1 | 0.2 | 0.4 | 1.6 | 0.05 | 0.006 | 0.025 | 0.013 | 0.025 | | |
| 70 | | 0.4 | 0.4 | 0.8 | 3.1 | 12.5 | 0.4 | 0.2 | 0.8 | 0.2 | 0.4 | | |
| 72 | | 0.2 | 0.1 | 0.2 | 0.8 | 1.6 | 0.025 | 0.025 | 0.1 | 0.025 | 0.05 | <30 | 120 |
| | PO | 1 | 1 | | | 17 | | | | 2 | 2 | | |
| | SC | 1 | 1 | | | 11 | | | | 2 | 2 | | |
| 73 | | 0.2 | 0.1 | 0.2 | 0.8 | 1.6 | 0.1 | 0.05 | 0.1 | 0.05 | 0.05 | <30 | |
| | PO | 5 | 5 | | | | | | | | 4 | | |
| | SC | 4 | 4 | | | | | | | | 4 | | |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N' dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where $R_2$ is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The compounds of the invention can be prepared and administered in a wide variety of oral, parenteral and topical dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablet-disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. An example may be water or water-propylene glycol solutions for parenteral injection. Such solutions are prepared so as to be acceptable to biological systems (isotonicity, Ph, etc.). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampoules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections, the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

PREPARATION OF INTERMEDIATES

EXAMPLE A (3R,1'S)-3-(1'N-acetylaminoethyl)-1-(S-α-methylbenzyl)pyrrolidin-5-one, 36

(3R,1'S)-3-(1'-Aminoethyl)-1-(S-α -methylbenzyl)pyrrolidin-5-one, 8, (10.0 g, 0.043 mol) was dissolved in pyridine (50 mL) and acetic anhydride (250 mL) and stirred for 18 hours, then evaporated to an oil. This oil was purified by column chromatography using methylene chloride methanol (20/1) to give the title compound as a very viscous oil, yield=9.2 g.

Calculated for $C_{16}H_{22}N_2O_2 \cdot 0.3\ C_2H_6O_1 \cdot 0.2\ H_2O$: C, 68.33; H, 8.36; N, 9.60 Found: C, 68.37; H, 8.09; N, 9.57. $[\alpha]_D=-165°$ (C=0.4%, $CHCl_3$).
$^1$H-NMR ($CDCl_3$) δ 7.4–7.2 (m, 5H), 5.49 (q, 1H, J=9.1 Hz), 5.1–5.05 (broad m, 1H) 4.0–3.85 (m, 1H), 3.39 (dd, 1H, J=8.2, 11.2 Hz), 2.78 (dd, 1H, J=5.8, 10.3 Hz), 2.6–2.36 (m, 2H), 2.25–2.15 (m, 1H), 1.88 (s, 3H), 1.52 (d, 3H, J=7.2 Hz), 0.97 (d, 3H, J=6.7 Hz).

EXAMPLE A-1

(3R,1'R)-3-(1'-N-acetylaminoethyl)-1-(S-α-methylbenzyl)pyrrolidin-5-one, 37

The procedure described above was employed to give 8.3 g of the title compound.

Calculated for $C_{16}H_{22}N_2O_2$: C, 70.04; H, 8.08; N, 10.21 Found: C, 70.08; H, 8.10; N, 10.23.
$[\alpha]_D=-120°$ (C=1.1%, $CHCl_3$).
$^1$H-NMR ($CDCl_3$) δ 7.4–7.2 (m, 5H), 5.85–5.75 (broad m, 1H), 5.47 (q, 1H, J=7.1 Hz), 4.05–3.90 (m, 1H), 3.40–3.30 (m, 1H), 2.80–70 (m, 1H), 2.55–2.20 (m, 3H), 1.84 (s, 3H), 1.52 (d, 3H, J=7.0 Hz), 0.99 (d, 3H, J=6.7 Hz).

EXAMPLE A-2

(3S1'S)-3-(1'-N-acetylaminoethyl)-1-(S-α-methylbenzyl)-pyrrolidin-5-one, 38

The procedure described above was employed to give 9.5 g of the title compound.

Calculated for $C_{16}H_{22}N_2O_2$: C, 70.04; H, 8.08; N, 10.21 Found: C, 70.09; H, 8.01; N, 9.84. $^1$H-NMR ($CDCl_3$) δ 7.4–7.2 (m, 5H), 6.25–6.1 (broad d, 1H), 5.46 (q, 1H, J=7.1 Hz), 4.15–4.05 (m, 1H), 3.20–2.95 (m, 2H), 2.55–2.20 (m, 3H), 1.98 (s, 3H), 1.49 (d, 3H, J=7.1 Hz), 1.09 (d, 3H, J=6.7 Hz).

EXAMPLE A-3

3S,1'R)-3-(1'-N-acetylaminoethyl)-1-(S-α -methylbenzyl)pyrrolidin-5-one, 39

The procedure described above was employed to give 7.4 g of the title compound.

Calculated for $C_{16}H_{22}N_2O_2 \cdot 0.27\ H_2O$: C, 68.82; H, 8.14; N, 10.03 Found: C, 68.87; H, 8.27; N, 9.65. $^1$H-NMR ($CDCl_3$) δ 7.4–7.2 (m, 5H), 5.85–5.75 (broad d, 1H), 5.46 (q, 1H, J=7.1 Hz), 4.05–3.95 (m, 1H), 3.25–3.15 (m, 1H), 3.10–2.95 (m, 1H), 2.55–2.40 (m, 1H), 2.30–2.15 (m, 2H), 1.93 (s, 3H), 1.49 (d, 3H, J=7.0 Hz), 1.11 (d, 3H, J=6.6 Hz).

EXAMPLE B (3R,1'S)-3-(1'-N-ethyl aminoethyl)-1-(S-α-methylbenzyl)pyrrolidine, 40

(3R,1'S)-3-(1'-N-acetylaminoethyl)-1-(S-α -methylbenzyl)pyrrolidin-5-one (9.2 g, 0.03 mol) was dissolved in THF (150 mL) and lithium aluminum hydride (2.6 g) was added portionwise. The resulting slurry was heated at reflux for 18 hours then cooled and cautiously quenched with water (2.6 mL), 15% NaOH solution (3 mL), and water (6 mL). The resulting suspension was filtered and evaporated to an oil. This oil was distilled at 0.1 mm Hg at 107°–112° C. to give 7.1 g of the title compound.
$^1$H-NMR ($CDCl_3$) δ 7.35 (m, 5H), 3.17 (q, 1H, J=6.7 Hz), 2.85–2.60 (m, 3H), 2.60–2.45 (m, 2H), 2.20–1.85 (m, 4H), 1.50–1.30 (m, 1H overlapping with doublet), 1.36 (d, 3H, J=6.5 Hz), 1.08–1.00 (m, 6H).

EXAMPLE B-1

(3R,1'R)-3-(1'-N-ethylaminoethyl)-1-(S-α-methylbenzyl)pyrrolidine, 41

Following the procedure of Example B, the (3R,1'R)-3-(1'-N-acetylaminoethyl)-1-(S-α-methylbenzyl)pyrrolidin-5-one (8.0 g, 0.029 mol) was converted to a crude oil. This oil was distilled at 0.1 mm Hg at 110° C. to give 6.1 g of the title compound.

Calculated for $C_{16}H_{26}N_2 \cdot 0.1\ H_2O$: C, 77.43; H, 10.64, N, 11.29 Found: C, 77.50; H, 10.53; N, 11.56.
$^1$H-NMR ($CDCl_3$) δ 7.35–7.15 (m, 5H), 3.15 (q, 1H, J=6.6 Hz), 2.80–2.65 (m, 2H), 2.60–2.40 (m, 3H), 2.40–2.30 (m, 1H), 2.20–1.90 (m, 4H), 1.70–1.50 (m, 1H), 1.36 (d, 3H, J=6.6 Hz), 1.10 (t, 3H, J=7.2 Hz), 0.95 (d, 3H, J=6.3 Hz).

EXAMPLE B-2

(3S,1'S)-3-(1'-N-ethylaminoethyl)-1-(S-α-methylbenzyl)pyrrolidine, 42

The procedure described above was employed to give 6.88 g of the title compound.

Calculated for $C_{16}H_{26}N_2$: C, 77.99; H, 10.64, N, 11.37 Found: C, 77.68; H, 10.58; N, 11.19. $^1$H-NMR ($CDCl_3$) δ 7.35–7.15 (m, 5H), 3.15 (q, 1H, J=6.6 Hz ), 2.80–2.65 (m, 2H), 2.60–2.35 (m, 4H), 2.20–2.1 0 (m, 2H), 2.05–1.80 (m, 1H), 1.70–1.60 (m, 1H), 1.37 (d, 3H, J=6.6 Hz), 1.10 (t, 3H, J=7.1 Hz ), 0.98 (d, 3H, J=6.2 Hz).

EXAMPLE B-3

(3S,1'R)-3-(1'-N-ethylaminoethyl)-1-(S-α-methylbenzyl)pyrrolidine, 43

The procedure described above was employed to give 5.21 g of the title compound.

Calculated for $C_{16}H_{22}N_2$: C, 77.99; H, 10.64, N, 11.37 Found: C, 78.22; H, 10.63; N, 11.11. MS (EI) 245(P+), 201, 186, 174, 155, 141, 121, 105 (base), 96, 72 $^1$H-NMR ($CDCl_3$) δ 7.40–7.20 (m, 5H), 3.19 (q, 1H, J=6.5 Hz), 2.90–2.75 (m, 1H), 2.75–2.65 (m, 1H), 2.60–2.45 (m, 4H), 2.25–2.10 (m, 2H), 1.95–2.70 (m, 1H), 1.55–1.35 (m, 1H, overlapped with doublet), 1.37 (d, 3H, J=6.5 Hz), 1.15–1.00 (m, 6H).

EXAMPLE C (3R,1'R)-3-(1'-N-ethylaminoethyl)pyrrolidine, 45

(3R,1'R)-3-(1'-N-ethylaminoethyl)-1 -(S-α-methylbenzyl)pyrrolidine (5.4 g, 0.022 mol) was dissolved in methanol (100 mL) and 20% palladium on carbon (1.0 g) was added. The resulting slurry was shaken under 50 psig of hydrogen for 21 hours then depressurized. The resulting suspension was filtered and the filtrate distilled to remove the methanol. The remaining oil was distilled at 10–12 mm Hg at 85°–89° C. to give 2.4 g of the title compound.
$^1$H-NMR (CDCl$_3$) δ 3.10–2.85 (m, 3H), 2.80–2.70 (m, 1H), 2.65–2.50 (m, 2H), 2.10–1.85 (m, 2H), 1.50–1.35 (m, 2H), 1.11 (t, 3H, J=7.0 Hz), 1.04 (d, 3H, J=6.2 Hz).

EXAMPLE C-1

(3R,1'S)-3-(1'-N-ethylaminoethyl)pyrrolidine, 44

The procedure described above was followed to give 3.2 g of the title compound, bp 85°–92° at 10–12 mm Hg.
Calculated for C$_8$H$_{18}$N$_2$: C, 67.55; H, 12.76; N, 19.70 Found: C, 67.58; H, 12.98; N, 19.60. $^1$H-NMR (CDCl$_3$) δ 3.09 (dd, 1H, J=7.7, 10.6 Hz), 3.00–2.85 (m, 2H), 2.80–2.45 (m, 4H), 2.05–1.80 (m, 2H), 1.50–1.30 (m, 1H), 1.15–1.00 (m, 6H).

EXAMPLE C-2

(3S,1'R)-3-(1'-N-ethylaminoethyl)pyrrolidine, 47

The procedure described above was followed to give 2.38 g of the title compound, bp 87°–92° at 10–12 mm Hg.
Calculated for C$_8$H$_{18}$N$_2$ . 0.065 H$_2$O: C, 67.00; H, 12.74; N, 19.35 Found: C, 67.09; H, 13.16; N, 19.35. $^1$H-NMR (CDCl$_3$) δ 3.08 (dd, 1H, J=7.7, 10.5), 2.95–2.85 (m, 2H), 2.75–2.45 (m, 5H), 2.05–1.90 (m, 1H), 1.90–1.80 (m, 1H), 1.50–1.30 (m, 1H), 1.15–1.00 (m, 6H).

EXAMPLE C-3

(3S,1'S)-3-(1'-N-ethylaminoethyl)pyrrolidine, 46

The procedure described above was followed to give 3.28 g of the title compound, bp 88°–92° at 10–12 mm Hg.
Calculated for C$_8$H$_{18}$N$_2$: C, 67.55; H, 12.75; N, 19.70 Found: C, 67.35; H, 13.14; N, 19.57. $^1$H-NMR (CDCl$_3$) δ 3.10–2.85 (m, 3H), 2.80–2.55 (m, 1H), 2.50–2.40 (m, 3H), 2.05–1.80 (m, 2H), 1.50–1.30 (m, 1H), 1.10 (t, 3H, J=7.3 Hz), 1.03 (d, 3H, J=6.1 Hz).

EXAMPLE D 1-(S-α-methylbenzyl)-3-(1'-N-methyl-N-trifluoroacetyl-aminoethyl)pyrrolidin-5-one, 69

A methanol solution (10 mL) of 1-(S-α-methylbenzyl)-3-(1'-aminoethyl)pyrrodin- 5-one (8+9, 13 mmol) was treated with methyl trifluoroacetate (1.92 g, 15 mmol) with stirring for 18 hours, then was evaporated to an oil. This crude oil was dissolved in DMF and added to a suspension of NaH (0.2 g, 5 mmol, 60 wt %) in DMF (10 mL). This mixture was heated to 60° C. for one hour then cooled to ambient temperature. To this was added methyl iodide (0.3 mL, 5 mmol) and the reaction was stirred for 18 hours. The solvent was removed under vacuum (bath=50° C.) and the residue partitioned between methylene chloride and water. The organic layer was dried, filtered, and evaporated to give 1.5 g of the title compound, which was used without purification.

EXAMPLE E 1-(S-α-methylbenzyl)-3-(RS-1'-N-methylaminoethyl)pyrridin-5-one, 70

Compound 69 (1.5 g, 4.4 mmol) was dissolved in 1.0N NaOH solution (10 mL) and ethanol (15 mL) and stirred at 50° C. for one hour. The solution was evaporated under vacuum to remove the ethanol and the residue was partitioned between water and methylene chloride. The methylene chloride layer was separated, the water layer was reextracted, and the combined organic layers were washed with water, dried, filtered and evaporated to give the title compound (0.95 g).

EXAMPLE F 3-(2'-(ethoxycarbonyl)acetyl)-1-(S-α-methylbenzyl)pyrrolidin-5-one, 4

The acid 1 (20.0 g, 85.7 mmol) was suspended in dry THF (350 mL) and the reaction was warmed to 40° C. 1,1'-carbonyldiimidazole (16.0 g, 98.6 mmol) was added to the reaction in portions over 15 minutes. The reaction was warmed to 45° C. and stirred for 24 hours. To the reaction was added the magnesium salt, 3, (30.7 g, 107 mmol). The reaction was warmed to reflux over 0.50 hour, refluxed 3.5 hours, then allowed to cool. The reaction was concentrated in vacuo. The residue taken up in CH$_2$Cl$_2$ (600 mL) was washed with H$_2$O (2×150 mL) followed by dilute NaHCO$_3$ (saturated solution diluted 10 fold, 2×200 mL). The aqueous phases were washed with CH$_2$Cl$_2$ (2×100 mL). The organic layers were combined and washed with saturated NaCl (3×150 mL). The combined brine layers were washed with CH$_2$Cl$_2$ (100 mL). All CH$_2$Cl$_2$ layers were combined, washed again with saturated NaCl (1×150 mL), dried with MgSO$_4$ and concentrated to give the desired product as a brown oil (29.8 g). The crude product was chromatographed (silica gel/EtOAc) giving pure diastereomers; (higher Rf diastereomer)-4 (Rf=0.45, 10.5 g, 37.6%), a mixture of isomers-4 (9.68 g, 30.1%) and (lower Rf diastereomer)-4 (Rf=0.30, 1.61 g, 5.6%) as viscous oils. (Higher Rf diastereomer); $^1$H-NMR (CDCl$_3$) δ 14–1.32 (m, 3H), 1.54 (d, J=7.1 Hz, 3H), 2.57–2.78 (m, 2H), 3.05–3.24 (m, 1H), 3.30–3.46 (m, 1H), 3.48 (s, less than 2H), 3.59 (dd, J=7.2, 6.4 Hz, 1H), 4.11–4.30 (m, 2H), 5.02 (s, less than 1H), 5.49 (q, J=7.1 Hz, 1H), 7.22–7.43 (m, 5H), 12.19 (s, less than 1H), enol tautomer present;

Anal. [C$_{17}$H$_{21}$NO$_4$ 0.27 EtOAc] (Calc., found): C, (66.38, 66.37); H, (7.13, 7.02); N, (4.28, 4.28). (Lower Rf diastereomer); $^1$H-NMR (CDCl$_3$) δ 1.16–1.35 (m, 3H), 1.54 (d, J=7.1 Hz, 3H), 2.58–2.78 (m, 2H), 2.97–3.27 (m)+3.32–3.64, (m)+4.94 (s)-5H total, 4.07–4.27 (m, 2H), 5.51 (q, J=7.1 Hz, 1H), 7.19–7.46 (m, 5H), 12.04 (s, less than 1H), enol tautomer present;

Anal. C$_{17}$H$_{21}$NO$_4$, 0.34 EtOAc] (Calc., found): C, (66.16, 66.08); H, (7.17, 6.80); N, (4.21, 4.20).

The isomers purified above were recombined and used in the next step.

EXAMPLE G

3-acetyl-1-(S-α-methylbenzyl)pyrrolidin-5-one, 5

The combined fractions of the above ketoester, 4, (19.9 g, 65.8 mmol) were dissolved in DMSO (84.0 mL). To the reaction was added NaCl (8.30 g, 142 mmol) and $H_2O$ (4.38 mL, 243 mmol). The reaction was warmed to 130°–135° C. for 20 hours, cooled to room temperature and partitioned between $H_2O$ (400 mL) and $CH_2Cl_2$ (80 mL). The resulting layers were separated. The aqueous layer was washed with $CH_2Cl_2$ (6×75 mL). The organic layers were combined, extracted with $H_2O$ (3×80 mL), dried with $MgSO_4$ and concentrated in vacuo to give crude 6 (15.9 g) as a dark oil. The crude product was chromatographed [silica gel/THF:hexane (1:1)] giving pure diastereomers.

Higher Rf diastereomer (Rf=0.22, 5.53 g, 36.3%), a mixture of isomers—(3.14, 20.6%) and lower Rf diastereomer (Rf=0.11, 6.10 g, 33.9%) as viscous oils.

Higher Rf diastereomer; $^1$H-NMR (CDCl$_3$) δ 1.51 (d, J=7.3 Hz, 3H), 2.16 (s, 3H), 2.63 (d, J=8.4 Hz, 2H), 2.97–3.30 (m, 2H), 3.40–3.63 (m, 1H), 5.46 (q, J=7.3 Hz, 1H), 7.18–7.43 (m, 5H);

Anal. [$C_{14}H_{17}NO_2$]: (Calc., found): C, (72.70, 72.67); H, (7.41, 7.73); N, (6.06, 5.81).

Lower Rf diastereomer; $^1$H-NMR (CDCl$_3$) δ 1.53 (d, J=7.2 Hz, 3H), 2.09 (s, 3H), 2.65 (d, J=8.0 Hz, 2H), 3.08–3.38 (m, 2H), 3.47 (t, J=8.0 Hz, 1H), 5.48 (q, J=7.2 Hz, 1H), 7.20–7.43 (m, 5H);

Anal. [$C_{14}H_{17}NO_2$—0.20 $C_6H_{14}$]: (Calc., found): C, (73.46, 73.34); H, (8.03, 7.85); N, (5.64, 5.28).

The isomers purified above were combined and used in the next step.

EXAMPLE H

3S and 3R-(hydroxyimino)-1-(S-α-methylbenzyl)pyrrolidin-5-one, 6 and 7

To a solution of the ketone, 5 (12.9 g, 56.0 mmol) in pyridine (223 mL), was added hydroxylamine hydrochloride (4.27 g, 61.6 mmol). The reaction was warmed to 45° C. After stirring for 24 hours, the pyridine was removed in vacuo, and the residue was dissolved in CHCl$_3$ (230 mL). The CHCl$_3$ layer was extracted with 0.5N HC$_1$ (11×75.0 mL), dried with $MgSO_4$ and concentrated to a solid (14.2 g). The crude product was chromatographed [silica gel/EtOAc] giving pure diastereomers; 3S-3-(hydroxyimino)-1-(S-α-methylbenzyl)pyrrolidin-5-one, 6, (Rf=0.40, mp 109°–110° C., 5.36 g, 38.9%). Mixture of 6 and 7 (3.21 g, 23.3%) and 3R-3-(hydroxyimino)-1-(S-α -methylbenzyl)pyrrolidin-5-one, 7, (Rf=0.31, mp 125°–127° C., 3.15 g, 22.8%) as solids.

6; $^1$H-NMR (CDCl$_3$) δ 1.50 (d, J=7.0 Hz, 3H), 1.84 (s, 3H), 2.56–2.68 (m, 2H), 2.93–3.22 (m, 2H), 3.34 (dd, J=9.6, 7.0 Hz, 1H), 5.51 (q, J=7.0 Hz, 1H), 7.22–7.43 (m, 5H), 8.65 (s, 1H);

Anal. [$C_{14}H_{18}N_2O_2$]: (Calc., found): C, (68.27, 68.11); H, (7.37, 7.33); N, (11.37, 11.26).

7; $^1$H-NMR (CDCl$_3$) δ 1.53 (d, J=7.2 Hz, 3H), 1.70 (s, 3H), 2.49–2.70 (m, 2H), 2.92 (dd, J=9.8, 6.4 Hz, 1H), 3.03–3.20 (m, 1H), 3.48 (dd, J=9.7, 8.3 Hz, 1H), 5.53 (q, J=7.2 Hz, 1H), 7.19–7.40 (m, 5H), 8.12 (s, 1H);

Anal. [$C_{14}H_{18}N_2O_2$] (Calc., found): C, (68.27, 68.11); H, (7.37, 7.65); N, (11.37, 11.19).

EXAMPLE I

(3S,1'S)-3-(1'-aminoethyl)-1-(S-(α-methylbenzyl)-pyrrolidin-5-one, 10

(3S,1'R)-3-(1'-aminoethyl)-1-(S-α-methylbenzyl)-pyrrolidin-5-one, 11

The oxime, 6, (11.5 g, 46.7 mmol) was dissolved in MeOH saturated with $NH_3$ (100 mL) and placed in a Parr shaker with Raney nickel (4.00 g). The reaction was placed under 51.0 psi of hydrogen and shaken for 20 hours. The reaction was filtered and the filtrate was concentrated to an oil (11.4 g). The crude product was chromatographed [silica gel/CHCl$_3$:EtOH:TEA (20:1:1)] to give pure diastereomers; (3S,1'R)-3 -(1'-aminoethyl)-1-(S-α-methylbenzyl)pyrrolidin- 5-one, 11, (Rf=0.33, 3.02 g, 27.6%), a mixture of isomers-10 and 11 (1.73 g, 15.8%) and (3S,1'S)-3-(1'-aminoethyl)-1-(S-(α -methylbenzyl)pyrrolidin-5-one, 10, (Rf= 0.24, 5.70 g, 52.1%) as viscous oils.

11; $^1$H-NMR (CDCl$_3$) δ 1.06 (d, J=6.4 Hz, 3H), 1.12 (br. s., 2H—disappears with $D_2O$ wash), 1.51 (d, J=7.2 Hz, 3H), 1.90–2.30 (m, 2H), 2.46 (dd, J=16.2, 8.7 Hz, 1H), 2.72–2.92 (m, 1H), 3.12 (d, J=7.7 Hz, 2H), 5.48 (q, J=7.2 Hz, 1H), 7.17–7.43 (m, 5H); IR (LF) 3359, 3030, 1683, 1428, 701 cm$^{-1}$;

Anal. [$C_{14}H_{20}N_2O$, 0.10 $H_2O$] (Calc., found): C, (71.82, 71.84); H, (8.70, 8.64); N, (11.96, 12.16). HPLC=99.5%.

10; $^1$H-NMR (CDCl$_3$/200 MHz) δ 0.99 (d, J=6.4 Hz, 3H), 1.18 (br. s., 2H—disappears with $D_2O$ wash), 1.49 (d, J=7.0 Hz, 3H), 2.00–2.37 (m, 2H), 2.52 (dd, J=16.4, 9.0 Hz, 1H), 2.75–3.13 (m, 3H), 5.47 (q, J=7.0 Hz, 1H), 7.13–7.4 2 (m, 5H); IR (LF) 3366, 2934, 1680, 1427, 701 cm$^{-1}$;

Anal. [$C_{14}H_{20}N_2O$, 0.09 $H_2O$]: (Calc., found): C, (71.88, 71.87); H, (8.69, 8.85); N, (11.97, 11.94). HPLC=97.2%.

EXAMPLE J

(3R,1'S)-3-(1'-aminoethyl)-1-(S-α-methylbenzyl)pyrrolidin-5-one, 8

(3R,1'R)-3-(1'-aminoethyl),1-(S-α-methylbenzyl)pyrrolidin-5-one, 9

In a manner similar to the reduction of 6 (Example I), the oxime 7 was reduced and purified to give pure diastereomers; (3R,1'S)-3-(1'-aminoethyl)-1 -(S-α-methylbenzyl)pyrrolidin-5-one, 8, (Rf=0.33, 3.96 g, 33.8%), a mixture of 8 and 9 (1.97 g, 16.7%) and (3R,1'R)-3-(1'-aminoethyl)-1-(S-α -methylbenzyl)pyrrolidin-5-one, 9, (Rf=0.24, 5.14 g, 43.8%) as viscous oils.

(3R,1'S)-3-(1'-aminoethyl)-1 -(S-α-methylbenzyl)pyrrolidin-5-one, 9; $^1$H-NMR (CDCl$_3$) δ 1.03 (d, J=6.1 Hz, 3H), 1.21 (br. s., 2H—disappears with $D_2O$ wash), 1.52 (d, J=7.0 Hz, 3H), 2.00–2.30 (m, 2H), 2.38–2.60 (m, 1H), 2.62–2.90 (m, 2H), 3.44 (dd, J=9.7, 7.7 Hz, 1H), 5.52 (q, J=7.0 Hz, 1H), 7.17–7.50 (m, 5H);

Anal. [$C_{14}H_{20}N_2O$, 0.68 $H_2O$]: (Calc., found): C, (68.75, 68.77); H, (8.80, 8.68); N, (11.45, 11.30); [α]$_D$=116° (c=1.0, $CH_3OH$); HPLC =99.1%.

(3R,1'R)-3-(1'-aminoethyl)-1 -(S-(α-methylbenzyl)pyrrolidin-5-one, 8; $^1$H NMR (CDCl$_3$) δ 0.91 (d, J=6.3 Hz, 3H), 1.39 (br. s., 2H—disappears with $D_2O$ wash), 1.51 (d, J=7.3 Hz, 3H), 2.02–2.37 (m, 2H), 2.43–2.80 (m, 3H), 3.25–3.43 (m, 1H), 5.51 (q, J=7.3 Hz, 1H), 7.17–7.43 (m, 5H);

Anal. [$C_{14}H_{20}N_2O$, 0.71 $H_2O$]: (Calc., found): C, (68.65, 68.29); H, (8.81, 8.38); N, (11.44, 11.23); [α]$_D$=128° C. (c=1.0, CH$_3$OH); HPLC=99.4%.

EXAMPLE K (3S,1'R)-3-(1'-aminoethyl)-1-(S-α-methylbenzyl)pyrrolidine, 15

To dry THF (150 mL) cooled to 0° C. was added 95% LiAlH$_4$ (2.34 g, 58.6 mmol) portionwise. The ice bath was removed and a solution of 11 (6.81 g, 29.3 mmol) in dry THF (100 mL) was added dropwise. The reaction was warmed to reflux. After 24 hours the reaction was cooled to room temperature and quenched by adding H$_2$O (2.34 mL), then 15% NaOH (2.34 mL), followed by H$_2$O (7.20 mL). The reaction was filtered through celite and the pad was washed with THF. The filtrate was concentrated and the residue partitioned between CH$_2$Cl$_2$ (50.0 mL) and H$_2$O (15.0 mL). The resulting phases were separated and the aqueous phase was washed with CH$_2$Cl$_2$ (3×10.0 mL). The CH$_2$Cl$_2$ layers were combined, dried with MgSO$_4$ and concentrated in vacuo to crude product (6.49 g). This material was distilled to give product as an oil (bp=89°–96° C. at 0.15 mm, 5.56 g, 86.9%).

15; $^1$H-NMR (CDCl$_3$) δ 1.04 (d, J=6.2 Hz, 3H), 1.31–1.73 (m, 6H—contains 1.38 (d, J=6.6 Hz) ), 1.77–2.11 (m, 2H), 2.13–2.27 (m, 1H), 2.38–2.57 (m, 2H), 2.65–2.81 (m, 1H), 2.81–2.93 (m, 1H), 3.19 (q, J=6.6 Hz, 1H), 7.16–7.43 (m, 5H);

Anal. [C$_{14}$H$_{22}$N$_2$]: (Calc., found): C, (77.01, 76.70); H, (10.16, 10.21); N, (12.83, 12.46).

EXAMPLE K-1

(3S,1'S)-3-(1'-aminoethyl)-1-(S-α-methylbenzyl)pyrrolidine, 14

The reduction of 10 was carried out in the same manner as above to give 14 (bp 91°–100° C. at 0.25 mm, 5.57 g, 79.9%).

$^1$H-NMR (CDCl$_3$) δ 1.00 (d, J=6.3 Hz, 3H), 1.24–1.47 (m 5H—contains 1.37 (d, J=6.6 Hz) ), 1.49–1.67 (m, 1H), 1.80–2.16 (m, 3H), 2.38–2.59 (m, 2H), 2.65–2.86 (m, 2H), 3.16 (q, J=6.6 Hz, 1H), 7.13–7.38 (m, 5H);

Anal. [C$_{14}$H$_{22}$N$_2$]: (Calc., found): C, (77.01, 76.66); H, (10.16, 10.08); N, (12.83, 12.50).

EXAMPLE K-2

(3R,1'S)-3-(1'-aminoethyl)1-(S-α-methylbenzyl)pyrrolidine, 12

Compound 8 (3.44 g, 14.8 mmol) was reduced as in K and gave 12 (bp=92°–101° C. at 0.10 mm, 2.53 g 78.0%);

Anal. [C$_{14}$H$_{22}$N$_2$]: (Calc., found): C, (77.01, 76.59); H, (10.16, 9.96); N, (12.83, 11.98).

EXAMPLE K-3

(3R,1'R)-3-(1'-aminoethyl)-1-(S-α-methylbenzyl)pyrrolidine, 13

Compound 9 (4.51 g, 19.4 mmol) was reduced as in K and gave 13 (bp 83°–94° C. at 0.05 mm, 2.93 g, 68.9%);

Anal. [C$_{14}$H$_{22}$N$_2$]: (Calc., found): C, (77.01, 76.21); H, (10.16, 10.28); N, (12.83, 12.20).

General preparation of the 3-( 1'-N-t-butyloxycarbonylaminoethyl)-1-(S-α-methylbenzyl)pyrrolidines (16–19)

The pyrrolidines (12–15) were added to a cold solution of di-t-butyloxycarbonate (1.10–1.20 eq), 1N NaOH (1.10–1.20 eq) and t-BuOH (35–50 mL). The ice bath was removed and the reactions stirred at room temperature. After stirring 24 hours, the product was isolated by diluting the reaction with H$_2$O (100 mL) and extracting the aqueous solution with ether (5×25 mL). The ether layers were combined, dried with MgSO$_4$ and concentrated in vacuo to give crude product. The crude products were purified by chromatography [silica gel/CH$_2$Cl$_2$:EtOH(90:10)/] to give pure products.

EXAMPLE L (3S,1'R)-3-(1'-N-t-butyloxycarbonylaminoethyl)-1-(S-α-methylbenzyl)pyrrolidine, 19

This compound was obtained from 15 using the general procedure described (Rf=0.24, 4.87 g, 62.5%);

$^1$H-NMR (CDCl$_3$) δ 1.06 (d, J=6.6 Hz, 3H), 1.30–1.68 (m, 13H—contains 1.38 (d, J=6.7 Hz) and 1.46 (s)), 1.83–2.23 (m, 2H), 2.25–2.60 (m, 3H), 2.68–2.90 (m, 1H), 3.19 (q, J=6.5 Hz, 1H), 3.40–3.63 (m, 1H), 5.26–5.47 (m, 1H), 7.17–7.43 (m, 5H);

Anal. [C$_{19}$H$_{30}$N$_2$O, 0.13 CH$_2$Cl$_2$]: (Calc., found): C, (69.73, 69.68); H, (9.26, 9.17); N, (8.50, 8.50).

EXAMPLE L-1

(3S,1'S)-3-(1'-N-t-butyloxycarbonylaminoethyl)-1-(S-α-methylbenzyl)pyrrolidine, 18

This compound was obtained from 14 using the general procedure described (Rf=0.33, 5.18 g, 67.4%);

$^1$H-NMR (CDCl$_3$) δ 1.11 (d, J=6.2 Hz, 3H), 1.30–2.00 (m, 14H—contains 1.37 (d, J=6.3 Hz) ), 2.03–2.38 (m, 3H), 2.43–2.63 (m, 1H), 2.65–2.85 (m, 1H), 3.14 (q, J=6.4 Hz, 1H), 3.37–3.63 (m, 1H), 5.20 (br. s., 1H), 7.17–7.43 (m, 5H);

Anal. [C$_{19}$H$_{30}$N$_2$O$_2$, 0.17 CH$_2$Cl$_2$]: (Calc., found): C, (69.17, 69.15); H, (9.19, 8.98); N, (8.41, 8.22).

EXAMPLE L-2

(3R,1'S)-3-(1'-N-t-butyloxycarbonylaminoethyl)-1-(S-α-methylbenzyl)pyrrolidine, 16

This compound was obtained from 12 using the general procedure described (Rf=0.24, 1.64 g, 44%);

$^1$H-NMR (CDCl$_3$) δ 1.16 (d, J=7.3 Hz, 3H), 1.32–1.66 (m, 13H), 1.85–2.27 (m, 2H), 2.30–2.87 (m, 4H), 3.10–3.33 (m, 1H), 3.40–3.67 (m, 1H), 5.65 (br. s., 1H), 7.17–7.43 (m, 5H);

Anal. [C$_{19}$H$_{30}$N$_2$O$_2$, 0.19 CH$_2$Cl$_2$]: (Calc., found): C, (68.89, 68.96); H, (9.15, 8.86); N, (8.37, 8.13).

EXAMPLE L-3

(3R,1'R)-3-(1'-N-t-butyloxycarbonylaminoethyl)-1-(S-α-methylbenzyl)pyrrolidine, 17

This procedure was obtained from 13 using the general procedure described (Rf=0.33, 1.76 g, 45.4%);

$^1$H-NMR (CDCl$_3$) δ 1.07 (d, J=7.3 Hz, 3H), 1.32–1.55 (m, 12H), 1.55–1.77 (m, 1H), 1.77–2.03 (m, 1H), 2.03–2.87 (m, 5H), 3.07–3.30 (m, 1H), 3.43–3.70 (m, 1H), 5.13 (br. s., 1H), 7.17–7.43 (m, 5H);

Anal. [C$_{19}$H$_{30}$N$_2$O$_2$, 0.08 CH$_2$Cl$_2$]: (Calc., found): C, (70.46, 70.39); H, (9.35, 9.10); N, (8.61, 8.70).

General Procedure for the Preparation of 3-(1'-N-t-butyloxycarbonylaminoethyl)pyrrolidines, 20–23

The compound (16–19) was dissolved in MeOH (100 mL) and 20% Pd/C (0.30–1.00 g) in a Parr shaker. The reaction was placed under H$_2$ (50.0 psi). After shaking 18–26 hours, additional catalyst was required (0.30–1.60 g). The reaction was shaken for another 2–6 hours, then filtered. The filtrate was concentrated in vacuo and the residue was taken up in H$_2$O. The aqueous solution was extracted with diethyl ether, made basic with 50% NaOH, extracted with CH$_2$Cl$_2$ or CHCl$_3$. The combined organic layers were dried with MgSO$_4$ and concentrated to a waxy solid. These compounds were used as is or were purified by trituration with ether or ether/pentane and filtration of the purified solid.

EXAMPLE M (3S,1'R)-3-(1'-N-t-butyloxycarbonylaminoethyl)pyrrolidine, 23

Compound 23 was obtained from 19 using the method described above; (0.93 g, 62.8%); $^1$H-NMR (CDCl$_3$) δ 1.15 (d, J=6.5 Hz, 3H), 1.30–1.57 (m, 10H), 1.72–2.15 (m, 2H), 2.60 (br. s., disappears with D$_2$O wash), 2.70–2.86 (m, 1H), 2.87–3.17 (m, 3H), 3.43–3.70 (m, 1H), 4.50–4.73 (m, 1H–disappears with D$_2$O wash);

Anal. [C$_{11}$H$_{22}$N$_2$O$_2$, 0.08 CH$_2$Cl$_2$]: (Calc., found): C, (60.19, 60.25); H, (10.10, 9.77); N, (12.67, 12.30).

EXAMPLE M-1

(3S,1'S)-3-(1'-N-t-butyloxycarbonylaminoethyl)pyrrolidine, 22

Compound 22 was obtained from 18 using the method described above; (0.72 g, 89.8%); $^1$H-NMR (CDCl$_3$) δ 1.11 (d, J=6.5 Hz, 3H), 1.30–1.63 (m, 10H), 1.73–2.15 (m, 2H), 2.43–2.67 (m, 1H), 2.77–3.12 (m, 3H), 3.45–3.70 (m, 1H).

Anal. [C$_{11}$H$_{22}$N$_2$O$_2$]: (Calc., found): C, (61.65, 60.82); H, (10.35, 10.10); N, (13.07, 12.03).
Used without further purification in the next step.

EXAMPLE M-2

(3R,1'S)-3-(1'-N-t-butyloxycarbonylaminoethyl)pyrrolidine, 20

Compound 20 was obtained from 16 using the method described above; mp 71.5°–74.5° C.; $^1$H-NMR (CDCl$_3$) δ 1.15 (d, J=6.5 Hz, 3H), 1.30–1.60 (m, 10H—contains 1.44 (s)), 1.70–2.13 (m, 2H -contains broad peak which disappears with D$_2$O wash), 2.66–3.10 (m, 4H), 3.42–3.70 (m, 1H), 4.62 (br. s., 1H—disappears with D$_2$O wash);

Anal. [C$_{11}$H$_{22}$N$_2$O$_2$, 0.25 H$_2$O]: (Calc., found): C, (60.38, 60.37); H, (10.36, 10.09); N, (12.80, 12.62).

EXAMPLE M-3

(3R,1'R)-3-(1'-N-t-butyloxycarbonylaminoethyl)pyrrolidine, 21

Compound 21 was obtained from 17 using the method described above; mp 85.5°–88.5° C.; $^1$H-NMR (CDCl$_3$) δ 1.12 (d, J=6.5 Hz, 3H), 1.21–1.67 (m, 10H—contains 1.44 (s)), 1.73–2.17 (m, 2H—contains br. s. which disappears with D$_2$O wash), 2.50–2.68 (m, 1H), 2.80–3.17 (m, 3H), 3.43–3.75 (m, 1H), 4.50 (br. s., 1H—disappears with D$_2$O wash);

Anal. [C$_{11}$H$_{22}$N$_2$O$_2$, 0.25 H$_2$O]: (Calc., found): C, (60.38, 60.36); H, (10.36, 10.16); N, (12.80, 12.63).

General Procedure for the Preparation of the 3-(1'-N,N-dimethylaminoethyl)-1-S-α-methylbenzyl)pyrrolidinones 24–27

To the chiral amines (8–11), cooled in an ice/water bath was added 88% formic acid (2.5 eq) and 35% formaldehyde. The ice bath was removed and the reaction was warmed slowly over 25–60 minutes. Gas evolution occurred. The reaction was then warmed to reflux for five hours, cooled to room temperature, and made basic with 1N NaOH. The reaction was extracted with diethyl ether. The combined ether layers were washed with saturated NaCl, dried with MgSO$_4$, filtered and concentrated in vacuo to provide the desired products.

EXAMPLE N (3S,1'R)-3-(1'-N,N-dimethylaminoethyl)-1-(S-α-methylbenzyl)pyrrolidin-5-one, 27

The compound 27 was obtained from 11 as described above; bp 0.20–0.25 mm, mp 140°–157° C.; 1H-NMR (CDCl$_3$) δ 0.88 (d, J=6.5 Hz, 3H), 1.52 (d, J=7.1 Hz, 3H), 2.03–2.32 (m, 8H—contains 2.14 (s)), 2.35–3.55 (m, 2H), 3.01–3.30 (m, 2H), 5.48 (q, J=7.1 Hz, 1H), 7.19–7.40 (m, 5H);

Anal. [C$_{16}$H$_{24}$N$_2$O]: (Calc., found): C, (73.81, 73.48); H, (9.29, 9.47); N, (10.76, 10.55).

EXAMPLE N-1

(3S,1'S)-3-(1'-N,N-dimethylaminoethyl)-1-(S-α-methylbenzyl)pyrrolidin-5-one, 26

The compound 26 was obtained from 10 as described above. The crude product was recrystallized from diethyl ether to give (1.31 g, 30%). The filtrate was concentrated to give an additional material which was used without further purification (2.52 g, 57.6%); $^1$H-NMR (CDCl$_3$) δ 0.83 (d, J=6.4 Hz, 3H), 1.51 (d, J=7.1 Hz, 3H), 2.08–2.59 (m, 10H—contains 2.18 (s)), 2.87–3.07 (m, 2H), 5.50 (q, J=7.1 Hz, 1H), 7.19–7.40 (m, 5H);

Anal. [C$_{16}$H$_{24}$N$_2$O]: (Calc., found): C, (73.81, 73.68); H, (9.29, 9.46); N, (10.76, 10.71).

EXAMPLE N-2

(3R, 1'S)-3-(1'-N,N-dimethylaminoethyl)-1-(S-α-methylbenzyl)pyrrolidin-5-one, 24

The compound 24 was obtained from 8 as described above; (12.54 g, 92.3%); $^1$H-NMR (CDCl$_3$) δ 0.84 (d, J=6.0 Hz, 3H), 1.52 (d, J=7.1 Hz, 3H), 1.97–2.20 (m, 7H—contains 2.11 (s)), 2.20–2.58 (m, 3H), 2.88 (dd, J=10.1, 6.8 Hz, 1H), 3.38 (dd, J=10.1, 7.3 Hz, 1H), 5.51 (q, J=7.1 Hz, 1H), 7.18–7.43 (m, 5H);

Anal. [$C_{16}H_{24}N_2O$, 0.15 $H_2O$]: (Calc., found): C, (73.05, 73.37); H, (9.31, 9.38); N, (10.65, 10.25).

EXAMPLE N-3

(3R,1'R)-3-(1'-N,N-dimethylaminoethyl)-1-(S-α-methylbenzyl)pyrrolidin-5-one, 25

The desired product 25 was obtained from 9 as described above; (11.27 g, 83.8%); $^1$H-NMR (CDCl$_3$) δ 0.73 (d, J=5.9 Hz, 3H), 1.52 (d, J=7.1 Hz, 3H), 2.15 (s, 6H), 2.22–2.63 (m, 5H), 3.22–3.38 (m, 1H), 5.52 (q, J=7.1 Hz, 1H), 7.18–7.43 (m, 5H);

Anal. [$C_{16}H_{24}N_2O$, 0.17 $H_2O$]: (Calc., found): C, (72.95, 73.00); H, (9.31, 9.69); N, (10.63, 10.39).

General Procedure for the Preparation of the 3-(1'-N,N-dimethylaminoethyl)-1-(S-α-methylbenzyl)pyrrolidines 28–31

To cold, dry THF (100–200 mL) was added 95% LiAlH$_4$ (2 eq). The ice bath was removed and a solution of the chiral amides (24–27) in THF (50 mL) was added dropwise. The reaction was refluxed 17–18 hours then cooled to room temperature. The reaction was quenched by adding first 1 mL of H$_2$O/gram of LiAlH$_4$ used followed by 1 mL of 15% NaOH/gram of LiAlH$_4$ used and finally 3 mL of H$_2$O/gram of LiAlH$_4$ used. The suspension was filtered through celite and the filter pad was washed with THF. The filtrate was concentrated and the residue was partitioned between CH$_2$Cl$_2$ and saturated NaCl solution. The resulting layers were isolated. The aqueous layer was washed with CH$_2$Cl$_2$. The CH$_2$Cl$_2$ layers were combined, dried with MgSO$_4$ and concentrated in vacuo. The crude material was distilled to give the pure product.

EXAMPLE O (3S,1'R)-3-(1'-N,N-dimethylaminoethyl)-1-(Sα-methylbenzyl)pyrrolidine, 31

Compound 31 (4.65 g, 80%) was obtained from 27 as described; bp 0.10–0.15 mm Hg, 95°–105° C.; $^1$H-NMR (CDCl$_3$) δ 0.86 (d, J=6.2 Hz, 3H), 1.23–1.46 (m, 4H—contains 1.39 (d, J=6.6 Hz)), 1.74–1.95 (m, 1H), 2.08–2.46 (m, 10H), 2.46–2.61 (m, 1H), 3.00–3.24 (m, 2H—contains 3.18 (q, J=6.6 Hz) ), 7.11–7.38 (m, 5H);

Anal. [$C_{16}H_{26}N_2$]: (Calc., found): C, (77.99, 77.70); H, (10.64, 10.98); N, (11.37, 11.32).

EXAMPLE O-1

(3S,1'S)-3-(1'-N,N-dimethylaminoethyl)-1-(S-α-methylbenzyl)pyrrolidine, 30

Compound 30 (3.97 g, 79%) was obtained from 26 as described; bp 0.15 mm Hg, 96°–102° C.; $^1$H-NMR (CDCl$_3$) δ 0.83 (d, J=6.4 Hz, 3H), 1.38 (d, J=6.6 Hz, 3H), 1.54–1.78 (m, 1H), 1.78–2.04 (m, 2H), 2.07–2.41 (m, 9H—contains 2.19 (s)), 2.41–2.62 (m, 1H), 2.90 (dd, J=8.5, 7.7 Hz, 1H), 3.17 (q, J=6.6 Hz, 1H), 7.12–7.36 (m, 5H);

Anal. [ $C_{16}H_{26}N_2$]: (Calc., found): C, (77.99, 77.52); H, (10.64, 11.02); N, (11.37, 11.06).

EXAMPLE O-2

(3R,1'S)-3-(1'-N,N-dimethylaminoethyl)-1-(S-α-methylbenzyl)pyrrolidine, 28

Compound 28 (9.06 g, 82%) was obtained from 24 as described; bp 0.10 mm Hg, 98°–109° C.; $^1$H-NMR (CDCl$_3$, 250 MHz) 0.85 (d, J=6.4 Hz, 3H), 1.24–1.45 (m, 4H—contains 1.36 (d, J=6.6 Hz), 1.77–2.00 (m, 1H), 2.00–2.48 (m, 10H—contains 2.14 (s)), 2.61–2.83 (m, 2H), 3.19 (q, J=6.6 Hz, 1H), 7.12–7.37 (m, 5H);

Anal. [$C_{16}H_{26}N_2$]: (Calc., found): C, (77.99, 77.96); H, (10.64, 10.72); N, (11.34, 11.36).

EXAMPLE O-3

(3R,1'R)-3-(1'-N,N-dimethylaminoethyl)-1-(S-α-methylbenzyl)pyrrolidine, 29

Compound 29 (7.99 g, 80%) was obtained from 25 as described; bp 0.10 mm Hg, 103°–109° C.; $^1$H-NMR (CDCl$_3$) δ 0.75 (d, J=6.4 Hz, 3H), 1.37 (d, J=6.6Hz, 3H), 1.58–1.77 (m, 1H), 1.81–2.46 (m, 11H—contains 2.17 (s)), 2.51–2.66 (m, 1H), 2.85–3.00 (m, 1H), 3.15 (q, J=6.6 Hz, 1H), 7.15–7.38 (m, 5H).

Anal. [$C_{16}H_{26}N_2$]: (Calc., found): C, (77.99, 77.95); H, (10.64, 10.75); N, (11.36, 11.23).

General Procedure for the Preparation of 3-(1'-N,N-dimethylaminoethyl)pyrrolidines 32–35

The chiral amines (28–31) were dissolved in MeOH (100 mL) and placed in a Parr shaker. To this solution was added 20% Pd/C (1.00–1.50 g). The reaction was placed under H$_2$ gas (50 psi) and shaken for 3–4 hours. The reaction was filtered and the filtrate was concentrated in vacuo. The residue was distilled to give pure product.

EXAMPLE P (3S,1'R)-3-(1'-N,N-dimethylaminoethyl)pyrrolidine, 35

Compound 35 (1.76 g, 56%) was obtained from 31 as described; bp 10.0 mm Hg, 89°–104° C.); $^1$H-NMR (CDCl$_3$) δ 0.91 (d, J=6.4 Hz, 3H), 1.19–1.40 (m, 1H), 1.75–2.12 (m, 3H), 2.20 (s, 6H), 2.25–2.47 (m, 1H), 2.69 (dd, J=10.9, 8.1 Hz, 1H), 2.82–3.02 (m, 2H), 3.10 (dd, J=10.9, 7.6 Hz,1H); $^{13}$C-NMR (CDCl$_3$, 250 MHz) 9.5, 30.8, 40.2, 44.2, 47.0, 51.7, 63.2;

Anal. [$C_8H_{18}N_2$, 0.10 $H_2O$]: (Calc., found): C, (66.71, 66.95); H, (12.74, 12.64); N, (19.45, 19.09).

EXAMPLE P-1

(3S,1'S)-3-(1'-N,N-dimethylaminoethyl)pyrrolidine, 34

Compound 34 (1.19 g, 71%) was obtained from 30 as described; bp 10.0 mm Hg, 83°–110° C.; $^1$H-NMR (CDCl$_3$) δ 0.87 (d, J=6.4Hz, 3H), 1.47–1.67 (m, 1H), 1.82–2.13 (m, 2H), 2.22 (s, 6H), 2.28–2.53 (m, 2H), 2.82–2.98 (m, 2H).

EXAMPLE P-2

(3R,1'S)-3-(1'-N,N-dimethylaminoethyl)pyrrolidine, 32

Compound 32 (3.53 g, 68%) was obtained from 28 as described; bp 14.0 mm Hg, 81°–84° C.; $^1$H-NMR (CDCl$_3$), δ 0.90 (d, J=6.1 Hz, 3H), 1.17–1.41 (m, 1H), 1.73–2.13 (m, 2H), 2.20 (s, 6H), 2.25–2.47 (m, 1H), 2.68 (dd, J=11.0, 7.9 Hz, 1H), 2.81–3.00 (m, 2H), 3.08 (dd, J=11 Hz, 7.3 Hz, 1H); $^{13}$C NMR (CDCl$_3$, 63 MHz), 9.3, 30.7, 40.1, 44.1, 46.9, 51.6, 63.1;

Anal. [C$_8$H$_{18}$N$_2$, 0.12H$_2$O] (Calc. found): C (66.54, 66.41); H (12.73, 12.79); N (19.40, 19.79).

EXAMPLE P-3

(3R,1'R)-3-(1'-N,N-dimethylaminoethyl)pyrrolidine, 33

Compound 33 (3.04 g, 68%) was obtained from 29 as described; bp 15.0–17.0 mm Hg, 83°–86° C.; $^1$H-NMR (CDCl$_3$+D$_2$O) δ 0.87 (d, J=6.3 Hz, 3H), 1.44–1.68 (m, 1H), 1.97–2.52 (m, 10H—contains 2.22 (s)), 2.78–3.11 (m, 3H—contains 3.01 (dd, J=10.5, 7.5 Hz)).

Anal. [C$_8$H$_{18}$N$_2$, 0.09 H$_2$O] (Calc., found): C (66.79, 66.78); H (12.74, 13.00); N (19.47, 19.74).

General Procedure for the Preparation of the 3-(1'-N-tert-butoxycarbonylaminoethyl)-1-(S-α-methylbenzyl)pyrrolidin-5-ones, 48–50

A solution of di-tert-butylcarbonate (1.1 eq) in dichloromethane was added portionwise to a stirred solution of the corresponding primary amine (8–11) and triethylamine (1.1 eq) in dichloromethane (250 mL). The resulting solution was stirred at room temperature for 20 hours, and then concentrated under reduced pressure to give a light yellow oil. These crude products were purified by column chromatography (silica gel, heptane-isopropanol 4:1).

EXAMPLE Q (3R,1'R)-3-(1'-N-tert-butoxycarbonylaminoethyl)-1-(S-α-methylbenzyl)pyrrolidin-5-one, 49

From 6.68 g (28.7 mmol) of amine 9, 7.64 g (35 mmol) of di-tert-butylcarbonate, and 3.54 g (35 mmol) of triethylamine, there was obtained 49 (5.43 g, 57%) as a white, wax-like glass.

$[α]_D$=−116° (C=0.99, chloroform).
$^1$H-NMR (CDCl$_3$) δ 0.96 (d, 3H, J=6.7 Hz), 1.38 (s, 9H), 1.52 (d, 3H, J=7.2 Hz), 2.23–2.55 (m, 3H), 2.66 (dd, 1H, J=9.8, 7.0 Hz), 3.32 (dd, 1H, J=9.8, 8.1 Hz), 3.50–3.70 (m, 1H), 4.35–4.45 (m, 1H), 5.50 (q, 1H, J=7.1 Hz), 7.23–7.37 (m, 5H).

Anal. Calcd. for C$_{19}$H$_{28}$N$_2$O$_3$: C, 68.65; H, 8.49; N, 8.43 Found: C, 68.55; H, 8.53; N, 8.13.

EXAMPLE Q-1

(3R,1'S)-3(1'-N-tert-butoxycarbonylaminoethyl)-1-(S-α-methylbenzyl)pyrrolidin-5-one, 48

From 5.95 g (25.6 mmol) of amine 8, 6.77 g (31.0 mmol) of di-tert-butylcarbonate, and 3.14 g (31.0 mmol) of triethylamine, there was obtained 48 (7.46 g, 88%) as a white, wax-like glass.

$[α]_D$=−127° (c=1.04, chloroform).
$^1$H-NMR (d$_6$-DMSO) δ 0.90 (d, 3H, J=6.5 Hz), 1.34 (s, 9H), 1.44 (d, 3H, J=7.1 Hz), 2.04–2.20 (m, 1H), 2.21–2.41 (m, 2H), 2.69 (dd, 1H, J=9.6, 6.5 Hz), 3.28–3.42 (m, 2H), 5.25 (q, 1H, J=7.1 Hz), 6.78 and 6.85 (2×d, 1H, J=8.6 and 7.9 Hz), 7.24–7.37 (m, 5H).

Anal. Calcd. for C$_{19}$H$_{28}$N$_2$O$_3$: C, 68.65; H, 8.49; N, 8.43. Found: C, 68.45; H, 8.59; N, 8.38.

EXAMPLE Q-2

(3S,1'R)-3-(1'-N-tert-butoxycarbonylaminoethyl)-1-(S-α-methylbenzyl)pyrrolidin-5-one, 51

From 10.19 g (44 mmol) of amine 11, 11.57 g (53 mmol) of di-tert-butylcarbonate, and 5.36 g (53 mmol) of triethylamine, there was obtained 51 (13.16 g, 90%) as a white solid; mp 120°–121° C. (from dichloromethane-heptane).
$[α]_D$=−32° (c=0.96, chloroform).
$^1$H-NMR (CDCl$_3$) δ 1.10 (d, 3H, J=6.6 Hz), 1.41 (s, 9H), 1.50 (d, 3H, J=7.2 Hz), 2.14–2.29 (m, 2H), 2.45 (dd, 1H, J=19.5, 12.2 Hz), 2.99–3.06 (m, 1H), 3.12–3.19 (m, 1H), 3.57–3.68 (m, 1H), 4.81 (br. d, 1H, J=9.1 Hz), 5.45 (q, 1H, J=7.1 Hz), 7.19–7.35 (m, 5H).

Anal. Calcd. for C$_{19}$H$_{28}$N$_2$O$_3$: C, 68.65; H, 8.49; N, 8.43. Found: C, 68.66; H, 8.64; N, 8.38.

EXAMPLE Q-3

(3S,1'S)-3-(1'-N-tert-butoxycarbonylaminoethyl)-1-(S-α-methyl-benzyl)pyrrolidin-5-one, 50

From 10.02 g (43 mmol) of amine 10, 11.35 g (52 mmol) of di-tert-butylcarbonate, and 5.26 g (52 mmol) of triethylamine, there was obtained 50 (13.00 g, 91%) as a white solid; mp 148°–149° C. (from dichloromethane-hexane).
$[α]_D$=−110° (C=1.03, chloroform).
$^1$H-NMR (CDCl$_3$) δ 1.08 (d, 3H, J=6.7 Hz), 1.43 (s, 9H), 1.50 (d, 3H, J=7.1 Hz), 2.20–2.56 (m, 3H), 2.97–3.13 (m, 2H), 3.70–3.83 (m, 1H), 4.76 (br. d, 1H, J=9.1 Hz), 5.48 (q, 1H, J=7.1 Hz), 7.23–7.36 (m, 5H).

Anal. Calcd. for C$_{19}$H$_{28}$N$_2$O$_3$: C, 68.64; H, 8.49; N, 8.43. Found: C, 68.50; H, 8.61; N, 8.57.

General Procedure for the Preparation of the 3-(1'-N-methylaminoethyl)-1-(S-α-methylbenzyl)pyrrolidines, 52–55

A solution of 3-(1'-N-tert-butoxycarbonylamino ethyl)-1-(S-α-methylbenzyl)pyrrolidin-5-one (48–51) in dry THF (25 mL) was added dropwise to a stirred suspension of lithium aluminum hydride (2 equivalents) in dry THF (10 mL). The suspension was heated at reflux for six hours, allowed to cool to room temperature, and quenched by the dropwise addition of saturated aqueous ammonium sulfate solution (2 mL) and water (2 mL). The resulting slurry was stirred at room temperature for a few minutes and then filtered through a pad of Celite. The solids were rinsed with dichloromethane, and the combined filtrate and washings were dried and concentrated to afford the corresponding 3-(1'-N-methylaminoethyl)-1-(S-α-methylbenzyl)pyrrolidine.

EXAMPLE R (3R,1'R)-3-(1'-N-methylaminoethyl)-1-(S-α-methylbenzyl)pyrrolidine, 53

From 11.80 g (36 mmol) of 49 and 2.69 g (71 mmol) of LiAlH$_4$, the above procedure provided 53 (7.85 g, 94%) as a yellow oil.

$[\alpha]_D$=−75° (C=1.90, chloroform). $^1$H-NMR (CDCl$_3$) δ 0.94 (d, 3H, J=6.3 Hz), 1.12–1.40 (m, 1H), 1.36 (d, 3H, J=6.4 Hz), 1.50–1.63 (m, 1H), 1.88–2.07 (m, 1H), 2.09–2.20 (m, 2H), 2.25–2.45 (m, 2H), 2.39 (s, 3H), 2.49–2.62 (m, 1H), 2.72–2.81 (m, 1H), 3.15 (q, 1H, J=6.5 Hz), 7.21–7.33 (m, 5H).

Anal. Calcd. for C$_{15}$H$_{24}$N$_2$ . 0.25H$_2$O: C, 76.06; H, 10.43; N, 11.83. Found: C, 76.20; H, 10.16; N, 11.57.

EXAMPLE R-1

(3R,1'S)-3-(1'-N-methylaminoethyl)-1-(S-α-methylbenzyl)pyrrolidine, 52

From 5.30 g (16 mmol) of 48 and 1.21 g (32 mmol) of LiAlH$_4$ the above procedure provided 52 (3.54 g, 95%) as a clear liquid.

$^1$H-NMR (CDCl$_3$) δ 1.01 (d, 3H, J=6.2 Hz), 1.36 (d, 3H, J=6.5 Hz), 1.40–1.55 (m, 1H), 1.83–2.02 (m, 1H), 2.04–2.20 (m, 2H), 2.27–2.44 (m, 2H), 2.35 (s, 3H), 2.63–2.69 (m, 1H), 2.74–2.85 (m, 1H), 3.16 (q, 1H, J=6.6 Hz), 7.20–7.34 (m, 5H).

Anal. Calcd. for C$_{15}$H$_{24}$N$_2$ . 0.04 CH$_2$Cl$_2$: C, 76.62; H, 10.29; N, 11.88 Found: C, 76.55; H, 10.69; N, 11.57.

EXAMPLE R-2

(3S,1'R)-3-(1-N-methylaminoethyl)-1-(S-α-methylbenzyl)pyrrolidine, 55

From 14.95 g (45 mmol) of 51 and 3.42 g (90 mmol) of LiAlH$_4$, the above procedure provided 55 (9.12 g, 87%) as a light yellow oil.

$[\alpha]_D$=−49° (c=0.89, chloroform).

$^1$H-NMR (CDCl$_3$) δ 1.02 (d, 3H, J=6.2 Hz), 1.38 (d, 3H, J=6.6 Hz), 1.43–1.54 (m, 1H), 1.78–1.92 (m, 1H), 2.09–2.29 (m, 2H), 2.35–2.40 (m, 1H), 2.38 (s, 3H), 2.46 (t, 2H, J=6.9 Hz), 2.83–2.93 (m, 1H), 3.19 (q, 1H, J=6.6 Hz), 7.20–7.34 (m, 5H).

Anal. Calcd. for C$_{15}$H$_{24}$N$_2$ . 0.25 H$_2$O: C, 76.06; H, 10.43; N, 11.83 Found: C, 76.10; H, 10.54; N, 12.04.

EXAMPLE R-3

(3S,1'S )-3-(1'-N-methylaminoethyl)-1-(S-α-methylbenzyl)pyrrolidine, 54

From 12.74 g (38 mmol) of 50 and 2.66 g (70 mmol) of LiAlH$_4$, the above procedure provided 54 (7.30 g, 82%) as a faint yellow oil.

$[\alpha]_D$=−38° (C=1.00, chloroform)

$^1$H-NMR (CDCl$_3$) δ 0.98 (d, 3H, J=6.2 Hz), 1.37 (d, 3H, J=6.6 Hz), 1.47–1.70 (m, 1H), 1.81–1.95 (m, 1H), 2.08–2.23 (m, 2H), 2.30–2.58 (m, 3H), 2.39 (s, 3H), 2.65–2.78 (m, 1H), 3.16 (q, 1H, J=6.6 Hz), 7.21–7.37 (m, 5H).

Anal. Calcd. for C$_{15}$H$_{24}$N$_2$ . 0.50 H$_2$O: C, 74.64; H, 10.44; N, 11.61 Found: C, 74.82; H, 10.29; N, 11.48.

General Procedure for the Preparation of the 3-(1'-N-tert-butoxycarbonyl-N-methylaminoethyl)-1-(S-α-methylbenzyl)pyrrolidines, 56–59

A solution of di-tert-butylcarbonate (1.1–1.3 eq) in dichloromethane (5 mL) was added portionwise to a chilled solution of 3-(1'-N-methylaminoethyl)-1-(S-α-methylbenzyl)pyrrolidines (52–55) and triethylamine (1.1–1.3 eq) in dichloromethane (15 mL). The resulting solution was stirred at room temperature overnight, and then concentrated to afford the product as a viscous yellow oil. The crude product was purified by column chromatography (silica gel, hexanes/2-propanol 4:1).

EXAMPLE S (3R,1'R)-3-(1'-N-tert-butoxycarbonyl-N-methylaminoethyl)-1-(S-α-methylbenzyl)pyrrolidine, 57

From 3.33 g (14 mmol) of amine 53, 3.71 g (17 mmol) of di-tert-butylcarbonate, and 1.72 g (17 mmol) of triethylamine, the above procedure provided 57 (4.17 g, 88%) as a yellow oil which solidified upon cooling to 0° C.

$[\alpha]_D$=−25° (C=0.25, chloroform).

$^1$H-NMR (CDCl$_3$) δ 0.92 and 0.95 (2×d superimposed, 3H), 1.36 d, 3H, J=6.5 Hz), 1.40–1.60 (m, 1H), 1.46 (s, 9H), 1.75–1.93 (m, 2H), 2.08–2.35 (m, 2H), 2.55–2.71 (m, 4H), 2.90–3.09 (m, 1H), 3.11–3.24 (m, 1H), 3.75–3.90 and 3.98–4.12 (m, 1H) 7.18–7.37 (m, 5H).

Anal. Calcd. for C$_{20}$H$_{32}$N$_2$O$_2$ . 0.03 CH$_2$Cl$_2$ . 0.72 C$_4$H$_8$O$_2$: C, 69.06; H, 9.57; N, 7.03 Found: C, 69.04; H, 9.59; N, 7.05.

EXAMPLE S-1

(3R,1'S)-3-(1'-N-tert-butoxycarbonyl-N-methylaminoethyl)-1-(S-α-methylbenzyl)pyrrolidine, 56

From 3.45 g (15 mmol) of amine 52, 3.93 g (18 mmol) of di-tert-butylcarbonate, and 1.82 g (18 mmol) of triethylamine, the above procedure provided 56 (3.92 g, as an oil.

$[\alpha]_D$=−71° (C=0.65, chloroform).

$^1$H-NMR (CDCl$_3$) δ 1.05 (d, 3H, J=6.7 Hz), 1.30–1.45 (m, 12H), 1.85–2.09 (m, 2H), 2.10–2.28 (m, 1H), 2.30–2.50 (m, 2H), 2.54 and 2.64 (2×s, 3H), 2.65–2.85 and 2.89–3.06 (2×m, 1H), 3.16 (q, 1H, J=6.6 Hz), 3.75–3.91 and 3.98–4.13 (2×m, 1H), 7.15–7.35 (m, 5H).

Anal. Calcd. for C$_{20}$H$_{32}$N$_2$O$_2$ . 0.1 H$_2$O: C, 71.86; H, 9.71; N, 8.38 Found: C, 72.23; H, 10.11; N, 8.21.

EXAMPLE S-2

(3S,1'R)-3-(1'-N-tert-butoxycarbonyl-N-methylaminoethyl)-1-(S-α-methylbenzyl)pyrrolidine, 59

From 9.00 g (38.7 mmol) of amine 55, 10.15 g (46.5 mmol) of di-tert-butylcarbonate, and 4.71 g (46.5 mmol) of triethylamine, the above procedure provided 59 (10.86 g, 84%) as an oil.

$[\alpha]_D$=−28° (C=0.99, chloroform).

$^1$H-NMR (d$_6$-DMSO, 75° C.) δ 1.03 (d, 3H, J=6.7 Hz), 1.28 (d, 3H, J=6.7 Hz), 1.33–1.42 (m, 10H), 1.78–1.88 (m, 1H), 2.14–2.28 (m, 2H), 2.40 (dd, 1H, J=16.2, 7.3 Hz), 2.50 (t, 1H, J=7.8 Hz), 2.54–2.64 (m, 4H), 3.24 (q, 1H, J=6.6 Hz), 3.75–3.93 (m, 1H), 7.20–7.31 (m, 5H).

EXAMPLE S-3

(3S,1'S)-3-(1'-N-tert-butoxycarbonyl-N-methylaminoethyl)-1-(S-α-methylbenzyl)pyrrolidine, 58

From 7.13 g (31 mmol) of amine 54, 8.08 g (37 mmol) of di-tert-butylcarbonate, and 3.74 g (37 mmol) of triethylamine, the above procedure provided 58 (9.15 g, 90%) as an oil.

$[\alpha]_{D=-26}°$ (c=1.00, chloroform).

$^1$H-NMR (CDCl$_3$) δ 1.03 and 1.20 (2×d, 3H, J=6.7 and 6.1 Hz), 1.38 (d, 3H, J=6.4 Hz), 1.39–1.50 (m, 1H), 1.45 (s, 9H), 1.63–1.80 (m, 1H), 1.90–2.01 (m, 1H), 2.15–2.37 (m, 2H), 2.42–2.55 (m, 1H), 2.65 and 2.70 (2×s, 3H), 2.84–2.99 (m, 1H), 3.10–3.21 (m, 1H), 3.72–4.11 (m, 1H), 7.16–7.34 (m, 5H).

Anal. Calcd. for $C_{20}H_{32}N_2O_2 \cdot 0.30\ H_2O$: C, 71.09; H, 9.72; N, 8.29 Found: C, 71.11; H, 9.88; N, 8.45.

General Procedure for the Preparation of the 3-(1'-N-tert-butoxycarbonyl-N-methylaminoethyl)pyrrolidines, 60–63

A suspension of compound 56–59 (3 mmol) and 20% palladium-on-charcoal catalyst (0.1 g) in methanol (10 mL) was placed in a Parr shaker and hydrogenated (50 psi) until no more uptake of hydrogen was observed and thin-layer-chromatography (dichloromethane-methanol 10:1) indicated complete conversion. The suspension was filtered through a pad of Celite and the filtrate concentrated to give the product.

EXAMPLE T (3R,1'S)-3-(1'-N-tert-butoxycarbonyl-N-methylaminoethyl)pyrrolidine, 60

From 3.35 g (10 mmol) of 56, there was obtained 60 (2.20 g, 96%) as a pale yellow oil.

$[\alpha]_D = -2°$ (c=1.38, chloroform).

$^1$H-NMR (250 MHz, CDCl$_3$): 1.13 (d, 3H, J=6.7 Hz), 1.30–1.48 (m, 1H), 1.46 (s, 9H), 1.83–1.98 (m, 1H), 2.06–2.27 (m, 1H), 2.55–2.80 (m, 4H), 2.83–3.25 (m, 4H), 3.73–3.92 and 3.97–4.12 (2×m, 1H).

Anal. Calcd. for $C_{12}H_{24}N_2O_2 \cdot 0.45\ H_2O$: C, 60.96; H, 10.61; N, 11.85 Found: C, 61.27; H, 10.58; N, 11.43.

EXAMPLE T-1

(3R,1'R)-3-(1'-N-tert-butoxycarbonyl-N-methylaminoethyl) pyrrolidine, 61

From 3.19 g (9.6 mmol) of 57, there was obtained 61 (2.16 g, 99%) as a faint yellow oil which solidified upon cooling to 0° C.

$[\alpha]_D = +15°$ (c=0.38, chloroform).

$^1$H-NMR (CDCl$_3$) δ 1.09 (d, 3H, J=6.7 Hz), 1.40–1.48 (m, 1H), 1.46 (s, 9H), 1.70–1.84 (m, 1H), 2.12–2.27 (m, 1H), 2.47–2.62 (m, 1H), 2.70 and 2.73 (2×s, 3H), 2.90–3.03 (m, 2H), 3.10 (dd, 1H, J=10.8, 7.7 Hz), 3.78–3.90 and 3.98–4.10 (2×m, 2H).

Anal. Calcd. for $C_{12}H_{24}N_2O_2$: C, 63.12; H, 10.59; N, 12.27 Found: C, 63.06; H, 10.59; N, 12.26.

EXAMPLE T-2

(3S,1'R)-3-(1'-N-tert-butoxycarbonyl-N-methylaminoethyl) pyrrolidine, 63

From 10.12 g (30 mmol) of 59, there was obtained 63 (4.47 g, 64%) as a clear, colorless liquid; bp 100°–105° C., 1 mm Hg.

$[\alpha]_D = -1°$ (c=0.95, chloroform).

$^1$H-NMR (CDCl$_3$) δ 1.12 (d, 3H, J=6.7 Hz), 1.28–1.52 (m, 10H), 1.80–1.98 (m, 1H), 2.05–2.23 (m, 1H), 2.51–2.79 (m, 4H), 2.80–3.08 (m, 3H), 3.73–3.87 and 3.96–4.08 (2×m, 1H).

Anal. Calcd. for $C_{12}H_{24}N_2O_2 \cdot 0.30\ H_2O$: C, 61.66; H, 10.61; N, 11.98 Found: C, 61.62; H, 10.56; N, 12.10.

EXAMPLE T-3

(3S,1'S)-3-(1'-N-tert-butoxycarbonyl-N-methylaminoethyl)pyrrolidine, 62

From 8.16 g (25 mmol) of 58, there was obtained 62 (4.26 g, 76%) as a colorless oily liquid after vacuum distillation (bp 100°–102° C., ca 1 mm Hg) This product crystallized into a white, wax-like solid upon cooling to 0° C.

$[\alpha]_D = -12°$ (c=0.49, chloroform).

$^1$H-NMR (CDCl$_3$) δ 1.08 (d, 3H, J=6.7 Hz), 1.40–1.54 (m, 10H), 1.71–1.82 (m, 1H), 2.06–2.20 (m, 1H), 2.47–2.58 (m, 2H), 2.69 and 2.73 (2×s, 3H), 2.86–3.08 (m, 3H), 3.77–3.86 and 3.98–4.15 (2×m, 1H).

Anal. Calcd. for $C_{12}H_{24}N_2O_2 \cdot 0.17\ H_2O$: C, 62.29; H, 10.60; N, 12.11 Found: C, 62.30; H, 10.74; N, 11.93.

PREPARATION OF FINAL PRODUCTS

General Method for Coupling Pyrrolidines to the Appropriate Quinolone Nucleus and Removal of the BOC Group To the substrate (1.40–3.30 mmol) in CH$_3$CN (10–30 mL) was added triethylamine (1.10–1.40 eq) and the diastereomerically pure pyrrolidine (1.10–1.20 eq). The reaction was stirred at room temperature (0–96 hours) then warmed to reflux (6.5–48 hours). The reaction was cooled to room temperature, stirred (0–18 hours) and filtered. The filter pad was washed with CH$_3$CN and/or ether, then air dried to give pure products as solids.

The amines were deprotected by one of three methods.

Method A: The protected quinolone (2.00–3.00 mmol) was dissolved in TFA (15.0 mL). After stirring one hour at 25° C., the reaction was concentrated in vacuo. The residue was dissolved in a minimum amount of H$_2$O. Fifty percent NaOH was added to make the pH of the solution equal to 12. The homogenous solution was filtered and the filtrate was acidified with 3N HCl until the pH of the solution was equal to 8.3. The filtrate was filtered and the pad washed with a small amount of H$_2$O and/or 0.50N HCl. After drying, the solid was dissolved in concentrated HCl (14.0–40.0 mL). The acidic solution was centrifuged (little or no solid present) and the supernatant was concentrated to dryness.

Method B: The protected quinolone (1.80–3.50 mmol) was suspended in absolute EtOH (10.0–20.0 mL) and 1N HCl (5.00–10.0 mL). The reaction was warmed to reflux and became homogeneous after a short period of time. After refluxing 2–5 hours, the reaction was allowed to cool to room temperature. After 3–18 hours, any solid formed was obtained by filtration. The pad was washed sequentially with H$_2$O and/or EtOH or IPA then ether. After drying, pure product was obtained. Additional pure material could be obtained from the filtrate. If, after stirring at room temperature, no solid had formed, the reaction was concentrated in vacuo. The residue was triturated with IPA and the solid which formed was filtered, washed with isopropanol and then ether to provide the desired product.

Method C: Hydrogen chloride gas was bubbled during 3–5 minutes through a solution of the N-Boc protected compound (2.5 mmol) in dichloromethane (40 mL). A small amount of methanol was added to the reaction mixture to dissolve the material that precipitated out, and the resulting solution was stirred at room temperature for 15–20 hours. The solvent was evaporated and the residue was dissolved in hot methanol and crystallized by the addition of ether. The solid was filtered, washed with ether, and dried to provide the desired product.

EXAMPLE 1

3S,1R-1-cyclopropyl-6-fluoro-7-[3-(1-N-t-butyloxycarbonylaminoethyl)-1-pyrrolidinyl]-1,4-dihydro-4-oxo-3-quinolinecarboxylic acid The desired product (1.40 g, 92%) was obtained starting from pyrrolidine 23 and quinolone B; mp 244.5°–245° C.; $^1$H-NMR (DMSO-d$_6$) δ 1.03–1.35 (m, 7H), 1.40 (s, 9H), 1.58–1.87 (m, 1H), 1.96–2.18 (m, 1H), 2.20–2.45 (m, 1H), 3.37–3.83 (m, 6H), 6.96 (d, J=9.0 Hz, 1H), 7.02 (d, J=7.9 Hz, 1H), 7.79 (d, J=14 Hz, 1H), 8.57 (s, 1H);

Anal. [C$_{24}$H$_{30}$FN$_3$O$_5$]: (Calcd., found): C, (62.73, 62.52); H, (6.58, 6.49); N, (9.14, 9.11); F, (4.13, 4.08).

3S,1R-1-cyclopropyl-6-fluoro-7-[3-(1-aminoethyl)-1-pyrrolidinyl]-1,4-dihydro-4-oxo-3-quinolinecarboxylic acid The protecting group was removed using method A, to provide the desired product (0.94 g, 82.0%); mp >300° C.; $^1$H-NMR (NaOD+D$_2$O) δ 0.70–1.49 (m, 9H), 1.73–2.05 (m, 2H), 2.49–2.70 (m, 1H), 2.73–3.00 (m, 1H), 3.03–3.49 (m, 4H), 6.36 (d, J=7.3 Hz, 1H), 7.46 (d, J=15 Hz, 1H), 8.31 (s, 1H);

Anal. [C$_{19}$H$_{22}$FN$_3$O$_3$, 1.43 HCl, 0.71 H$_2$O]: (Calcd., found): C, (53.78, 53.78); H, (5.90, 5.83); N, (9.90, 9.81); F, (4.88, 4.66); Cl, (11.95, 11.96); [α]$_D$=+48° (c=0.97, 1N NaOH).

EXAMPLE 2

3S,1S-1-cyclopropyl-6-fluoro-7-[3-(1-N-t-butyloxy-carbonylaminoethyl)-1-pyrrolidinyl]-1,4-dihydro-4-oxo-3-quinolinecarboxylic acid The desired product (1.09 g, 85%) was obtained starting from pyrrolidine 22 and quinolone B; mp 217°–219° C.; $^1$H-NMR (CDCl$_3$) δ 1.08–1.67 (m, 16H), 1.73–2.05 (m, 1H), 2.07–2.50 (m, 2H), 3.27–3.97 (m, 6H), 4.37–4.60 (m, 1H), 6.86 (d, J=7.4 Hz, 1H), 7.91 (d, J=14 Hz, 1H), 8.68 (s, 1H);

Anal. [C$_{24}$H$_{30}$FN$_3$O$_5$, 0.28 H$_2$O]: (Calcd., found): C, (62.05, 62.06); H, (6.63, 6.51); N, (9.04, 8.92); F, (4.09, 4.19).

3S,1S-1-cyclopropyl-6-fluoro-7-[3-(1-aminoethyl)-1-pyrrolidinyl]-1,4-dihydro-4-oxo-3-quinolinecarboxylic acid The protecting group was removed using method A to provide the desired product (0.71 g, 78.1%), mp >300° C.; $^1$H-NMR (NaOD+D$_2$O) δ 0.62–1.51 (m, 9H), 1.59–1.88 (m, 1H), 1.90–2.18 (m, 1H), 2.32–2.78 (m, 2H), 2.88–3.46 (m, 4H), 6.27 (d, J=7.3 Hz, 1H), 7.37 (d, J=6.7 Hz, 1H), 8.28 (s, 1H);

Anal. [C$_{19}$H$_{22}$FN$_3$O$_3$, 1.64 HCl, 1.12 H$_2$O]: (Calcd., found): C, (51.94, 51.94); H, (5.94, 5.75); N, (9.56, 9.33); F, (4.32, 4.30); Cl, (13.23, 13.25); [α]$_D$=−62.7° (c=0.73, 1N NaOH).

EXAMPLE 3

3R,1S-1-cyclopropyl-6-fluoro-7-[3-(1-N-t-butyloxy-carbonylaminoethyl)-1-pyrrolidinyl]-1,4-dihydro-4-oxo-3-quinolinecarboxylic acid The desired product (1.15 g, 84%) was obtained starting from pyrrolidine 20 and quinolone B; mp 240°–241.5° C.; $^1$H-NMR (CDCl$_3$) δ 1.10–1.66 (m, 16H—contains 1.26 (d, J=6.5 Hz) and 1.47 (s)), 1.66–1.93 (m, 1H), 2.08–2.48 (m, 2H), 3.38–3.90 (m, 6H), 4.40–4.60 (m, 1H), 6.86 (d, J=7.3 Hz, 1H), 7.90 (d, J=14 Hz, 1H), 8.67 (s, 1H);

Anal. [C$_{24}$H$_{30}$FN$_3$O$_5$, 0.09 H$_2$O]: (Calcd., found): C, (62.51, 62.18); H, (6.60, 6.18); N, (9.11, 9.14); F, (4.12, 4.81).

3R,1S-1-cyclopropyl-6-fluoro-7-[3-(1-aminoethyl)-1-pyrrolidinyl]-1,4-dihydro-4-oxo-3-quinolinecarboxylic acid The protecting group was removed using method B to provide the desired product (0.69 g 74.8%), mp >300° C.; $^1$H-NMR (DMSO-d$_6$+heat) δ 1.08–1.23 (m, 2H), 1.23–1.53 (m, 5H), 1.67–1.97 (m, 1H), 2.03–2.26 (m, 1H), 2.35–2.63 (m, 1H), 3.17–3.83 (m, 1H), 3.40–3.57 (m, 1H), 3.57–3.92 (m, 4H), 7.10 (d, J=7.4 Hz, 1H), 7.82 (d, J=15 Hz, 1H), 8.30 (br. s., 2H), 8.59 (s, 1H);

Anal. [C$_{19}$H$_{22}$FN$_3$O$_3$ 1.00 HCl): (Calcd., found): C, (57.65, 57.53); H, (5.60, 5.86); N, (10.61, 10.51); F, (4.80, 5.00); Cl, (8.96, 8.83); [α]$_D$=−58.8° (c=0.99, 1N NaOH).

EXAMPLE 4

3R,1R-1-cyclopropyl-6-fluoro-7-[3-(1-N-t-butyloxy-carbonylaminoethyl-1-pyrrolidinyl]-1,4-dihydro-4-oxo-3-quinolinecarboxylic acid The desired product (0.97 g, 73%) was obtained starting from pyrrolidine 21 and quinolone B; mp 209.5°–211.5° C. dec.; $^1$H-NMR (CDCl$_3$) 1.10 (m, 16H—contains 1.24 (d, J=6.7 Hz) and 1.46 (s)), 1.72–2.05 (m, 1H), 2.08–2.48 (m, 2H), 3.30–3.97 (m, 6H), 4.40–4.60 (m, 1H), 6.86 (d, J=7.5 Hz, 1H), 7.90 (d, J=14 Hz, 1H), 8.67 (s, 1H);

Anal. [C$_{24}$H$_{30}$FN$_3$O$_5$, 1.79 H$_2$O]: (Calcd., found): C, (58.62, 59.01) H, (6.88, 6.87); N, (8.54, 8.48); F, (3.86, 4.15).

3R,1R-1-cyclopropyl-6-fluoro-7-[3-(1-aminoethyl)-1-pyrrolidinyl]-1,4-dihydro-4-oxo-3-quinolinecarboxylic acid The protecting group was removed using method B to provide the desired product (0.80 g, 89.6%), mp >300° C.; $^1$H-NMR (DMSO+heat) δ 1.07–1.50 (m, 7H), 1.72–2.00 (m, 1H), 2.12–2.37 (m, 1H), 2.37–2.65 (m, 1H), 3.18–3.51 (m, 2H), 3.53–3.87 (m, 4H), 7.09 (d, J=7.9 Hz, 1H), 7.82 (d, J=14 Hz, 1H), 8.18 (br. s., 1H), 8.59 (s, 1H);

Anal. [$C_{19}H_{22}FN_3O_3$, 1.00 HCl, 2.56 $H_2O$]: (Calcd., found): C, (51.63, 51.26); H, (6.41, 6.56); N, (9.51, 9.44); Cl, (8.02, 8.19); F, (4.30, 4.80); [α]$_D$=−60.3° (c=0.95 1N NaOH).

EXAMPLE 5

3S,1R-1-cyclopropyl-6-fluoro-7-[3-(1-N-t-butyloxy-carbonylaminoethyl-1-pyrrolidinyl]-1,4-dihydro-4-oxo-1,8-naphthyridine-3-carboxylic acid The desired product (0.63 g, 88%) was obtained starting from pyrrolidine 23 and guinolone A, mp 220°–220.5° C.; $^1$H-NMR (DMSO-d$_6$+heat) δ 0.97–1.27 (m, 7H), 1.39 (s, 9H), 1.53–1.83 (m, 1H), 1.95–2.17 (m, 1H), 2.17–2.43 (m, 1H), 3.40–3.83 (m, 4H), 3.83–4.13 (m, 2H), 6.98 (d, J=9.0 Hz, 1H), 7.95 (d, J=13 Hz, 1H), 8.56 (s, 1H), 15.45 (s);

Anal. [$C_{23}H_{29}FN_4O_5$]: (Calcd., found): C, (59.99, 59.75); H, (6.35, 6.37); N, (12.17, 12.21); F, (4.12, 4.29).

3S,1R-1-cyclopropyl-6-fluoro-7-[3-(1-aminoethyl)-1-pyrrolidinyl]-1,4-dihydro-4-oxo-1,8-naphthyridine-3-carboxylic acid The protecting group was removed using method B to provide the desired product (1.02 g, 74.1%), mp >300° C.; $^1$H-NMR (DMSO-d$_6$+heat) δ 0.93–1.17 (m, 2H), 1.17–1.47 (m, 5H), 1.63–1.95 (m, 1H), 2.00–2.37 (m, 1H), 2.33–2.63 (m, 1H), 3.20–3.47 (m, 1H), 3.50–3.87 (m, 3H), 3.90–4.25 (m, 2H), 8.00 (d, J=13 Hz, 1H), 8.30 (br. s., 1H), 8.58 (s, 1H);

Anal. [$C_{18}H_{21}FN_4O_3$, 1.00 HCl]: (Calcd., found): C, (54.48, 54.47); H, (5.59, 5.44); N, (14.18, 13.88); Cl, (8.93, 8.72); F, (4.79, 5.09); [α]$_D$=+3.6° (c=1.00 1N NaOH).

EXAMPLE 6

3S,1S-1-cyclopropyl-6-fluoro-7-[3-(1-N-t-butyloxy-carbonylaminoethyl)-1-pyrrolidinyl]-1,4-dihydro-4-oxo-1,8-naphthyridine-3-carboxylic acid The desired product (0.78 g, 53%) was obtained starting from pyrrolidine 22 and quinolone A; mp 208°–208.5° C. dec; $^1$H-NMR (DMSO-d$_6$+heat) δ 1.00–1.32 (m, 7H), 1.37 (s, 9H), 1.63–1.91 (m, 1H), 1.93–2.15 (m, 1H), 2.18–2.43 (m, 1H), 3.38–3.80 (m, 4H), 3.80–4.12 (m, 2H), 6.95 (d, J=8.9 Hz, 1H), 7.93 (d, J=13 Hz, 1H), 8.55 (s, 1H), 15.4 (s);

Anal. [$C_{23}H_{29}FN_4O_5$, 1.09 $H_2O$, 0.06 $CH_3CN$]: (Calcd., found): C, (57.54, 57.57); H, (6.56, 6.52); N, (11.78, 11.68); F, (3.94, 4.26).

3S,1S-1-cyclopropyl-6-fluoro-7-[3-(1-aminoethyl)-1-pyrrolidinyl]-1,4-dihydro-4-oxo-1,8-naphthyridine-3-carboxylic acid The protecting group was removed using method B to provide the desired product (0.65 g, 69.1%), mp >300° C.; $^1$H-NMR (DMSOd$_6$+heat) δ 1.00–1.50 (m, 7H), 1.65–2.00 (m, 1H), 2.10–2.35 (m, 1H), 2.37–2.67 (m, 1H), 3.17–3.87 (m, 4H), 3.90–4.20 (m, 2H), 8.00 (d, J=13 Hz, 1H), 8.23 (br. s.), 8.58 (s, 1H);

Anal. [$C_{18}H_{21}FN_4O_3$, 1.00 HCl]: (Calcd., found): C, (54.48, 54.42); H, (5.59, 5.41); N, (14.18, 13.86); Cl, (8.93, 9.10); F, (4.79, 4.88); [α]$_D$=+13.1° (c=1.00, 1N NaOH).

EXAMPLE 7

3R,1S-1-cyclopropyl-6-fluoro-7-[3-(1-N-t-butyloxycarbonylaminoethyl)-1-pyrrolidinyl]-1,4-dihydro-4-oxo-1,8-naphthyridine-3-carboxylic acid The desired product (0.76 g, 92%) was obtained starting from pyrrolidine 20 and quinolone A; mp 216.5°–217.0° C.; $^1$H-NMR (DMSO-d$_6$) δ 1.00–1.27 (m, 7H), 1.39 (s, 9H), 1.56–1.83 (m, 1H), 1.95–2.17 (m, 1H), 2.18–2.43 (m, 1H), 3.40–3.83 (m, 4H), 3.83–4.10 (m, 2H), 6.98 (d, J=8.6 Hz, 1H), 7.94 (d, J=13 Hz, 1H), 8.56 (s, 1H), 15.4 (s);

Anal. [$C_{23}H_{29}N_4O_5$]: (Calcd., found): C, (59.99, 59.75); H, (6.30, 6.20); N, (12.17, 12.03); F, (4.12, 3.85).

3R,1S-1-cyclopropyl-6-fluoro-7-[3-(1-aminoethyl)-1-pyrrolidinyl]-1,4-dihydro-4-oxo-1,8-naphthyridine-3-carboxylic acid The protecting group was removed using method B to provide the desired product (0.64 g, 88.7%), mp >300° C.; $^1$H-NMR (DMSO-d$_6$+heat) δ 0.97–1.18 (m, 2H), 1.18–1.50 (m, 5H), 1.65–1.95 (m, 1H), 2.02–2.27 (m, 1H), 2.33–2.63 (m, 1H), 3.20–3.40 (m, 1H), 3.47–3.87 (m, 3H), 3.88–4.25 (m, 2H), 8.00 (d, J=13 Hz, 1H), 8.26 (br. s.), 8.58 (s, 1H);

Anal. [$C_{18}H_{21}FN_4O_3$, 1.00 HCl, 0.22 $H_2O$]: (Calcd., found): C, (53.94, 53.95); H, (5.64, 5.51); N, (13.98, 13.95); Cl, (8.44, 8.66); F, (4.73, 4.62); [α]$_D$=−4.8° (c=1.03, 1N NaOH).

EXAMPLE 8

3R,1R-1-cyclopropyl-6-fluoro-7-[3-(1-N-t-butyloxy-carbonylaminoethyl)-1-pyrrolidinyl]-1,4-dihydro-4-oxo-1,8-naphthyridine-3-carboxylic acid The desired product (0.56 g, 81%) was obtained starting from pyrrolidine 21 and quinolone A; mp 210.0°–10.5° C.; $^1$H-NMR (DMSO) δ 1.00–1.28 (m, 7H), 1.38 (s, 9H), 1.63–1.90 (m, 1H), 1.93–2.15 (m, 1H), 2.17–2.45 (m, 1H), 3.33–3.83 (m, 4H), 3.83–4.10 (m, 2H), 6.95 (d, J=8.6 Hz, 1H), 7.95 (d, J=13 Hz, 1H), 8.56 (s, 1H), 15.4 (s);

Anal. [$C_{23}H_{29}FN_4O_5$, 0.78 $H_2O$, 0.10 $CH_3N$]: (Calcd., found): C, (58.22, 58.12); H, (6.50, 6.39); N, (12.00, 11,68); F, (3.97, 4.21).

3R,1R-1-cyclopropyl-6-fluoro-7-[3-(1-aminoethyl)-1-pyrrolidinyl]-1,4-dihydro-4-oxo-8-naphthyridine-3-carboxylic acid The protecting group was removed using method B to provide the desired compound (0.67 g, 77.1%), mp >300° C.; $^1$H-NMR (DMSO-$d_6$+heat) δ 1.00–1.47 (m, 7H), 1.68–2.00 (m, 1H), 2.11–2.35 (m, 1H), 2.35–2.67 (m, 1H), 3.17–3.87 (m, 4H), 3.90–4.17 (m, 2H), 8.00 (d, J=13 Hz, 1H), 8.30 (br. s.), 8.58 (s, 1H);

Anal. [$C_{18}H_{21}FN_4O_3$, 1.00 HCl]: (Calcd., found): C, (54.48, 54.31); H, (5.59, 5.68); N, (14.18, 14.08); Cl, (8.93, 8.58); F, (4.79, 4.44); [α]$_D$=–13.9° (c=1.09%, 1N NaOH); HPLC=99.7%.

EXAMPLE 9

3R,1R-1-cyclopropyl-6-fluoro-7-[3-(1-N-ethylaminoethyl)-1-pyrrolidinyl]-8-trifluoromethyl-1,4-dihydro-4-oxo-3-quinolinecarboxylic acid The quinolone (D, 0.90 g, 2.7 mmol), pyrrolidine (45) (0.43 g, 3.0 mmol), and triethylamine (0.42 mL) were dissolved in acetonitrile (25 mL) and heated to reflux for 20 hours. The reaction was cooled to 5° C. and the solid collected by filtration. This solid was washed with cold acetonitrile and dried under vacuum at 50° C. for 60 hours. This yielded 0.83 g of the title compound.

Calcd. for $C_{22}H_{25}F_4N_3O_3$, 0.5 H$_2$O: C, 56.89; H, 5.64; N, 9.05 Found: C, 56.98; H, 5.69; N, 9.12. $^1$H-NMR (CD$_3$OD) δ 8.63 (s, 1H), 7.76 (d, 1H, J=14.5 Hz), 4.00–3.55 (broad m, 6H), 3.20–2.90 (m, 2H), 2.65–2.50 (m, 1H), 2.25–2.10 (m, 1H), 1.90–1.80 (m, 1H), 1.40–1.10 (m, 8H), 1.00–1.85 (m, 1H), 0.80–0.70 (m, 1H).

EXAMPLE 10

3R,1S-1-cyclopropyl-6-fluoro-7-[3-(1-N-ethylaminoethyl)-1-pyrrolidinyl]-8-trifluoromethyl-1,4-dihydro-4-oxo-3-quinolinecarboxylic acid The quinolone (D, 0.90 g, 2.7 mmol), pyrrolidine (44) (0.43 g, 3.0 mmol), and triethylamine (0.42 mL) were dissolved in acetonitrile (25 mL) and heated to reflux for 20 hours. The reaction was cooled to 5° C. and the solid collected by filtration. This solid was washed with cold acetonitrile and dried under vacuum at 50° C. for 60 hours. This yielded 0.27 g of the title compound. The reaction filtrate was evaporated to a solid and triturated with water. The solid collected was dried at 50° C. for 24 hours to give an additional 0.62 g of the title compound.

Calcd. for $C_{22}H_{25}F_4N_3O_3$ · 1.14 H$_2$O C, 55.51; H, 5.78; N, 8.83 Found: C, 55.13; H, 5.37; N, 8.47. $^1$H-NMR (CD$_3$OD) δ 8.58 (s, 1H), 7.74 (d, 1H, J=14.7 Hz), 3.95–3.45 (m, 5H), 3.30–3.15 (m, 2H), 3.10–2.95 (m, 1H), 2.50–2.30 (m, 1H), 2.20–2.05 (m, 1H), 1.80–1.60 (m, 1H), 1.45–1.30 (m, 6H), 1.25–1.05 (m, 2H), 0.95–0.80 (m, 1H), 0.75–0.60 (m, 1H).

EXAMPLE 11

3S,1R-1-cyclopropyl-6-fluoro-7-[3-(1-N-ethylaminoethyl)-1-pyrrolidinyl]-8-trifluoromethyl-1,4-dihydro-4-oxo-3 -quinolinecarboxylic acid The quinolone (D, 0.90 g, 2.7 mmol), pyrrolidine (47) (0.43 g, 3.0 mmol), and triethylamine (0.42 mL) were dissolved in acetonitrile (25 mL) and heated to reflux for 20 hours. The reaction was cooled to 5° C. and the solid collected by filtration. This solid was washed with cold acetonitrile and dried under vacuum at 50° C. for 60 hours. This yielded 0.33 g of the title compound. The reaction filtrate was evaporated to a solid and triturated with water. The solid collected was dried at 50° C. for 24 hours to give an additional 0.73 g of the title compound.

Calcd. for $C_{22}H_{25}F_4N_3O_3$, 0.95 H$_2$O: C, 55.92; H, 5.74; N, 8.89 Found: C, 55.91; H, 5.70; N, 9.06. $^1$H-NMR (CD$_3$OD) δ 8.55 (s, 1H), 7.73 (d, 1H, J=14 Hz), 3.95–3.45 (m, 5H), 3.30–3.10 (m, 2H), 3.05–2.90 (m, 1H), 2.50–2.30 (m, 1H), 2.20–2.05 (m, 1H), 1.80–1.60 (m, 1H), 1.50–1.30 (broad featureless peak, 6H), 1.30–1.05 (m, 2H), 0.95–0.80 (m, 1H), 0.75–0.60 (m, 1H).

EXAMPLE 12

3S,1S-1-cyclopropyl-16-fluoro-7-[3-(1-N-ethylaminoethyl)-1-pyrrolidinyl]-8-trifluoromethyl-1,4-dihydro-4-oxo-3-quinolinecarboxylic acid The quinolone (D, 0.90 g, 2.7 mmol), pyrrolidine (46) (0.43 g, 3.0 mmol), and triethylamine (0.42 mL) were dissolved in acetonitrile (25 mL) and heated to reflux for 20 hours. The reaction was cooled to 5° C. and the solid collected by filtration. This solid was washed with cold acetonitrile and dried under vacuum at 50° C. for 60 hours. This yielded 0.92 g of the title compound.

Calcd. for $C_{22}H_{25}F_4N_3O_3$, 1.34 H$_2$O: C, 55.10; H, 5.82; N, 8.76 Found: C, 54.84; H, 5.55; N, 9.16. $^1$H-NMR (CD$_3$OD) δ 8.67 (s, 1H), 7.79 (d, 1H, 14.5 Hz), 4.00–3.55 (m, 6H), 3.20–3.10 (m, 1H), 3.10–2.90 (m, 1H), 2.65–2.50 (m, 1H), 2.30–2.15 (m, 1H), 1.90–1.70 (m, 1H), 1.40–1.10 (m, 8H), 1.00–0.90 (m, 1H), 0.85–0.70 (m, 1H).

EXAMPLE 13

3R,1R-1-cyclopropyl-6-fluoro-7-[3-(1-N-ethylaminoethyl-1-pyrrolidinyl)-1,4-dihydro-4-oxo-3-quinolinecarboxylic acid The quinolone (B, 0.50 g, 1.9 mmol), pyrrolidine (45) (0.30 g, 2.1 mmol), and triethylamine (0.30 mL) were dissolved in acetonitrile (7 mL) and heated to reflux for 20 hours. The reaction became very viscous upon heating and an additional 5 mL of acetonitrile was added. The reaction was cooled to 5° C. and the solid collected by filtration. This solid was washed with cold acetonitrile and dried under vacuum at 50° C. for 18 hours. This yielded 0.70 g of the title compound.

Calcd. for $C_{21}H_{26}FN_3O_3$, 0.33 HF: C, 64.01; H, 6.73; N, 10.66; F, 6.41 Found: C, 63.73; H, 6.70; N, 10.55; F, 6.17. $^1$H-NMR (TFA) δ 9.18 (s, 1H), 8.13 (d, 1H, J=13.5 Hz), 7.33 (d, 1H, J=6.7 Hz), 7.20–6.90 (broad m, 1H), 4.30–4.15 (m, 1H), 4.10–3.30 (m, 7H), 3.00–2.80 (m, 1H), 2.70–2.55 (m, 1H), 2.20–2.05 (m, 1H), 1.75–1.60 (m, 5H), 1.53 (t, 3H, J=7.1 Hz), 1.50–1.30 (m, 2H).

EXAMPLE 14

3R,1S-1-cyclopropyl-6-fluoro-7-[3-(1-N-ethylaminoethyl-1-pyrrolidinyl)-1,4-dihydro-4-oxo-3-quinolinecarboxylic acid The quinolone (B, 0.50 g, 1.9 mmol), pyrrolidine (44) (0.30 g, 2.1 mmol), and triethylamine (0.30 mL) were dissolved in acetonitrile (7 mL) and heated to reflux for 20 hours. The reaction became very viscous upon heating and an additional 5 mL of acetonitrile was added. The reaction was cooled to 5° C. and the solid collected by filtration. This solid was washed with cold acetonitrile and dried under vacuum at 50° C. for 18 hours. This yielded 0.63 g of the title compound.

Calcd. for $C_{21}H_{26}FN_3O_3$, 0.6 HF: C, 63.14; H, 6.71; N, 10.52; F, 7.61 Found: C, 62.80; H, 6.66; N, 10.73; F, 7.63. $^1$H-NMR (CD$_3$OD) δ 8.45 (s, 1H), 7.51 (d, 1H, J=14.4 Hz), 3.85–3.75 (m, 1H), 3.70–3.40 (m, 4H), 3.25–2.85 (m, 3H), 3.55–3.45 (m, 1H), 2.25–2.10 (m, 1H), 1.95–1.80 (m, 1H), 1.40–1.25 (m, 8H), 1.20–1.10 (m, 2H).

EXAMPLE 15

3S,1R-1-cyclopropyl-6-fluoro-7 -[3-(1-N-ethylaminoethyl)-1-pyrrolidinyl] -1,4-dihydro-4-oxo-3-quinolinecarboxylic acid The quinolone (B, 0.50 g, 1.9 mmol), pyrrolidine (47) (0.30 g, 2.1 mmol), and triethylamine (0.30 mL) were dissolved in acetonitrile (7 mL) and heated to reflux for 20 hours. The reaction became very viscous upon heating and an additional 5 mL of acetonitrile was added. The reaction was cooled to 5° C. and the solid collected by filtration. This solid was washed with cold acetonitrile and dried under vacuum at 50° C. for 18 hours. This yielded 0.63 g of the title compound.

Calcd. for $C_{21}H_{26}FN_3O_3$, 0.75 HF: C, 62.67; H, 6.70; N, 10.44; F, 8.26 Found: C, 62.74; H, 6.72; N, 10.71; F, 8.20. $^1$H-NMR (TFA) δ 9.18 (s, 1H), 8.13 (d, 1H, J=13.5 Hz), 7.34 (d, 1H, 7.1 Hz), 7.10–6.90 (broad m, 1H), 4.45–4.30 (m, 1H), 4.05–3.60 (m, 5H), 3.60–3.50 (m, 1H), 3.50–3.30 (m, 1H), 3.00–2.75 (m, 1H), 2.55–2.40 (m, 1H), 2.20–1.95 (m, 1H), 1.70–1.55 (m, 5H), 1.51 (t, 3H, J=7.2 Hz), 1.45–1.30 (m, 2H).

EXAMPLE 16

3S,1S-1-cyclopropyl-6-fluoro- 7-[3-(1-N-ethylaminoethyl)-1-pyrrolidinyl] -1,4-dihydro-4-oxo-3-quinolinecarboxylic acid The quinolone (B, 0.50 g, 1.9 mmol), pyrrolidine (46) (0.30 g, 2.1 mmol), and triethylamine (0.30 mL) were dissolved in acetonitrile (7 mL) and heated to reflux for 20 hours. The reaction became very viscous upon heating and an additional 5 mL of acetonitrile was added. The reaction was cooled to 5° C. and the solid collected by filtration. This solid was washed with cold acetonitrile and dried under vacuum at 50° C. for 18 hours. This yielded 0.69 g of the title compound.

Calcd. for $C_{21}H_{26}FN_3O_3$, 0.6 HF: C, 63.14; H, 6.71; N, 10.52; F, 7.61 Found: C, 63.07; H, 6.73; N, 10.72; F, 7.85.

EXAMPLE 17

3R,1R-1-cyclopropyl-6-fluoro- 7-[3-(1-N-ethylaminoethyl)-1-pyrrolidinyl] -8-methoxy-1,4-dihydro-4-oxo-3-quinolinecarboxylic acid The 1-cyclopropyl-6,8-difluoro-8-methoxy-1,4 -dihydro-4-oxo-3-quinolinecarboxylic acid (E) borondifluoride complex (1.20 g, 3.5 mmol), and pyrrolidine (45) (1.00 g, 7.0 mmol) were dissolved in acetonitrile (20 mL) and stirred for four hours, then allowed to stand for 96 hours. The reaction mixture was evaporated to an oil and dissolved in 95% ethanol (25 mL) containing 5 mL of triethylamine and heated to reflux for four hours then allowed to stand for 24 hours. The mixture was diluted with 300 mL of ethanol and evaporated and redissolved in water (50 mL) and reevaporated to an oil. This oil was purified by flash chromatography using silica gel eluting with methylene chloride (1900 mL), 2.6% NH$_3$ in methanol (95 mL), water (5 mL). The appropriate fractions were combined and evaporated to give the title compound (0.96 g).

Calcd. for $C_{22}H_{28}FN_3O_4 \cdot 0.84$ CH$_2$Cl$_2$ C, 56.12; H, 6.12; N, 8.60; Found: C, 56.80; H, 6.29; N, 8.86. $^1$H-NMR (CD$_3$OD) δ 8.67 (s, 1H), 7.59 (d, 1H, J=14 Hz), 4.10–3.95 (m, 1H), 3.90–3.75 (m, 1H), 3.70–3.55 (m, 2H), 3.42 (s, 3H), 3.42–3.25 (m, 2H, underlies singlet and CD$_3$OD peak), 3.20–3.05 (m, 1H), 3.15–2.95 (m, 1H), 2.65–2.45 (m, 1H), 2.25–2.10 (m, 1H), 1.90–1.70 (m, 1H), 1.40–1.30 (m, 6H), 1.30–0.95 (m, 3H), 0.90–0.70 (m, 1H).

EXAMPLE 18

3R,1S-1-cyclopropyl-6-fluoro- 7-[3-(1-N-ethylaminoethyl)-1-pyrrolidinyl] -8-methoxy-1,4,-dihydro-4-oxo-3-quinolinecarboxylic acid Using pyrrolidine 44, the procedure described above was employed to prepare 0.78 g of the title compound.

Calcd. for $C_{22}H_{28}FN_3O_4 \cdot 1.22$ CH$_2$Cl$_2$: C, 53.52; H, 5.89; N, 8.06; Found: C, 53.50; H, 6.04; N, 8.27. $^1$H-NMR (CD$_3$OD) δ 8.70 (s, 1H), 7.55 (d, 1H, J=13.9 Hz), 4.15–4.05 (m, 1H), 3.90–3.70 (m, 2H), 3.80–3.55 (m, 1H), 3.55–3.40 (m and s, 4H, singlet at 3.50), 3.40–3.35 (m, 1H, overlapped with CD$_3$OD peak), 3.35–3.20 (m, 1H), 3.20–3.05 (m, 1H), 2.55–2.40 (m, 1H), 2.25–2.10 (m, 1H), 1.90–1.70 (m, 1H), 1.45–1.30 (m, 6H), 1.30–1.20 (m, 1H), 1.20–1.00 (m, 2H), 0.95–0.80 (m, 1H).

EXAMPLE 19

3S,1R-1-cyclopropyl-6-fluoro-7-[ 3-(1-N-ethylaminoethyl)-1-pyrrolidinyl] -8-methoxy-1,4-dihydro-4-oxo-3-quinolinecarboxylic acid Using pyrrolidine 47, the procedure described above was employed to prepare 1.14 g of the title compound.

Calcd. for $C_{22}H_{28}FN_3O_4 \cdot 0.21$ CH$_2$Cl$_2$: C, 6.28; H, 6.58; N, 9.58. Found: C, 61.24; H, 6.70; N, 9.71. $^1$H-NMR (CD$_3$OD) δ 8.57 (s, 1H), 7.59 (d, 1H, J=13.9 Hz), 4.04–3.90 (m, 1H), 3.85–3.65 (m, 2H), 3.60–3.45 (m, 1H), 3.25 (s, 3H), 3.20–3.05 (m, 3H), 3.05–2.95 (m, 1H), 2.40–2.10 (m, 2H), 1.80–1.60 (m, 1H), 1.45–1.30 (m, 6H), 1.25–1.10 (m, 2H), 1.10–0.95 (m, 1H), 0.80–0.65 (m, 1H).

EXAMPLE 20

3S,1S-1-cyclopropyl-6-fluoro-7-[3 -(1-N-ethylaminoethyl)-1-pyrrolidinyl]- 8-methoxy-1,4-dihydro-4-oxo-3-quinolinecarboxylic acid Using pyrrolidine 46, the procedure described above was employed to prepare 0.93 g of the title compound.

Calcd. for $C_{22}H_{28}FN_3O_4 \cdot 0.18$ CH$_2$Cl$_2$: C, 61.56; H, 6.61; N, 9.71. Found: C, 61.55; H, 6.69; N, 9.79. MS (EI) 417 (M+), 372, 357, 313, 287, 72 (base). $^1$H-NMR (CD$_3$OD) δ 8.60 (s, 1H), 7.58 (d, 1H, J=13.7 Hz), 4.10–3.95 (m, 1H), 3.85–3.70 (m, 1H), 3.70–3.50 (m, 2H), 3.31 (s, 3H), 3.30–3.20 (m, 2H), 3.20–3.10 (m, 1H), 3.05–2.90 (m, 1H), 2.65–2.45 (m, 1H), 2.20–2.05 (m, 1H), 1.85–1.65 (m, 1H), 1.36 (t, 3H, J=7.1 Hz), 1.30 (t, 3H, J=6.7 Hz), 1.25–1.05 (m, 2H), 1.05–0.95 (m, 1H), 0.85–0.70 (m, 1H).

EXAMPLE 21

3R,1S-1-cyclopropyl-6-fluoro-7-[3-(1-N-tert-butoxycarbonyl-N-methylaminoethyl)-1-pyrrolidinyl]-1,4-dihydro-4-oxo-1,8-naphthyridine-3-carboxylic acid From 0.85 g (3 mmoL) of 7-chloro-1,8-naphthyridine A, 0.70 g (3.1 mmol) of pyrrolidine 60, and 0.46 g (4.5 mmol) of triethylamine, there was obtained 0.84 g (59%) of the title compound after column chromatography (silica gel, dichloromethane/methanol 20:1); mp 233°–234° C.
$[\alpha]_D = -48°$ (c=0.56, chloroform).
$^1$H-NMR (250 MHz, CDCl$_3$) δ 0.99–1.10 (m, 2H), 1.18–1.26 (m, 5H), 1.43 and 1.46 (2×s, 9H), 1.68–1.87 (m, 1H), 2.07–2.23 (m, 1H), 2.38–2.60 (m, 1H), 2.78 (br. s, 3H), 3.40–3.68 (m, 2H), 3.72–4.34 (m, 4H), 7.89 (d, 1H, J=12.5 Hz), 8.61 (s, 1H), 15.12–15.25 (m, 1H).
Anal. Calcd. for C$_{24}$H$_{31}$FN$_4$O$_5$: C, 60.75; H, 6.58; N, 11.81. Found: C, 60.67; H, 6.87; N, 11.50.

3R,1S-1-cyclopropyl-6-fluoro-7-[3-(1-N-methylaminoethyl)-1-pyrrolidinyl]-1,4-dihydro-4-oxo-1,8-naphthyridine-3-carboxylic acid From 0.75 g (1.6 mmol) of the above protected derivative, the title compound (0.44 g) was obtained using Method C as an off-white solid; mp >280° C.
$^1$H-NMR (TFA) δ 1.20–1.35 (m, 2H), 1.47–1.60 (m, 2H), 1.65 (dist. d, 3H, J=5.8 Hz), 1.90–2.20 (m, 1H), 2.35–2.55 (m, 1H), 2.85–3.10 (m, 1H), 3.04 (s, 3H), 3.60–3.79 (m, 1H), 3.82–4.20 (m, 3H), 4.26–4.48 (m, 1H), 4.51–4.78 (m, 1H), 7.20–7.55 (m, 1H), 8.11 (d, 1H, J=11.6 Hz), 9.16 (s, 1H).
Anal. Calcd. for C$_{19}$H$_{23}$FN$_4$O$_3$.1.0 HCl.0.2 H$_2$O: C, 55.06; H, 5.93; N, 13.52; Cl, 8.55 Found: C, 54.74; H, 5.79; N, 12.89; Cl, 9.24.

EXAMPLE 22

3R,1R-1-cyclopropyl-6-fluoro-7-[3-(1-N-tert-butoxycarbonyl-N-methylaminoethyl)-1-pyrrolidinyl]-1,4-dihydro-4-oxo-1,8-naphthyridine-3-carboxylic acid From 0.73 g (2.6 mmol) of 7-chloro-1,8-naphthyridine A, 0.60 g (2.6 mmol) of pyrrolidine 61, and 0.38 g (3.8 mmol) of triethylamine, there was obtained 1.03 g (84%) of the title compound after column chromatography (silica gel, dichloro-methane/methanol 10:1); mp 212°–213° C.
$[\alpha]_D = -13°$ (C 1.00, EtOH).
$^1$H-NMR (CDCl$_3$) δ 0.90–1.10 (m, 2H), 1.12–1.30 (m, 5H), 1.49 (s, 9H), 1.70–1.92 (m, 1H), 1.94–2.15 (m, 1H), 2.30–2.55 (m, 1H), 2.78 and 2.81 (2×s, 3H), 3.35–3.55 (m, 1H), 3.55–3.67 (m, 1H), 3.67–3.88 (m, 1H), 3.88–4.15 and 4.17–4.30 (m, 3H), 7.90 (d, 1H, J=12.6 Hz), 8.62 (s, 1H), 14.55–14.62 (m, 1H).
Anal. Calcd. for C$_{24}$H$_{31}$FN$_4$O$_5$.0.40 H$_2$O: C, 59.84; H, 6.65; N, 11.63 Found: C, 59.96; H, 6.48; N, 11.54.

3R,1R-1-cyclopropyl-6-fluoro-7-[3-(1-N-methylaminoethyl)-1-pyrrolidinyl]-1,4-dihydro-4-oxo-1,8-naphthyridine-3-carboxylic acid Using Method B on the above protected derivative (1.00 g, 2.1 mmol), there was obtained the title compound (0.85 g) as an off-white solid; mp >280° C.
$^1$H-NMR (TFA) δ 1.20–1.40 (m, 2H), 1.45–1.75 (m, 5H), 1.97–2.30 (m, 1H), 2.50–2.70 (m, 1H), 2.80–3.18 (m, 1H), 3.05 (s, 3H), 3.53–4.23 (m, 4H), 4.30–4.60 (m, 2H), 7.20–7.50 (m, 1H), 8.12 (d, 1H, J=11.6 Hz), 9.18 (s, 1H).
Anal. Calcd. for C$_{19}$H$_{23}$FN$_4$O$_3$ . 1.0 HCl . 0.75 H$_2$O: C, 53.77; H, 6.06; N, 13.20; Cl, 8.35; F, 4.48 Found: C, 53.70; H, 5.82; N, 13.09; Cl, 8.68; F, 4.48.

EXAMPLE 23

3S,1R-1-cyclopropyl-6-fluoro-7-[3-(1-N-tert-butoxycarbonyl-N-methylaminoethyl)-1-pyrrolidinyl]-1,4-dihydro-4-oxo-1,8-naphthyridine-3-carboxylic acid From 0.76 g (2.7 mmol) of 7-chloro-1,8-naphthyridine A, 0.75 g (3.3 mmol) of pyrrolidine 63, and 0.41 g (4.1 mmol) of triethylamine, there was obtained 0.77 g (60%) of the title compound. Concentration of the filtrate and washings provided additional product (0.40 g, 31%); mp 232°–233° C.
$[\alpha]_D = 43°$ (c=0.50, chloroform).
$^1$H-NMR (CDCl$_3$) δ 0.99–1.08 (m, 2H), 1.19–1.27 (m, 5H), 1.42 and 1.46 (2×s, 9H), 1.65–1.80 (m, 1H), 2.07–2.20 (m, 1H), 2.36–2.50 (m, 1H), 2.77 and 2.80 (2×s, 3H), 3.75–4.13 (m, 4H), 7.92 (d, 1H, J=12.4 Hz), 8.64 (s, 1H), 15.20 and 15.24 (2×s, 1H).
Anal. Calcd. for C$_{24}$H$_{31}$FN$_4$O$_5$ . ⅔ H$_2$O: C, 59.26; H, 6.70; N, 11.51 Found: C, 59.24; H, 6.41; N, 11.44.

3S,1R-1-cyclopropyl-6-fluoro-7-[3-(1-N-methylaminoethyl)-1-pyrrolidinyl]-1,4-dihydro-4-oxo-1,8-naphthyridine-3-carboxylic acid Using Method C on 1.20 g (2.5 mmol) of the above protected derivative, there was obtained the title compound (1.07 g); mp >280° C.
$^1$H-NMR (250 MHz, d$_6$-DMSO+TFA): 0.97–1.30 (m, 7H), 1.70–1.86 (m, 1H), 2.05–2.19 (m, 1H), 2.40–2.70 (m, 1H), 2.67 and 2.76 (2×s, 3H), 3.24–3.39 (m, 1H), 3.43–3.78 (m, 3H), 3.90–4.01 1H), 4.04–4.20 (m, 1H), 8.11 (d, 1H, J=13.0 Hz), 8.72 (s, 1H).
Anal. Calcd. for C$_{19}$H$_{23}$FN$_4$O$_3$ . 1.0 HCl . 0.6 H$_2$O: C, 54.12; H, 6.02; N, 13.29; F, 4.51 Found: C, 53.94; H, 6.39; N, 12.90; F, 4.19.

EXAMPLE 24

3S,1S-1-cyclopropyl-6-fluoro-7-[3-(1-N-tert-butoxycarbonyl-N-methylaminoethyl)-1-pyrrolidinyl]-1,4-dihydro-4-oxo-1,8-naphthyridine-3-carboxylic acid From 0.71 g (2.5 mmol) of 7-chloro-1,8-naphthyridine A, 0.70 g (3.1 mmol) of pyrrolidine 62, and 0.40 g (4.0 mmol) of triethylamine, there was obtained 0.98 g (83%) of the title compound; mp 218.0°–219.5° C.
$[\alpha]_D = 28°$ (C=1.04, chloroform).
$^1$H-NMR (CDCl$_3$) δ 1.02–1.07 (m, 2H), 1.18–1.26 (m, 5H), 1.48 (s, 9H), 1.75–1.93 (m, 1H), 1.97–2.15 (m, 1H), 2.36–2.56 (m, 1H), 2.77 and 2.81 (2×s, 3H), 3.41–3.56

(m, 1H), 3.58–3.67 (m, 1H), 3.70–3.84 (m, 1H), 3.93–4.34 (m, 3H), 7.95 (d, 1H, J=12.5 Hz), 8.66 (s, 1H), 15.15–15.23 (m, 1H).

Anal. Calcd. for $C_{24}H_{31}FN_4O_5 \cdot 0.2\ H_2O$: C, 60.29; H, 6.62; N, 11.72 Found: C, 59.91; H, 6.74; N, 11.67.

3S,1S-1-cyclopropyl-6-fluoro-7-[3-(1-N-methylaminoethyl)-1-pyrrolidinyl]-1,4-dihydro-4-oxo-1,8-naphthyridine-3-carboxylic acid Using Method B on 1.20 g (2.5 mmol) of the above protected derivative there was obtained the title compound (0.75 g). Concentration of the mother liquor provided additional product (0.28 g); mp >280° C.

$[\alpha]_D = 20°$ (c=1.08, 1N NaOH).

$^1$H-NMR (CDCl$_3$) δ 1.01–1.10 (m, 2H), 1.15–1.25 (m, 2H), 1.29 (d, 3H, J=6.4 Hz), 1.78–1.99 (m, 1H), 2.22–2.37 (m, 1H), 2.50–2.70 (m, 1H), 2.58 (s, 3H), 3.30–3.60 (m, 2H), 3.62–3.80 (m, 2H), 3.92–4.10 (m, 2H), 7.92 (d, 1H, J=12.7 Hz), 8.53 (s, 1H), 8.98–9.16 (m, 1H), 9.17–9.30 (m, 1H), 15.37 (br. s, 1H).

Anal. Calcd. for $C_{19}H_{23}FN_4O_3 \cdot 1.0\ HCl \cdot 0.5\ H_2O$: C, 54.35; H, 6.00; N, 13.34; Cl, 8.44 Found: C, 54.47; H, 5.97; N, 13.28, Cl, 8.48.

EXAMPLE 25

3R,1S-1-cyclopropyl-6-fluoro-7-[3-(1-N-tert-butoxycarbonyl-N-methylaminoethyl)-1-pyrrolidinyl]-8-chloro-1,4-dihydro-4-oxo-3-quinolinecarboxylic acid From 0.90 g (3.0 mmol) of quinolone C, 0.70 g (3.1 mmol) of pyrrolidine 60, and 0.61 g (6.0 mmol) of triethylamine, there was obtained 1.22 g (80%) of the title compound after recrystallization from dichloromethane/heptane.

$[\alpha]_D = -180°$ (c=1.05, chloroform).

$^1$H-NMR (CDCl$_3$) δ 0.84–0.95 (m, 1H), 0.96–1.09 (m, 1H), 1.23 (dist. d, 3H, J=5.0 Hz), 1.30–1.58 (m, 2H), 1.45 (s, 9H), 1.62–1.81 (m, 1H), 2.06–2.21 (m, 1H), 2.37–2.57 (m, 1H), 2.76 and 2.78 (2×s, 3H), 3. 35–3.85 (m, 3H), 3.93–4.17 (m, 2H), 4.22–4.39 (m, 1H), 7.81 and 7.83 (2×d, 1H, J=13.4 Hz), 8.83 (s, 1H), 14.67 and 14.71 (2×br. s, 1H).

Anal. Calcd. for $C_{25}H_{31}ClFN_3O_5$: C, 59.11; H, 6.15; N, 8.27; Cl, 6.98 Found: C, 59.03; H, 6.21; N, 8.22; Cl, 7.17.

3R,1S-1-cyclopropyl-6-fluoro-7-[3-(1-N-methylaminoethyl)-1-pyrrolidinyl]-8-chloro-1,4-dihydro-4-oxo-3-quinolinecarboxylic acid Using 1.15 g (2.3 mmol) of the above quinolone, hydrolysis of the tert-butoxycarbonyl group according to general Method C provided the title compound (0.10 g) as the hydrochloride salt.

$^1$H-NMR (TFA) δ 1.30–1.47 (m, 2H), 1.56–1.84 (m, 5H), 2.01–2.22 (m, 1H), 2.40–2.59 (m, 1H), 2.83–3.15 (m, 4H), 3.57–3.77 (m, 1H), 3.80–4.10 (m, 4H), 4.23–4.50 (m, 1H), 7.20–7.60 (br m, 1H), 8.16 (br d, 1H, J=13 Hz), 9.18 (s, 1H), 11.62 (m, 1H).

EXAMPLE 26

3R,1R-1-cyclopropyl-6-fluoro-7-[3-(1-N-tert-butoxycarbonyl-N-methylaminoethyl)-1-pyrrolidinyl]-8-chloro-1,4-dihydro-4-oxo-3-quinolinecarboxylic acid From 0.99 g (3.3 mmol) of quinolone C, 0.75 g (3.3 mmol) of pyrrolidine 61, and 0.51 g (5.0 mmol) of triethylamine, there was obtained 1.66 g (99%) of the title compound after column chromatography (silica gel, dichloromethane/methanol 10:1).

$[\alpha]_D = -146°$ (C=0.50, EtOH).

$^1$H-NMR (CDCl$_3$) δ 0.80–1.08 (m, 2H), 1.10–1.35 (m, 2H), 1.16 (d, 3H, J=6.7 Hz), 1.48 (s, 9H), 1.67–1.85 (m, 1H), 1.90–2.15 (m, 1H), 2.30–2.50 (m, 1H), 2.70–2.83 (m, 3H), 3.42–3.60 (m, 3H), 3.75–4.16 (m, 2H), 4.18–4.37 (m, 1H), 7.91 (d, 1H, J=13.3 Hz), 8.86 (s, 1H), 14.60–14.80 (m, 1H).

Anal. Calcd. for $C_{25}H_{31}ClFN_3O_5 \cdot 0.20\ H_2O$: C, 58.69; H, 6.19; N, 8.21 Found: C, 58.66; H, 5.98; N, 8.03.

3R,1R-1-cyclopropyl-6-fluoro-7-[3-(1-N-methylaminoethyl)-1-pyrrolidinyl]-8-chloro-1,4-dihydro-4-oxo-3-quinolinecarboxylic acid Using Method B on 1.58 g (3.1 mmol) of the above protected quinolone, the title compound was obtained (0.79 g) as a solid; mp >280° C.

$[\alpha]_D = -109°$ (C=0.93, methanol).

$^1$H-NMR (CD$_3$OD) δ 0.89–1.10 (m, 2H), 1.16–1.45 (m, 2H), 1.40 (d, 3H, J=6.6 Hz), 1.83–2.00 (m, 1H), 2.26–2.40 (m, 1H), 2.55–2.70 (m, 1H), 2.77 (s, 3H), 3.28–3.44 (m, 2H), 3.60–3.69 (m, 3H), 3.91–4.02 (m, 1H), 4.39–4.48 (m, 1H), 7.84 (d, 1H, J=13.3 Hz), 8.91 (s, 1H).

Anal. Calcd. for $C_{20}H_{23}ClFN_3O_3 \cdot 1.0\ HCl \cdot 1.0\ H_2O$: C, 51.96; H, 5.67; N, 9.09; Cl, 15.34 Found: C, 52.05; H, 5.73; N, 9.22; Cl, 15.42.

EXAMPLE 27

3R,1S-1-cyclopropyl-6-fluoro-7-[3-(1-N-tert-butoxycarbonyl-N-methylaminoethyl)-1-pyrrolidinyl]-8-trifluoromethyl-1,4-dihydro-4-oxo-3-quinolinecarboxylic acid From 1.00 g (3.0 mmol) of quinolone D, 0.71 g (3.1 mmol) of pyrrolidine 60, and 0.61 g (6.0 mmol) of triethylamine, there was obtained 1.31 g (81%) of the title compound after recrystallization from dichloromethane/heptane; mp 175°–177° C.

$[\alpha]_D = -332°$ (C=0.13, chloroform)

$^1$H-NMR (CDCl$_3$) δ 0.70–0.83 (m, 1H), 0.85–1.02 (m, 1H), 1.17–1.38 (m, 2H), 1.22 (d, 3H, J=6.7 Hz), 1.46 (s, 9H), 1.65–1.80 (m, 1H), 2.05–2.19 (m, 1H), 2.37–2.50 (m, 1H), 2.75 and 2.76 (2×s, 3H), 3.50–4.32 (m, 6H), 7.90 and 7.93 (2×d, 1H, J=14.6 Hz), 8.77 (s, 1H), 14.76–14.82 (m, 1H).

Anal. Calcd. for $C_{26}H_{31}F_4N_3O_5 \cdot 0.50\ H_2O$: C, 56.72; H, 5.86; N, 7.63 Found: C, 56.63; H, 5.64; N, 7.56.

3R,1S-1-cyclopropyl-6-fluoro-7-[3-(1-N-methylaminoethyl)-1-pyrrolidinyl]-8-trifluoromethyl-1,4-dihydro-4-oxo-3-quinolinecarboxylic acid Using Method B on 1.10 g (2.0 mmol) of the above protected quinolone, there was obtained the title compound (0.94 g); mp 210°–212° C.

$[\alpha]_D = -234°$ (c=1.03, methanol).

$^1$H-NMR (CD$_3$OD) δ 0.88–1.10 (m, 2H), 1.22–1.37 (m, 2H), 1.43 (d, 3H, J=6.3 Hz), 1.81–2.00 (m, 1H), 2.18–2.31 (m, 1H), 2.60–2.90 (m, 1H), 2.77 (s, 3H), 3.35–3.50 (m, 1H), 3.63–4.20 (m, 5H), 7.71 (d, 1H, J=14.3 Hz), 8.85 (s, 1H).

Anal. Calcd. for $C_{21}H_{23}F_4N_3O_3 \cdot 1.0$ HCl $\cdot 1.5$ H$_2$O: C, 49.96; H, 5.39; N, 8.32; Cl, 7.02; F, 15.05 Found: C, 49.84; H, 5.12; N, 8.56; Cl, 7.81; F, 14.67.

EXAMPLE 28

3R,1R-1-cyclopropyl-6-fluoro-7
-[3-(1-N-tert-butoxycarbonyl-N-methylaminoethyl)-
1-pyrrolidinyl]-8-trifluoromethyl-1,4-dihydro-4-oxo-
3-quinolinecarboxylic acid From 1.03 g (3.1 mmol) of quinolone D, 0.74 g (3.2 mmol) of pyrrolidine 61, and 0.61 g (6.0 mmol) of triethylamine, there was obtained 1.15 g (69%) of the title compound after successive column chromatography (silica gel, dichloromethane/methanol 40:1) and recrystallization from dichloro-methane/heptane.
$[\alpha]_D = -238°$ (c=0.10, chloroform).
$^1$H-NMR (CDCl$_3$) δ 0.75–1.10 (m, 2H), 1.12–1.40 (m, 2H), 1.19 (d, 3H, J=6.5 Hz), 1.49 (s, 9H), 1.70–1.94 (m, 1H), 1.97–2.10 (m, 1H), 2.36–2.50 (m, 1H), 2.77 and 2.80 (2×s, 3H), 3.55–4.30 (m, 6H), 7.89 (d, 1H, J=14.3 Hz), 8.78 (s, 1H), 14.73–14.78 (m, 1H).
Anal. Calcd. for $C_{26}H_{31}F_4N_3O_5 \cdot 0.30$ H$_2$O: C, 57.10; H, 5.82; N, 7.68; F, 13.89 Found: C, 57.14; H, 5.61; N, 7.42; F, 13.71.

3R,1R-1-cyclopropyl-6-fluoro-7-[
3-(1-N-methylaminoethyl)-1-pyrrolidinyl]
-8-trifluoromethyl-1,4-dihydro-4-oxo-3-
quinolinecarboxylic acid Using Method B on 1.05 g (1.93 mmol) of the above protected quinolone, there was obtained the title compound (0.93 g) as a light yellow solid; mp 261°–262° C.
$[\alpha]_D = -259°$ (C=0.72, methanol).
$^1$H-NMR (CD$_3$OD) δ 0.80–0.95 (m, 1H), 0.96–1.09 (m, 1H), 1.20–1.45 (m, 2H), 1.39 (d, 3H, J=6.6 Hz), 1.80–2.00 (m, 1H), 2.26–2.40 (m, 1H), 2.56–2.70 (m, 1H), 2.77 (s, 3H), 3.33–3.46 (m, 1H), 3.70–3.93 (m, 3H), 3.97–4.14 (m, 2H), 7.84 (d, 1H, J=14.4 Hz), 8.86 (s, 1H).
Anal. Calcd. for $C_{21}H_{23}F_4N_3O_3 \cdot 1.0$ HCl $\cdot 1.1$ H$_2$O: C, 50.68; H, 5.31; N, 8.44; Cl, 7.12; F, 15.27 Found: C, 50.35; H, 5.25; N, 8.52; Cl, 7.53; F, 15.43.

EXAMPLE 29

3S,1R-1-cyclopropyl,6-fluoro-7-[
3-(1-N-tert-butoxycarbonyl-N-methylaminoethyl)-1
-pyrrolidinyl]-8-trifluoromethyl-1,4
-dihydro-4-oxo-3-quinolinecarboxylic acid From 0.90 g (2.7 mmol) of quinolone D, 0.75 g (3.3 mmol) of pyrrolidine 63, and 0.41 g (4.1 mmol) of triethylamine, there was obtained 0.88 g (60%) of the title compound. Concentration of the filtrate and washings provided additional product (0.42 g, 29%); mp 188°–189° C.
$[\alpha]_D = +224°$ (C=0.43, chloroform).
$^1$H-NMR (CDCl$_3$) δ 0.70–0.82 (m, 1H), 0.83–1.01 (m, 1H), 1.18–1.35 (m, 2H), 1.22 (d, 3H, J=6.7 Hz), 1.46 (s, 9H), 1.64–1.84 (m, 1H), 2.07–2.19 (m, 1H), 2.36–2.52 (m, 1H), 2.74 (s, 3H), 3.50–4.32 (m, 6H), 7.91 and 7.93 (2×d, 1H, J=14.2 and 14.7 Hz), 8.76 (s, 1H), 14.70–14.82 (m, 1H).
Anal. Calcd. for $C_{26}H_{31}F_4N_3O_5 \cdot 0.30$ H$_2$O: C, 57.10; H, 5.82; N, . 7.68; F, 13.89 Found: C, 57.38; H, 5.67; N, 7.70; F, 13.54.

3S, 1R-1-cyclopropyl-6-fluoro-7
-[3-(1-N-methylaminoethyl)-1-pyrrolidinyl]
-8-trifluoromethyl-1,4-dihydro-4-oxo-3-
quinolinecarboxylic acid Using Method B on 1.20 g (2.2 mmol) of the above protected quinolone, there was obtained the title compound (0.86 g); mp 218°–219° C.
$^1$H-NMR (d$_6$-DMSO) δ 0.80–0.91 (m, 1H), 0.92–1.07 (m, 1H), 1.09–1.32 (m, 2H), 1.28 (d, 3H, J=6.3 Hz), 1.65–1.73 (m, 1H), 2.02–2.21 (m, 1H), 2.42–2.69 (m, 1H), 2.51 and 2.57 (2×s, 3H), 3.20–3.40 (m, 1H), 3.62–4.04 (m, 5H), 7.88 (d, 1H, J=14.4 Hz), 8.77 (s, 1H), 8.80–9.10 (m, 2H), 14.90 (br. s, 1H).
Anal. Calcd. for $C_{21}H_{23}F_4N_3O_4 \cdot 1.0$ HCl $\cdot 1.0$ H$_2$O: C, 50.86; H, 5.28; N, 8.47 Found: C, 50.51; H, 5.27; N, 8.52.

EXAMPLE 30

3S,1S-1-cyclopropyl-6-fluoro-7
-[3-(1-N-tert-butoxycarbonyl-N-methylaminoethyl)-
1-pyrrolidinyl]-8-trifluoromethyl-1,4-dihydro-4-oxo-
3-quinolinecarboxylic acid From 0.83 g (2.5 mmol) of quinolone D, 0.70 g (3.1 mmol) of pyrrolidine 62, and 0.40 g (4.0 mmol) of triethylamine, there was obtained 0.39 g (26%) of the title compound. Concentration of the filtrate and washings provided additional product (0.36 g, 27% ); mp 196°–197° C.
$[\alpha]_D = 177°$ (C=0.44 CHCl$_3$).
$^1$H-NMR (CDCl$_3$) δ 0.70–0.85 (m, 1H), 0.86–1.02 (m, 1H), 1.18 (d, 3H, J=6.7 Hz), 1.23–1.37 (m, 2H), 1.48 (s, 9H), 1.70–1.91 (m, 1H), 1.93–2.10 (m, 1H), 2.32–2.51 (m, 1H), 2.76 and 2.79 (2×s, 3H), 3.51–4.34 (m, 6H), 7.94 (d, 1H, J=14.6 Hz), 8.79 (s, 1H), 14.70–14.80 (m, 1H).
Anal. Calcd. for $C_{26}H_{31}F_4N_3O_5$: C, 57.67; H, 5.77; N, 7.76 Found: C, 57.78; H, 5.92; N, 7.81.

3S,1S-1-cyclopropyl-6-fluoro-7
-[3-(1-N-methylaminoethyl)-1-pyrrolidinyl]
-8-trifluoromethyl-1,4-dihydro-4-oxo-3-
quinolinecarboxylic acid Using Method B on 0.77 g (1.4 mmol) of the above protected quinolone, there was obtained the title compound (0.66 g); mp 252°–253° C.
$^1$H-NMR (d$_6$-DMSO) δ 0.82–0.94 (m, 1H), 0.95–1.08 (m, 1H), 1.11–1.35 (m, 2H), 1.28 (d, 3H, J=6.7 Hz), 1.72–2.00 (m, 1H), 2.23–2.40 (m, 1H), 2.52–2.70 (m, 1H), 2.62 (s, 3H), 3.25–3.42 (m, 1H), 3.63–4.10 (m, 5H), 7.86 (d, 1H, J=14.4 Hz), 8.78 (s, 1H), 14.02 (br. s, 1H).
Anal. Calcd. for $C_{21}H_{23}F_4N_3O_3 \cdot 1.0$ HCl $\cdot 2$ H$_2$O: C, 49.08; H, 5.49; N, 8.18 Found: C, 48.75; H, 5.60; N, 8.55.

EXAMPLE 31

3R,1R-1-cyclopropyl-6-fluoro-7-[
3-(1-N-tert-butoxycarbonyl-N-methylaminoethyl)-
1-pyrrolidinyl]-1,4-dihydro-4-oxo-3-quinolinecarboxylic
acid From 0.64 g (2.4 mmol) of quinolone B, 0.71 g (3.1 mmol) of pyrrolidine 61, and 0.35 g (3.5 mmol) of triethylamine, there was obtained 0.99 g (87%) of the title compound; mp 233°–234° C.
$[\alpha]_D = -65°$ (c=0.20, chloroform).
$^1$H-NMR (CDCl$_3$) δ 1.13–1.22 (m, 5H), 1.27–1.37 (m, 2H), 1.49 (s, 9H), 1.75–1.94 (m, 1H), 1.96–2.14 (m, 1H), 2.39–2.56 (m, 1H), 2.77 and 2.81 (2×s, 3H), 3.32–3.43

(m, 1H), 3.45–3.82 (m, 4H), 3.97–4.30 (m, 1H), 6.81 (d, 1H, J=7.4 Hz), 7.79 (d, 1H, J=14.1 Hz), 8.57 (s, 1H), 15.28–15.39 (m, 1H).
Anal. Calcd. for $C_{25}H_{32}FN_3O_5$: C, 63.41; H, 6.81; N, 8.87; F, 4.01. Found: C, 63.30; H, 6.86; N, 9.03; F, 4.10.

3R,1R-1-cyclopropyl-6-fluoro-7
-[3-(1-N-methylaminoethyl)-1-pyrrolidinyl]
-1,4-dihydro-4-oxo-3-quinolinecarboxylic acid Using Method B on 1.15 g (2.4 mmol) of the above protected quinolone, there was obtained the title compound (0.35 g). Concentration of the mother liquor provided additional product (0.57 g); mp >280° C.
$[\alpha]_D$=–64° (C=1.04, 1N NaOH).
$^1$H-NMR (TFA) δ 1.30–1.48 (m, 2H), 1.55–1.80 (m, 5H), 2.03–2.27 (m, 1H), 2.52–2.70 (m, 1H), 2.86–3.16 (m, 4H), 3.57–4.38 (m, 6H), 7.20–7.53 (m, 2H), 8.13 (d, 1H, J=13.4 Hz), 9.18 (s, 1H), 11.51–11.69 (m, 1H).
Anal. Calcd. for $C_{20}H_{24}FN_3O_3$ . 1.0 HCl . 0.5 $H_2O$: C, 57.35; H, 6.26; N, 10.03 Found: C, 57.04; H, 6.02; N, 9.91.

EXAMPLE 32

3S,1R-1-cyclopropyl-6-fluoro-7
-[3-(1-N-tert-butoxycarbonyl-N-methylaminoethyl-1-pyrrolidinyl]-1,4-dihydro-4-oxo-3-quinolinecarboxylic acid From 0.75 g (2.8 mmol) of quinolone B, 0.75 g (3.3 mmol) of pyrrolidine 63, and 0.44 g (4.3 mmol) of triethylamine, there was obtained 1.01 g (76%) of the title compound; mp 225°–226° C.
$[\alpha]_D$=+93° (c=0.36, chloroform).
$^1$H-NMR (CDCl$_3$) δ 1.11–1.32 (m, 7H), 1.45 and 1.48 (2xs, 9H), 1.66–1.87 (m, 1H), 2.06–2.20 (m, 1H), 2.41–2.59 (m, 1H), 2.79 and 2.81 (2xs, 3H), 3.28–3.82 (m, 5H), 3.99–4.32 (m, 1H), 6.77 (d, 1H, J=7.0 Hz), 7.77 (d, 1H, J=14.1 Hz), 8.55 (s, 1H), 15.32–15.38 (m, 1H).
Anal. Calcd. for $C_{25}H_{32}FN_3O_5$ . 0.20 $H_2O$: C, 62.93; H, 6.84; N, 8.81 Found: C, 62.99; H, 6.81; N, 8.59.

3S,1R-1-cyclopropyl-6-fluoro-7
-[3-(1-N-methylaminoethyl-1
-pyrrolidinyl]-1,4-dihydro-4-oxo-3-quinolinecarboxylic acid Using Method C on 1.09 g (2.3 mmol) of the above protected quinolone afforded the title compound (0.83 g); mp >280° C.
$[\alpha]_D$=55° (c=1.03, 1N NaOH).
$^1$H-NMR (d$_6$-DMSO+TFA) δ 1.42–1.51 (m, 2H), 1.53–1.79 (m, 5H), 2.05–2.25 (m, 1H), 2.41–2.54 (m, 1H), 2.80–3.00 (m, 1H), 2.95 (s, 3H), 3.60–3.74 (m, 1H), 3.76–4.29 (m, 5H), 7.38 (d, 1H, J=7.3 Hz), 8.11 (d, 1H, J=14.0 Hz), 8.90 (s, 1H).
Anal. Calcd. for $C_{20}H_{24}FN_3O_3$ . 1.0 HCl . 0.8 $H_2O$: C, 56.62; H, 6.32; N, 9.90; Cl, 8.36 Found: C, 56.92; H, 6.22; N, 9.89; Cl, 8.39.

EXAMPLE 33

3S,1S-1-cyclopropyl-6-fluoro-7
-[3-(1-N-tert-butoxycarbonyl-N-methylaminoethyl-1-pyrrolidinyl]-1,4-dihydro-4-oxo-3-quinolinecarboxylic acid From 0.66 g (2.5 mmol) of quinolone B, 0.70 g (3.1 mmol) of pyrrolidine 62, and 0.40 g (4.0 mmol) of triethylamine, there was obtained 1.08 g (91%) of the title compound; mp 223.5°–224.5° C.
$[\alpha]_D$=69° (c=0.81, chloroform).
$^1$H-NMR (CDCl$_3$) δ 1.12–1.24 (m, 5H), 1.29–1.37 (m, 2H), 1.49 (s, 9H), 1.78–1.93 (m, 1H), 1.97–2.15 (m, 1H), 2.39–2.56 (m, 1H), 2.77 and 2.81 (2xs, 3H), 3.30–3.41 (m, 1H), 3.42–3.80 (m, 4H), 3.96–4.31 (m, 1H), 6.83 (d, 1H, J=7.4 Hz), 7.83 (d, 1H, J=14.1 Hz), 8.60 (s, 1H), 15.30–15.38 (m, 1H).
Anal. Calcd. for $C_{25}H_{32}FN_3O_5$: C, 63.41; H, 6.81; N, 8.87 Found: C, 63.60; H, 7.12; N, 8.92.

3S,1S-1-cyclopropyl-6-fluoro-7
-[3-(1-N-methylaminoethyl)-1-pyrrolidinyl]-1,4-dihydro-4-oxo-3-quinolinecarboxylic acid Using Method B on 1.10 g (2.3 mmol) of the above protected quinolone, there was obtained the title compound (0.61 g). Concentration of the mother liquor provided additional product (0.22 g); mp >280° C.
$[\alpha]_D$=72° (C=0.52, 1N NaOH).
$^1$H-NMR (d$_6$-DMSO+TFA) δ 1.12–1.20 (m, 2H), 1.22–1.38 (m, 2H), 1.30 (d, 3H, J=6.6 Hz), 1.79–1.96 (m, 1H), 2.20–2.37 (m, 1H), 2.50–2.68 (m, 1H), 2.64 (s, 3H), 3.27–3.52 (m, 2H), 3.58–3.85 (m, 4H), 7.11 (d, 1H, J=7.4 Hz), 7.84 (d, 1H, J=14.2 Hz), 8.61 (s, 1H), 15.50 (s, 1H).
Anal. Calcd. for $C_{20}H_{24}FN_3O_3$. 1.0 HCl . 0.4 $H_2O$: C, 57.59; H, 6.23; N, 10.07; Cl, 8.50 Found: C, 57.68; H, 6.10; N, 10.07; Cl, 8.54.

EXAMPLE 34

3S,1R-1-cyclopropyl-5-amino-6,8-difluoro-7-[
3-(1-N-tert-butoxycarbonyl-N-methylaminoethyl)-
1-pyrrolidinyl]-1,4-dihydro-4-oxo-3-quinolinecarboxylic acid From 0.81 g (2.7 mmol) of quinolone L, 0.75 g (3.3 mmol) of pyrrolidine 63, and 0.44 g (4.3 mmol) of triethylamine, there was obtained 0.62 g (45%) of the title compound. Concentration of the filtrate and washings provided additional product (0.50 g, 37%); mp 198°–199° C.
$[\alpha]_D$=+230° (C=0.45, chloroform).
$^1$H-NMR (CDCl$_3$) δ 0.98–1.25 (m, 7H), 1.46 (s, 9H), 1.60–1.75 (m, 1H), 1.98–2.12 (m, 1H), 2.27–2.44 (m, 1H), 2.76 (d, 3H, J=7.1 Hz), 3.48–3.79 (m, 5H), 3.82–4.30 (m, 1H), 6.30–6.45 (m, 2H), 8.57 (s, 1H), 14.92 and 14.95 (2xs, 1H).
Anal. Calcd. for $C_{25}H_{32}F_2N_4O_5$ . 0.4 $H_2O$: C, 58.45; H, 6.44; N, 10.91 Found: C, 58.46; H, 6.17; N, 10.88.

3S,1R-5-amino-1-cyclopropyl-6,8
-difluoro-7-[3-(1-N-methylaminoethyl)-
1-pyrrolidinyl]-1,4-dihydro-4-oxo-3-quinolinecarboxylic acid Using 1.58 g (3.1 mmol) of the above quinolone, hydrolysis of the tert-butoxycarbonyl group with hydrogen chloride in methylene chloride, followed by 6N HCl, provided the title compound (0.14 g) as the hydrochloride salt.
$^1$H-NMR (TFA) δ 1.25–1.55 (m, 4H), 1.57–1.70 (m, 3H), 1.92–2.11 (m, 1H), 2.30–2.51 (m, 1H), 2.70–2.88 (m, 1H), 2.93–3.10 (m, 3H), 3.58–3.72 (m, 1H), 3.80–4.20 (m, 5H), 7.10–7.60 (m, 2H), 9.14 (s, 1H).

EXAMPLE 35

3S,1S-5-amino-1-cyclopropyl- 6,8-difluoro-7-[3-(1
-N-tert-butoxycarbonyl-N-methylaminoethyl)-
1-pyrrolidinyl]
-1,4-dihydro-4-oxo-3-quinolinecarboxylic acid From 0.78 g (2.6 mmol) of quinolone L, 0.71 g (3.1 mmol) of pyrrolidine 62, and 0.51 g (5.0 mmol) of triethylamine, there was obtained 1.06 g (80%) of the title compound. Concentration of the filtrate and washings provided additional product (0.21 g, 16%); mp 207.5°–208–5° C. [α]$_D$=198° (c=0.42, CHCl$_3$).

$^1$H-NMR (CDCl$_3$) δ 0.98–1.25 (m, 7H), 1.48 (s, 9H), 1.62–1.82 (m, 1H), 1.84–2.04 (m, 1H), 2.27–2.41 (m, 1H), 2.76 and 2.79 (2×s, 3H), 3.45–3.60 (m, 1H), 3.61–3.95 (m, 4H), 3.96–4.31 (m, 1H), 6.30–6.48 (m, 2H), 8.58 (s, 1H), 14.90 and 14.93 (2×s, 1H).

Anal. Calcd. for C$_{25}$H$_{32}$F$_2$N$_4$O$_5$: C, 59.28; H, 6.37; N, 11.06; F, 7.50 Found: C, 59.46; H, 6.54; N, 11.08; F, 6.99.

3S,1S-5-amino-1-cyclopropyl-
6,8-difluoro-7-[3-(1-N-methylaminoethyl)-
1-pyrrolidinyl]-1,4-dihydro-4-oxo-3-quinolinecarboxylic
acid Using 0.75 g (1.8 mmol) of the above quinolone, hydrolysis of the tert-butoxycarbonyl group with hydrogen chloride in methylene chloride, followed by 6N HCl, provided the title compound (0.58 g) as the hydrochloride salt; mp >250° C.

$^1$H-NMR (TFA) δ 1.26–1.60 (m, 4H), 1.61 (d, 3H, J=6.2 Hz), 1.96–2.12 (m, 1H), 2.45–2.60 (m, 1H), 2.72–2.89 (m, 1H), 3.04 (s, 3H), 3.53–3.69 (m, 1H), 3.91–4.40 (m, 5H), 7.20–7.40 (m, 1H), 9.16 (s, 1H).

Anal. Calcd. for C$_{20}$H$_{24}$F$_2$N$_4$O$_3$·2.0HCl·0.60H$_2$O: C, 49.01; H, 5.59; N, 11.43. Found: C, 49.09; H, 5.55; N, 1.07.

General Procedure for 8-Methoxy Quinolone Carboxylic Acids

These derivatives were obtained by reaction of the appropriate pyrrolidine side chain (2 eq) with the 7-fluoro-8-methoxy-1,4-dihydro-4-oxo-3-quinolinecarboxylic acid borate ester according to the general procedure, except that no triethylamine was added to the reaction mixture. The resulting ester was subsequently hydrolyzed with triethylamine in 80% aqueous ethanol.

EXAMPLE 36

3R,1S-1-cyclopropyl-6-fluoro-
7-[3-(1-N-tert-butoxycarbonyl-N-methylaminoethyl)-
1-pyrrolidinyl]-8-methoxy-1,4-dihydro-
4-oxo-3-quinolinecarboxylic acid borate ester From 0.90 g (2.6 mmol) of 8-methoxyquinolone borate ester, and 0.65 g (2.6 mmol) of pyrrolidine 60, there was obtained 1.00 g (70%) of the title compound.

$^1$H-NMR (CDCl$_3$) δ 0.80–0.92 (m, 1H), 0.93–1.08 (m, 1H), 1.10–1.29 (m, 5H), 1.46 (s, 9H), 1.61–1.80 (m, 1H), 2.05–2.20 (m, 1H), 2.32–2.49 (m, 1H), 2.75 and 2.78 (2×s, 3H), 3.62 (s, 3H), 3.65–3.81 (m, 2H), 3.82–4.14 (m, 2H), 4.20–4.38 (m, 2H), 7.82 (br. d, 1H, J=13.8 Hz), 8.93 (s, 1H).

3R,1S-1-cyclopropyl-6-fluoro-
7-[3-(1-N-tert-butoxycarbonyl-N-methylaminoethyl)-
1-pyrrolidinyl]-8-methoxy-1,4
-dihydro-4-oxo-3-quinolinecarboxylic acid From 0.80 g (1.5 mmol) of the above borate ester and (3.6 mmol) of triethylamine in 20 mL of 80% aqueous ethanol, there was obtained 0.56 g (74%) of the title compound after recrystallization from dichloromethane/heptane.

$^1$H-NMR (CDCl$_3$) δ 0.80–0.98 (m, 1H), 1.03–1.40 (m, 6H), 1.44 (s, 9H), 1.52–1.88 (m, 1H), 1.98–2.20 (m, 1H), 2.31–2.50 (m, 1H), 2.73 and 2.75 (2×s, 3H), 3.30–3.60 (m, 2H), 3.55 (s, 3H), 3.62–4.40 (m, 4H), 7.80 (br. d, 1H), 8.74 (s, 1H), 15.02–15.10 (m, 1H).

3R,1S-1-cyclopropyl-6-fluoro-7
-[3-(1-N-methylaminoethyl)-1-pyrrolidinyl]
-8-methoxy-1,4-dihydro-4-oxo-3-quinolinecarboxylic
acid Using Method A on 0.75 g (1.5 mmol) of the above protected quinolone, there was obtained the title compound (0.40 g) as a yellow solid; mp 166°–167° C.

[α]$_D$=–105° (c=1.08, methanol).

$^1$H-NMR (d$_6$-DMSO+CD$_3$OD) δ 0.87–0.99 (m, 1H), 1.01–1.27 (m, 3H), 1.32 (d, 3H, J=6.0 Hz), 1.70–1.90 (m, 1H), 2.08–2.11 (m, 1H), 2.49–2.73 (m, 4H), 3.48–3.69 (m, 3H), 3.57 (s, 3H), 3.71–3.82 (m, 2H), 4.08–4.20 (m, 1H), 7.65 (d, 1H, J=13.8 Hz), 8.66 (s, 1H), 9.09–9.29 (m, 1H), 9.31–9.55 (m, 1H), 15.10–15.20 (br. s, 1H).

Anal. Calcd. for C$_{21}$H$_{26}$FN$_3$O$_4$ · 1.0 HCl · 1.4 H$_2$O: C, 54.23; H, 6.46; N, 9.03: Cl, 7.62 Found: C, 54.04; H, 6.30; N, 8.99; Cl, 8.11.

EXAMPLE 37

3R,1R-1-cyclopropyl-6-fluoro-7
-[3-(1-N-tert-butoxycarbonyl-N-methylaminoethyl)-
1-pyrrolidinyl]-8-methoxy-1,4-dihydro-4-oxo-3-
quinolinecarboxylic acid borate ester From 0.90 g (2.6 mmol) of 8-methoxyquinolone borate ester, and 1.16 g (5.1 mmol) of pyrrolidine 61, there was obtained 1.41 g (98%) of the title compound after recrystallization from dichloromethane/ether.

$^1$H-NMR (CDCl$_3$) δ 0.98–1.08 (m, 1H), 1.12–1.30 (m, 6H), 1.48 (s, 9H), 1.70–1.87 (m, 1H), 1.92–2.13 (m, 1H), 2.32–2.52 (m, 1H), 2.79 and 2.82 (2×s, 3H), 3.55–4.20 (m, 6H), 3.64 (s, 3H), 7.77 (d, 1H, J=13.7 Hz), 8.90 (s, 1H).

Anal. Calcd. for C$_{26}$H$_{33}$BF$_3$N$_3$O$_6$: C, 56.64; H, 6.03; N, 7.62 Found: C, 56.68; H, 6.16; N, 7.55.

3R,1R-1-cyclopropyl-6-fluoro-
7-[3-(1-N-tert-butoxycarbonyl-N-methylaminoethyl)-
1-pyrrolidinyl]-8
-methoxy-1,4-dihydro-4-oxo-3-quinolinecarboxylic
acid From 1.35 g (2.5 mmol) of borate ester and 2.50 g (25 mmol) of triethylamine in 60 mL of 80% aqueous ethanol, there was obtained 0.63 g (50%) of the title compound after recrystallization from dichloromethane/hexane. Concentration of the mother liquor provided additional product (0.50 g, 40%); mp 140°14 145° C.

[α]$_D$=–116° (c=1.06, chloroform).

$^1$H-NMR (CDCl$_3$) δ 0.85–0.97 (m, 1H), 1.02–1.30 (m, 3H), 1.18 (d, 3H, J=6.6 Hz), 1.49 (s, 9H), 1.65–1.88 (m, 1H), 1.91–2.10 (m, 1H), 2.29–2.43 (m, 1H), 2.78 and 2.81 (2×s, 3H), 3.45–3.65 (m, 3H), 3.57 (s, 3H), 3.72–3.83 (m, 1H), 3.96–4.36 (m, 2H), 7.76 (d, 1H, J=13.8 Hz), 8.77 (s, 1H), 14.95–15.20 (m, 1H).

Anal. Calcd. for C$_{26}$H$_{34}$FN$_3$O$_6$ · 1.6 H$_2$O: C, 58.66; H, 7.04; N, 7.89 Found: C, 58.62; H, 7.02; N, 8.09.

3R,1R-1-cyclopropyl-6-fluoro-7
-[3-(1-N-methylaminoethyl-1-pyrrolidinyl]
-8-methoxy-1,4-dihydro-4-oxo-3-quinolinecarboxylic
acid Using Method A on 1.20 g (2.4 mmol) of the above protected quinolone, there was obtained the title compound (0.46 g); mp 212°–213° C. (dec.).

[α]$_D$=–165° (C=1.01, 1N NaOH).

$^1$H-NMR (d$_6$-DMSO) δ 0.86–1.25 (m, 4H), 1.27 (d, 3H, J=6.5 Hz), 1.71–1.92 (m, 1H), 2.20–2.33 (m, 1H), 2.47–2.62 (m, 1H), 2.57 (s, 3H), 3.50–3.65 (m, 3H), 3.57 (s, 3H), 3.70–3.80 (m, 2H), 4.10–4.19 (m, 1H), 7.66 (d, 1H, J=13.9 Hz), 8.66 (s, 1H), 8.90–9.20 (m, 2H), 15.00–15.15 (m, 1H).

Anal. Calcd. for C$_{21}$H$_{26}$FN$_3$O$_4$ . 1.0 HCl.2.0 H$_2$O: C, 53.00; H, 6.57; N, 8.83; Cl, 7.45 Found: C, 52.69; H, 6.47; N, 8.72; Cl, 7.44.

EXAMPLE 38

3S,1R-1-cyclopropyl-6-fluoro-7-[3-(1-N-tert-butoxycarbonyl-N-methylaminoethyl)-1-pyrrolidinyl]-8-methoxy-1,4-dihydro-4-oxo-3-quinolinecarboxylic acid borate ester From 0.86 g (2.5 mmol) of 8-methoxyquinolone borate ester, and 1.14 g (5.0 mmol) of pyrrolidine 63, there was obtained 1.34 g (97%) of the title compound after recrystallization from dichloromethane/ether; mp 185°–186° C. [α]$_D$=+87° (c=0.56, chloroform).
$^1$H-NMR (CDCl$_3$) δ 0.94–1.07 (m, 1H), 1.16–1.29 (m, 2H), 1.24 (d, 3H, J=6.8 Hz), 1.31–1.50 (m, 1H), 1.47 (s, 9H), 1.60–1.82 (m, 1H), 2.06–2.10 (m, 1H), 2.32–2.51 (m, 1H), 2.75 and 2.78 (2×s, 3H), 3.43–3.85 (m, 3H), 3.62 (s, 3H), 3.87–4.38 (m, 1H), 7.82 (br. d, 1H, J=13.8 Hz), 8.92 (s, 1H).

Anal. Calcd. for C$_{26}$H$_{33}$BF$_3$N$_3$O$_6$: C, 56.64; H, 6.03; N, 7.62 Found: C, 56.61; H, 6.00; N, 7.28.

3S,1R-1-cyclopropyl-6-fluoro-7-[3-(1-N-t-butoxycarbonyl-N-methylaminoethyl)-1-pyrrolidinyl]-8-methoxy-1,4-dihydro-4-oxo-3-quinolinecarboxylic acid From 1.35 g (2.5 mmol) of borate ester and 2.50 g (25 mmol) of triethylamine in 50 mL of 80% aqueous ethanol, there was obtained 1.17 g (93%) of the title compound.
$^1$H-NMR (CDCl$_3$) δ 0.82–0.95 (m, 1H), 1.01–1.12 (m, 2H), 1.17–1.29 (m, 4H), 1.46 (s, 9H), 1.60–1.77 (m, 1H), 2.02–2.16 (m, 1H), 2.29–2.48 (m, 1H), 2.74 and 2.77 (2×s, 3H), 3.38–3.70 (m, 3H), 3.56 (s, 3H), 3.79–3.90 (m, 1H), 3.91–4.33 (m, 2H), 7.78 (d, 1H, J=13.9 Hz), 8.77 (s, 1H).

3S,1R-1-cyclopropyl-6-fluoro-7-[3-(1-N-methylaminoethyl)-1-pyrrolidinyl]-8-methoxy-1,4-dihydro-4-oxo-3-quinolinecarboxylic acid Using Method A on 1.10 g (2.2 mmol) of the above protected quinolone, there was obtained the title compound (0.57 g). Concentration of the mother liquor provided additional product (0.22 g); mp 190°–195° C.
$^1$H-NMR (d$_6$-DMSO) δ 1.06–1.23 (m, 4H), 1.31 (d, 3H, J=6.3 Hz), 1.69–1.87 (m, 1H), 2.04–2.10 (m, 1H), 2.48–2.64 (m, 1H), 2.55 (s, 3H), 3.00–3.12 (m, 1H), 3.45–3.65 (m, 2H), 3.57 (s, 3H), 3.66–3.80 (m, 2H), 4.08–4.19 (m, 1H), 7.66 (d, 1H, J=13.8 Hz), 8.66 (s, 1H), 8.91–9.10 (m, 1H), 9.13–9.31 (m, 1H), 15.10–15.20 (m, 1H).

Anal. Calcd. for C$_{21}$H$_{26}$FN$_3$O$_4$ . 1.0 HCl . 2.0 H$_2$O C, 53.00; H, 6.57; N, 8.83 Found: C, 52.76; H, 6.43; N, 8.71.

EXAMPLE 39

3S,1S-1-cyclopropyl-6-fluoro-7-[3-(1-N-tert-butoxycarbonyl-N-methylaminoethyl)-1-pyrrolidinyl]-8-methoxy-1,4-dihydro-4-oxo-3-quinolinecarboxylic acid borate ester From 0.86 g (2.5 mmol) of 8-methoxyquinolone borate ester, and 1.15 g (5.0 mmol) of pyrrolidine 62, there was obtained 1.04 g (75%) of the title compound after recrystallization from dichloromethane/ether; mp 189°–190° C. [α]$_D$=105° (c=0.34, chloroform).
$^1$H-NMR (CDCl$_3$) δ 0.98–1.06 (m, 1H), 1.10–1.32 (m, 6H), 1.49 (s, 9H), 1.72–1.90 (m, 1H), 1.93–2.14 (m, 1H), 2.30–2.48 (m, 1H), 2.78 and 2.82 (2×s, 3H), 3.56–4.37 (m, 6H), 3.62 (s, 3H), 7.85 (d, 1H, J=13.7 Hz), 8.94 (s, 1H).

Anal. Calcd. for C$_{26}$H$_{33}$BF$_3$N$_3$O$_6$ . 0.5 H$_2$O: C, 55.73; H, 6.12; N, 7.50 Found: C, 55.61; H, 6.24; N, 7.49.

3S,1S-1-cyclopropyl-6-fluoro-7-[3-(1-N-tert-butoxycarbonyl-N-methylaminoethyl)-1-pyrrolidinyl]-8-methoxy-1,4-dihydro-4-oxo-3-quinolinecarboxylic acid From 1.00 g (1.8 mmol) of borate ester and 2.50 g (25 mmol) of triethylamine in 50 mL of 80% aqueous ethanol, there was obtained 0.85 g (93%) of the title compound.
$^1$H-NMR (CDCl$_3$) δ 0.85–0.95 (m, 1H), 1.03–1.30 (m, 3H), 1.18 (d, 3H, J=6.8 Hz), 1.49 (s, 9H), 1.68–1.89 (m, 1H), 1.91–2.10 (m, 1H), 2.28–2.44 (m, 1H), 2.77 and 2.81 (2×s, 3H), 3.45–3.64 (m, 3H), 3.57 (s, 3H), 3.70–3.87 (m, 1H), 3.94–4.08 (m, 1H), 4.16–4.36 (m, 1H), 7.77 (d, 1H, J=13.8 Hz), 8.77 (s, 1H).

3S,1S-1-cyclopropyl-6-fluoro-7-[3-(1-N-methylaminoethyl)-1-pyrrolidinyl]-8-methoxy-1,4-dihydro-4-oxo-3-quinolinecarboxylic acid Using Method A on 1.24 g (2.5 mmol) of the above protected quinolone, there was obtained the title compound (0.18 g). Concentration of the mother liquor provided additional product (0.03 g); mp 173°–174° C. (dec).
$^1$H-NMR (d$_6$-DMSO+TFA) δ 0.85–1.25 (m, 4H), 1.26 (d, 3H, J=6.2 Hz), 1.72–1.90 (m, 1H), 2.15–2.31 (m, 1H), 2.42–2.60 (m, 1H), 2.63 (s, 3H), 3.25–3.43 (m, 1H), 3.45–3.68 (m, 6H), 3.70–3.88 (m, 1H), 4.09–4.20 (m, 1H), 7.64 (d, 1H, J=13.8 Hz), 8.52–8.80 (m, 2H), 12.10–12.60 (m, 1H).

EXAMPLE 40

3R,1S-1-cyclopropyl-6-fluoro-7-[3-(1-N-methylaminoethyl)-1-pyrrolidinyl]-1,4-dihydro-4-oxo-3-quinolinecarboxylic acid This compound was prepared by reacting a suspension of the quinolone B (0.80 g, 3.0 mmol) and triethylamine (0.33 g, 3.3 mmol) in acetonitrile (15 mL) with the unprotected side chain 64 (0.42 g, 3.3 mmol) according to the general coupling procedure. The title compound (0.60 g) was obtained. Concentration of the filtrate and washings provided additional product (0.43 g); mp 229°–230° C.
$^1$H-NMR (TFA) δ 1.35–1.42 (m, 2H), 1.55–1.70 (m, 2H), 1.64 (d, 3H, J=6.4 Hz), 2.05–2.19 (m, 1H), 2.41–2.58 (m, 1H), 2.82–3.18 (m, 1H), 3.04 (br. s, 3H), 3.59–3.77 (m, 1H), 3.81–4.06 (m, 4H), 4.32–4.42 (m, 1H), 7.10–7.40

(m, 1H), 7.35 (d, 1H, J=6.8 Hz), 8.13 (d, 1H, J=13.5 Hz), 9.18 (s, 1H), 11.63 (br. s, 1H).

Anal. Calcd. for $C_{20}H_{24}FN_3O_3 \cdot 2.0$ HF $\cdot 0.5$ $H_2O$: C, 56.86; H, 6.44; N, 9.95 Found: C, 56.68; H, 6.11; N, 9.98.

EXAMPLE 41

3R,1R-5-amino-1-cyclopropyl-6,8-difluoro-7-[3-(1-N-methylaminoethyl)-1-pyrrolidinyl]-1,4dihydro-4-oxo-3-quinoline carboxylic acid This compound was prepared by reacting a suspension of the quinolone L (1.19 g, 4.0 mmol) and triethylamine (0.71 g, 5.5 mmol) in acetonitrile (50 mL) with the unprotected side chain 65 (0.70 g, 5.5 mmol) according to the general coupling procedure. The title compound (1.62 g) was obtained; mp 198°–199° C.

$^1$H-NMR (TFA) δ 1.25–1.70 (m, 4H), 1.61 (d, 3H, J=6.6 Hz), 1.93–2.10 (m, 1H), 2.43–2.60 (m, 1H), 2.70–2.88 (m, 1H), 3.06 and 3.07 (2×s, 3H), 3.53–3.70 (m, 1H), 3.85–4.00 (m, 1H), 4.01–4.40 (m, 4H), 7.05–7.35 (m, 1H), 9.14 (s, 1H).

Anal. Calcd. for $C_{20}H_{24}F_2N_4O_3 \cdot 1.5$ $H_2O$: C, 55.42; H, 6.28; N, 12.93 Found: C, 55.70; H, 6.14; N, 12.86.

EXAMPLE 42

3R,1S-5-amino-1-cyclopropyl-6,8-difluoro-7-[3-(1-N-methylaminoethyl)-1-pyrrolidinyl]-1,4-dihydro-4-oxo-3-quinoline carboxylic acid This compound was prepared by reacting a suspension of the quinolone L (0.89 g, 3.0 mmol) and triethylamine (0.46 g, 4.5 mmol) in acetonitrile (30 mL) with the unprotected side chain 64 (0.57 g, 4.4 mmol) according to the general coupling procedure. The title compound (0.59 g) was obtained;

$[α]_D$=–210° (c=0.46, 1N NaOH).

$^1$H-NMR (TFA) δ 1.22–1.39 (m, 2H), 1.40–1.55 (m, 2H), 1.64 (d, 3H, J=6.6 Hz), 1.85–2.07 (m, 1H), 2.35–2.50 (m, 1H), 2.68–2.86 (m, 1H), 3.01 and 3.03 (2×s, 3H), 3.55–3.70 (m, 1H), 3.96–4.20 (m, 5H), 7.03–7.42 (m, 1H), 9.13 (s, 1H), 11.58 (s, 1H).

Anal. Calcd. for $C_{20}H_{24}F_2N_4O_3 \cdot 1.5$ HF $\cdot 0.7$ $H_2O$ C, 53.50; H, 6.04; N, 12.48; F, 14.81 Found: C, 53.56; H, 5.77; N, 12.51; F, 14.96.

EXAMPLE 43

3R,1S-7-[3-(1-aminoethyl)-1-pyrrolidinyl]-1-(2,4-difluorophenyl)-6-fluoro-1,4-dihydro-4-oxo-1,8-napthyridine-3-carboxylic acid A mixture of 7-chloro-1-(2,4-difluorophenyl)-6-fluoro-1,4-dihydro-4-oxo-1,8-napthyridine-3-carboxylic acid G (0.05 g, 1.52 mmol), pyrrolidine 20 (0.32 g, 1.52 mmol), Et$_3$N (1 mL, 7.18 mmol) in CH$_3$CN (20 mL) was refluxed for 18 hours. The solution was cooled and concentrated. The residue was dissolved in CH$_2$Cl$_2$ (50 mL), cooled to 0° C. and treated with gaseous HCl. The reaction was allowed to stir at room temperature for 18 hours and then concentrated. The residue was suspended in H$_2$O (10 mL) and 1N NaOH was added until the pH of the solution was 12. The mixture was filtered and the filtrate acidified with HCl to pH 7.1. The resulting solid was filtered, washed with water and dried to provide the title compound in a yield of 74%; mp 140°–145° C.

EXAMPLE 44

3R,1S-7-[3-(1-aminoethyl)-1-pyrrolidinyl]-1-cyclopropyl-6-fluoro-1,4-dihydro-8-methoxy-4-oxo-3-quinolinecarboxylic acid A solution of 0.53 g (1.55 mmol) of 1-cyclopropyl-6,7-difluoro-1,4-dihydro-8-methoxy-4-oxo-3 -quinolinecarboxylic acid-borondifluoride complex, 0.40 (1.87 mmol) of pyrrolidine 20, 0.60 g (4.6 mmol) of diisopropylethylamine, and 25 mL of acetonitrile was stirred for 3 days at room temperature. The solution was concentrated to an orange oil which was dissolved in 95% ethanol (20 mL) and treated with 5 mL of triethylamine. The solution was heated at reflux for 2 hours, then cooled to room temperature and concentrated. The solid that was obtained was chromatographed (silica gel, 230–400 mesh), eluting with CHCl$_3$/MeOH (9/1), to give 0.69 g of 3R,1S-7-[3-(1-t-butoxycarbonylaminoethyl)- 1-pyrrolidinyl]-1-cyclopropyl-6-fluoro-1,4-dihydro-8-methoxy-4-oxo-3-quinolinecarboxylic acid as a foam, mp 145°–147° C.

The above compound (0.69 g, 1.4 mmol) was dissolved in 30 mL of chloroform, cooled to 5° C., and treated with a steady stream of gaseous HCl for 15 minutes. The solution was allowed to warm to room temperature and concentrated in vacuo. The residue was triturated with 2-propanol:ethyl acetate (1:10), and the solids were filtered, washed with ether, and dried to give 0.54 g of the title compound as the hydrochloride salt; mp 236°–238° C.

Anal. Calcd. for $C_{20}H_{24}FN_3O_4 \cdot 1.25$ HCl$\cdot$H$_2$O: C, 50.04; H, 6.35; N, 8.75; Cl, 9.23. Found: C, 50.09; H, 5.97; N, 8.82; Cl, 9.44. HPLC: 99.5%

$^1$H-NMR (TFA) δ 9.41 (s, 1H), 8.18 (d, 1H), 4.55 (m, 1H), 4.32 (m, 2H), 4.14 (m, 2H), 3.93 (bs, 4H), 2.57 (m, 1H), 3.09 (m, 1H), 2.21 (m, 1H), 1.69 (d, J=5.5 Hz, 3H), 1.61 (m, 1H), 1.50 (m, 1H), 1.33 (m, 1H), 1.21 (m, 1H).

EXAMPLE 45

3R,1R-7-[3-(1-aminoethyl)-1-pyrrolidinyl]-1-cyclopropyl-6-fluoro-1,4-dihydro-8-methoxy-4-oxo-3-quinolinecarboxylic acid The procedure above was used to prepare the title compound (0.54 g) from 0.58 g (1.7 mmol) of 1-cyclopropyl-6,7-difluoro-1,4-dihydro-8-methoxy-4-oxo-3-quinolinecarboxylic acid-borondifluoride complex and 0.43 g (2.0 mmol) of 21. The title compound was isolated as the hydrochloride salt; mp 215°–218° C.

Anal. Calcd. for $C_{20}H_{24}FN_3O_4 \cdot 1.15$ HCl$\cdot 2.1$ H$_2$O: C, 51.20; H, 6.30; N, 8.95; Cl, 8.69. Found: C, 51.20; H, 6.00; N, 8.68; Cl, 8.36.

$^1$H-NMR (DMSO-d$_6$) δ 8.66 (s, 1H), 8.30 (bs, 2H), 7.66 (d, J=14 Hz, 1H), 4.14 (m, 1H), 3.77 (m, 1H), 3.56 (bs, 6H), 3.26 (m, 1H), 2.45 (m, 1H, 2.21 (m, 1H), 1.78 (m, 1H), 1.26 (d, J=6 Hz, 3H), 1.17–0.98 (m, 4H).

EXAMPLE 46

3R,1R-7-[3-(1-aminoethyl)-1-pyrrolidinyl]-1-(2,4-difluorophenyl)-6-fluoro-1,4-dihydro-5-methyl-4-oxo-3-quinolinecarboxylic acid A solution of 0.40 g (1.4 mmol) of 1-(2,4-difluorophenyl)-6,7-difluoro-1,4-dihydro-5 -methyl-4-oxo-3-quinolinecarboxylic acid J, 0.30 g (1.4 mmol) of pyrrolidine 21, 0.36 g (3.6 mmol) of triethylamine, and 20 mL of acetonitrile was heated at reflux for 4 hours. The solution was cooled to 5° C., and the solids were filtered. The product was washed with water and ether, dried, and dissolved in 30 mL of chloroform. This solution was cooled to 5° C. and treated with a steady stream of gaseous HCl for 10 minutes. The mixture was allowed to warm to room temperature, stirred for 18 hours, and filtered. The solids were collected via filtration, washed with ether, and dried in vacuo to give 0.46 g of the title compound as the hydrochloride salt; mp >300° C.

Anal. Calcd. for $C_{23}H_{22}F_3N_3O_3 \cdot HCl \cdot 2.5\ H_2O$: C, 52.42; H, 5.36; N, 7.97; Cl, 6.72. Found: C, 52.24; H, 4.99; N, 7.80; Cl, 6.68. $^1$H-NMR (DMSO-$d_6$) δ 8.67 (s, 1H), 8.15 (bs, 2H), 7.9 (m, 1H), 7.7 (m, 1H), 7.4 (m, 1H), 5.7 (d, 1H), 3.6–3.15 (m, 5H), 2.78 (d, 3H), 2.4 (m, 1H), 2.15 (m, 1H), 1.7 (m, 1H), 1.17 (d, 3H).

EXAMPLE 47

3R,1S-7-[3-(1-aminoethyl)-1-pyrrolidinyl]-1-cyclopropyl-6-fluoro-1,4-dihydro-5-methyl-4-oxo-3-quinolinecarboxylic acid A solution of 0.38 g (1.4 mmol) of 1-cyclopropyl-6,7-difluoro-1,4-dihydro-5-methyl-4-oxo-3 -quinolinecarboxylic acid I, 0.32 g (1.5 mmol) of pyrrolidine 20, 0.42 g (4.2 mmol) of triethylamine, and 25 mL of acetonitrile was heated at reflux for 4 hours, then cooled to 5° C. The mixture was diluted with ether, and the solids were filtered, washed with ether, and dried to give 3R,1S-7-[3-(1-t-butoxycarbonylaminoethyl)-1-pyrrolidinyl]-1-cyclopropyl-6-fluoro-1,4-dihydro-5 -methyl-4-oxo-3-quinolinecarboxylic acid, mp 188°–191° C.

The above compound was dissolved in 30 mL of chloroform, cooled to 5° C., and treated with a steady stream of gaseous HCl for 10 minutes. The solution was allowed to warm to room temperature overnight. Ether was added and the solids were filtered, washed with ether, and dried to give 0.43 g of the title compound as the hydrochloride salt; mp 266°–268° C.

Anal. Calcd. for $C_{20}H_{24}FN_3O_3 \cdot 1.1\ HCl \cdot 1.2\ H_2O$: C, 55.20; H, 6.37; N, 9.66; Cl, 8.96. Found: C, 55.14; H, 6.08; N, 9.54; Cl, 8.91. H$^1$-NMR (DMSO-$d_6$+TFA) δ 8.55 (s, 1H), 7.02 (d, J=7 Hz, 1H), 3.72 (m, 4H), 3.48 (m, 1H), 3.35 (m, 1H), 2.74 (d, 3H), 2.47 (m, 1H), 2.15 (m, 1H), 1.79 (m, 1H), 1.37 (m, 2H), 1.30 (d, J=6.5 Hz, 3H), 1.11 (m, 2H).

EXAMPLE 48

3R,1R-7-[3-(1-aminoethyl)-1-pyrrolidinyl]-1-(2,4-difluorophenyl)-6-fluoro-1,4-dihydro-1,8-naphthyridine-3-carboxylic acid A solution of 0.40 g (1.1 mmol) of 7-chloro-1-(2,4-difluorophenyl)-6-fluoro-1,4-dihydro-1,8-naphthyridine-3-carboxylic acid G, 0.30 g (1.4 mmol) of pyrrolidine 21, 0.36 g (3.6 mmol) of triethylamine, and 15 mL of acetonitrile was heated at reflux for 5 hours. The suspension was cooled to 5° C., and the solids were filtered, washed with water and ether, and dried to give 0.48 g of 3R,1R-7-[3-(1-N-t-butoxycarbonylaminoethyl)-1 -pyrrolidinyl]-1-(2,4-difluorophenyl)-6-fluoro-1,4 -dihydro-1,8-naphthyridine-3-carboxylic acid.

The above compound was dissolved in 20 mL of chloroform, cooled to 5° C., and treated with a steady stream of gaseous HCl for 10 minutes. The solution was warmed to room temperature and concentrated by half. Ether was added, and the solids that formed were filtered, washed with ether, and dried to give 0.38 g of the title compound as the hydrochloride salt; mp 265°–268° C.

Anal. Calcd. for $C_{21}H_{19}F_3N_4O_3 \cdot 1.1\ HCl \cdot 1.2\ H_2O$: C, 51.04; H, 4.59; N, 11.34; Cl, 7.89. Found: C, 50.93; H, 4.45; N, 11.22; Cl, 7.62. $^1$H-NMR (DMSO-$d_6$) δ 15.16 (bs, 1H), 8.83 (s, 1H), 8.20 (bs, 2H), 8.05 (d, J=12 Hz, 1H), 7.80 (m, 1H), 7.61 (m, 1H), 7.34 (m, 1H), 3.35 (m, 5H), 2.33 (m, 1H), 2.12 (m, 1H), 1.68 (m, 1H), 1.15 (bs, 3H).

EXAMPLE 49

3R,1S-7-[3-(1-aminoethyl)-1-pyrrolidinyl]-1-cyclopropyl-8-ethoxy-6-fluoro-1,4-dihydro-4-oxo-3-quinolinecarboxylic acid A solution of 0.55 g (1.55 mole) of 1-cyclopropyl-8-ethoxy-6,7-difluoro-1,4 -dihydro-4-oxo-3-quinolinecarboxylic acid borondifluoride complex, 0.40 g (1.9 mmol) of pyrrolidine 20, 0.60 g (4.6 mmol) of diisopropylethylamine, and 25 mL of acetonitrile was stirred at room temperature for 3 days. The solution was concentrated to a yellow foam which was dissolved in 20 mL of ethanol, treated with 5 mL of triethylamine, and heated at reflux for 5 hours. The mixture was concentrated to a gold solid which was chromatographed (silica gel, eluting with 90:10 CHCl$_3$: MeOH) to give 0.76 g of 3R,1S-7-[3-(1-N-t-butoxycarbonylaminoethyl)-1 -pyrrolidinyl]-1-cyclopropyl-8-ethoxy-6-fluoro-1,4 -dihydro-4-oxo-3-quinolinecarboxylic acid, mp 161°–163 ° C.

The above compound (0.74 g, 1.5 mmol) was dissolved in 30 mL of chloroform, cooled to 5° C., and treated with a steady stream of gaseous HCl for 10 minutes. The solution was allowed to warm to room temperature and stirred for 90 minutes. The suspension was concentrated, and the residue was triturated with ethyl acetate. The solids were filtered, washed with ethyl acetate, and dried to give 0.56 g of the title compound as the hydrochloride salt; mp 222°–224° C.

Anal. Calcd. for $C_{21}H_{26}FN_3O_4 \cdot 1.25\ HCl \cdot 2.5\ H_2O$: C, 51.05; H, 6.58; N, 8.50; Cl, 8.97. Found: C, 51.14; H, 6.35; N, 8.49; Cl, 8.42. $^1$H-NMR (DMSO-$d_6$) δ 15.15 (s, 1H), 8.67 (s, 1H), 8.22 (bs, 3H), 7.66 (d, J=14.0 Hz, 1H), 4.14 (m, 1H), 3.72 (m, 4H), 3.48 (m, 2H), 3.28 (m, 1H), 2.41 (m, 1H), 2.10 (m, 1H), 1.72 (m, 1H), 1.30 (m, 7H), 1.06 (m, 2H), 0.90 (m, 1H).

EXAMPLE 50

3R,1S-7-[3-(1-N-ethylaminoethyl)-1-pyrrolidinyl]-1-(2,4-difluorophenyl)-6-fluoro-1,4-dihydro-4-oxo-1,8-naphthylidine-3-carboxylic acid A solution of 0.71 g (2.0 mmol) of 7-chloro-1-(2,4 -difluorophenyl)-6-fluoro-1,4-dihydro-4-oxo-1,8 -naphthyridine-3-carboxylic acid G, 0.31 g (2.2 mmol) of pyrrolidine 44, 0.61 g (6.0 mmol) of triethylamine, and 15 mL of acetonitrile was heated at reflux for 3 hours, then cooled to room temperature and concentrated. The residue was dissolved in water which was basified to pH 11 with 10% NaOH, filtered through a fiberglass pad, and neutralized to pH 7.2. The solids that formed were filtered, washed with ether, and dried in vacuo to give 0.65 g of the title compound; mp 136°–138° C.

Anal. Calcd. for $C_{23}H_{23}F_3N_4O_3 \cdot 2H_2O$: C, 55.64; H, 5.48; N, 11.28. Found: C, 55.42; H, 5.22; N, 11.31. $^1$H-NMR (DMSO-d₆) δ 8.78 (s, 1H), 8.00 (d, J=13 Hz, 1H), 7.80 (q, 1H), 7.56 (s, 1H), 7.32 (m, 1H), 4.0–3.3 (m, 4H), 2.61 (m, 1H), 2.39 (m, 2H), 2.02 (m, 2H), 1.55 (m, 1H), 0.98 (m, 6H).

EXAMPLE 51

3R,1R-7-[3-(1-N-ethylaminoethyl)-1-pyrrolidinyl]-1-(2,4-difluorophenyl)-6-fluoro-1,4-dihydro-4-oxo-1,8-naphthyridine-3-carboxylic acid The procedure outlined in Example 50 was used to prepare the title compound (0.71 g) from 0.71 g (2.0 mmol) of 7-chloro-1-(2,4-difluorophenyl)-6-fluoro-1,4-dihydro-4-oxo-1,8-naphthyridine-3-carboxylic acid G, 0.31 g (2.2 mmol) of pyrrolidine 45, and 0.61 g (6.0 mmol) of triethylamine. The title compound was isolated via isoelectric precipitation at pH 7.2, mp 203°–205° C.

EXAMPLE 52

3R,1S-1-cyclopropyl-7-[3-(1-N-ethylaminoethyl)-1-pyrrolidinyl]-6-fluoro-1,4-dihydro-5-methyl-4-oxo-3-quinolinecarboxylic acid A solution of 0.56 g (2.0 mmole) of 1-cyclopropyl-6,7-difluoro-1,4-dihydro-5-methyl-4-oxo-3-quinolinecarboxylic acid I, 0.31 g (2.2 mmol) of pyrrolidine 44, 0.61 g (6.0 mmol) of triethylamine, and 15 mL of acetonitrile was heated at reflux for 4 hours. The solution was cooled and concentrated to an orange solid. The residue was dissolved in water, filtered through a fiberglass pad, acidified to pH 2.0, and lyophilized. The yellow powder was dissolved in concentrated hydrochloric acid and filtered; the filtrate was concentrated to a gold oil which was triturated with 2-propanol:ether (1:1). The solids were filtered, washed with 2-propanol and ether, and dried in vacuo to give 0.41 g of the title compound as the hydrochloride salt; mp >300° C.

Anal. Calcd. for $C_{22}H_{28}FN_3O_3 \cdot 1.4$ HCl$\cdot 1H_2O$: C, 56.16; H, 6.73; N, 8.93; Cl, 10.55. Found: C, 56.19; H, 6.45; N, 8.99; Cl, 10.38. ¹H-NMR (DMSO-d₆) δ 8.55 (s, 1H), 7.06 (d, J=2 Hz, 1H), 3.87 (m, 1H), 3.67 (m, 3H), 3.45 (m, 1H), 3.04 (m, 2H), 2.73 (d, J=3 Hz, 3H), 2.55 (m, 2H), 2.16 (m, 1H), 1.82 (m, 1H), 1.40 (m, 2H), 1.28 (m, 6H), 1.09 (m, 2H).

EXAMPLE 53

3R,1S-5-amino-1-cyclopropyl-7-[3-(1-N-ethylaminoethyl)-1-pyrrolidinyl]-6,8-difluoro-1,4,dihydro-4-oxy-3-quinolinecarboxylic acid A solution of 0.60 g (2.0 mmol) of 5-amino-1-cyclopropyl-6,7,8-trifluoro-1,4-dihydro-4-oxo-3-quinolinecarboxylic acid L, 0.31 g (2.2 mmol) of pyrrolidine 44, 0.61 g (6.0 mmol) of triethylamine, and 20 mL of acetonitrile was heated at reflux for 5 hours. The solution was cooled to room temperature and concentrated. The residue was taken up in water which was basified to pH 11, filtered through a fiberglass pad, and neutralized to pH 7.8. The solids that formed were filtered, washed with water and ether, and dried to give 0.61 g of the title compound; mp 148°–150° C.

Anal. Calcd. for $C_{21}H_{26}F_2N_4O_3 \cdot 0.5H_2O$: C, 58.73; H, 6.34; N, 13.05. Found: C, 58.59; H, 6.41; N, 13.45. ¹H-NMR (DMSO-d₆) δ 8.41 (s, 1H), 7.10 (bs, 2H), 3.95 (m, 1H), 3.66 (m, 3H), 3.33 (m, 1H), 2.67 (m, 1H), 2.48 (m, 2H), 2.00 (m, 2H), 1.58 (m, 1H), 1.04 (m, 10H).

EXAMPLE 54

3R,1S-7-[3-(1-N-ethylaminoethyl)-1-pyrrolidinyl[-1-(2,4-difluorophenyl)-6-fluoro-1,4-dihydro-5-methyl-4-oxo-3-quinolinecarboxylic acid A solution of 0.70 g (2.0 mmol) of 1-(2,4-difluorophenyl)-6,7-difluoro-1,4-dihydro-5-methyl-4-oxo-3-quinolinecarboxylic acid J, 0.31 g (2.2 mmol) of pyrrolidine 44, 0.61 g (6.0 mmol) of triethylamine, and 20 mL of acetonitrile was heated at reflux for 4 hours. The solution was cooled to room temperature and concentrated. The residue was taken up in water which was basified to pH 11.0, filtered through a fiberglass pad, neutralized to pH 7.9, and refrigerated. The solids that formed were filtered, washed with water and ether, and dried in vacuo to give 0.51 g of the title compound; mp 187°–189° C.

Anal. Calcd. for $C_{25}H_{26}F_{23}N_3O_3 \cdot 3.6H_2O$: C, 55.77; H, 6.20; N, 7.80. Found: C, 55.50; H, 6.23; N, 7.72.
¹H-NMR (DMSO-d₆) δ 8.67 (s, 1H), 7.88 (m, 1H), 7.72 (m, 1H), 7.43 (m, 1H), 5.65 (d, J=7.7 Hz, 1H), 3.35 (m, 3H), 3.2 (m, 1H), 2.75 (d, J=3.3 Hz, 3H), 2.63 (m, 1H), 2.43 (m, 2H), 2.1 (m, 1H), 1.90 (m, 1H), 1.57 (m, 1H), 0.98 (m, 6H).

EXAMPLE 55

3R,1S-5-amino-7-[3-(1-N-ethylaminoethyl)-1-pyrrolidinyl]-1-cyclopropyl-6-fluoro-1,4-dihydro-4-oxo-3-quinolinecarboxylic acid A solution of 0.56 g (2.0 mmol) of 5-amino-1-cyclopropyl-6,7-difluoro-1,4-dihydro-4-oxo-3-quinolinecarboxylic acid M, 0.31 g (2.2 mmol) of pyrrolidine 44, 0.61 g (6.0 mmol) of triethylamine, and 20 mL of pyridine was heated at reflux for 24 hours. The solution was cooled to room temperature and concentrated. The residue was dissolved in water, acidified to pH 2.0, filtered through a fiberglass pad, and lyophilized. The solids were suspended in concentrated hydrochloric acid and filtered, and the filtrate was concentrated. The residue was triturated with 2-propanol: ether (1:1); the solids were filtered, washed with chloroform and ether, and dried in vacuo to give 0.68 g of the title compound as the hydrochloride salt; mp >300° C.

Anal. Calcd. for $C_{21}H_{27}FN_4O_3 \cdot 1.8HCl \cdot 1.5H_2O$: C, 50.94; H, 6.47; N, 11.31; Cl, 12.91. Found: C, 50.71; H, 6.19; N, 11.25; Cl, 12.63. ¹H-NMR (DMSO-d6) δ 8.42 (s, 1H), 6.38 (d, J=8 Hz, 1H), 3.83 (m, 1H), 3.65 (m, 2H), 3.51 (m, 2H), 3.33 (m, 1H), 2.99 (m, 2H), 2.62 (m, 1H), 2.13 (m, 1H), 1.81 (m, 1H), 1.30 (m, 8H), 1.04 (m, 2H).

EXAMPLE 56

3R,1S-5-amino-1-cyclopropyl-6-fluoro-1.4-dihydro-8-methoxy-7-[3-(1-methylaminoethyl)-1-pyrrolidinyl]-4-oxo-3-quinolinecarboxylic acid A solution of 0.71 g (2.3 mmol) of 5-amino-1-cyclopropyl-6,7-difluoro-1,4-dihydro-8-methoxy-4-oxo-3-quinolinecarboxylic acid K, 0.80 g (3.0 mmol) of pyrrolidine 60, 0.93 g (9.2 mmol) of triethylamine, 15 mL of acetonitrile, and 15 mL of DMSO was refluxed for 18 hours. The mixture was cooled to room temperature, and the acetonitrile was evaporated in vacuo. The solution was poured into water, and the solids that formed were filtered, washed with water and ether, and dried.

The above compound (1.07 g, 2.1 mmol) was dissolved in 30 mL of chloroform, cooled to 5° C., and treated with a steady stream of gaseous HCl for 5 minutes. The mixture was stirred overnight at room temperature. The solution was then concentrated to a paste which was taken up in a small amount of chloroform, diluted with ethyl acetate, cooled to 5° C., and filtered. The solids were washed with ethyl acetate and dried to give 0.95 g of the title compound as the hydrochloride salt; mp 258°–260° C.

Anal. Calcd. for $C_{21}H_{27}FN_4O_4 \cdot 2HCl \cdot 2H_2O$: C, 47.82; H, 6.31; N, 10.62; Cl, 13.44. Found: C, 47.81; H, 5.99; N, 10.78; Cl, 13.77. $^1$H-NMR (DMSO-$d_6$) δ 8.52 (s, 1H), 4.02 (m, 1H), 3.74 (m, 2H), 3.58 (m, 2H), 3.42 (s, 3H), 3.30 (m, 1H), 2.5 (m, 4H), 2.08 (m, 1H), 1.75 (m, 1H), 1.30 (d, J=6.5 Hz, 3H), 1.14 (m, 1H), 0.96 (m, 2H), 0.76 (m, 1H).

EXAMPLE 57

3R,1S-1-cyclopropyl-8-ethoxy-6-fluoro,1,4-dihydro-7-[3-(1-N-methylaminoethyl)-1-pyrrolidinyl]-4-oxo-3-quinolinecarboxylic acid A solution of 0.35 g (1.0 mmol) of 1-cyclopropyl-8-ethoxy-6,7-difluoro-1,4-dihydro- 4-oxo-3-quinoline-carboxylic acid borondifluoride complex, 0.27 g (1.2 mmol) of pyrrolidine 60, 0.46 g (3.6 mmol) of diisopropylethylamine, and 15 mL of acetonitrile was stirred at room temperature for 18 hours. The solution was concentrated to an oil which was chromatographed (silica gel 230–400 mesh, eluting with 90:10 $CHCl_3$:MeOH). The product that was isolated was dissolved in 20 mL of ethanol, treated with 5 mL of triethylamine, and heated at reflux for 3 hours. The solution was cooled to 5° C. and diluted with ether. The solids were filtered, washed with ether, and dried to give 0.47 g of 3R,1S-7-[3-( 1-N-t-butoxycarbonyl-N-methylaminoethyl)-1-pyrrolidinyl]-1-cyclopropyl-8-ethoxy-6-fluoro- 1,4-dihydro-4-oxo-3-quinolinecarboxylic acid.

$^1$H-NMR (CDCl$_3$) δ 15.0 (br s, 1H), 3.77 (s, 1H), 7.76 (d, J=14 Hz, 1H), 4.25 (m, 1H), 4.00 (m, 1H), 3.80 (m, 2H), 3.63 (m, 3H), 3.40 (m, 1H), 2.75 (d, J=10 Hz, 3H), 2.35 (m, 1H), 2.10 (m, 1H), 1.7 (m, 1H), 1.46 (s, 9H), 1.33 (m, 4H), 1.22 (d, J=6.7 Hz, 3H), 1.05 (m, 2H), 0.85 (m, 1H).

A solution of the above compound in 30 mL of chloroform was cooled to 5° C. and treated with a steady stream of gaseous HCl for 10 minutes. The mixture was warmed to room temperature and concentrated. The residue was triturated with isopropanol: ether 1:10, and the solids were filtered and washed with ether to give 0.37 g of the title compound as the hydrochloride salt; mp 210°14 212° C.

Anal. Calcd. for $C_{22}H_{28}FN_3O_4 \cdot 2HCl \cdot 1.15H_2O$: C, 54.83; H, 6.59; N, 8.72; Cl, 8.83. Found: C, 54.93; H, 6.99; N, 9.09; Cl, 8.90. $^1$H-NMR (DMSO-$d_6$) δ 15.1 (bs, 1H), 9.0 (bs, 1H), 8.67 (s, 1H), 7.66 (d, J=13.8 Hz, 1H), 4.14 (m, 1H), 3.74–3.4 (m, 4H), 3.07 (m, 3H), 2.56 (bs, 3H), 2.12 (m, 1H), 1.75 (m, 1H), 1.28 (m, 4H), 1.20 (m, 4H), 1.17 (m, 2H), 0.90 (m, 1H).

EXAMPLE 58

3R,1S-5-amino-7- [3-( 1-aminoethyl)-1-pyrrolidinyl]-1-cyclopropyl-6,8-difluoro-1,4-dihydro-4-oxo-3-quinolinecarboxylic acid A solution of 0.32 g (1.1 mmol) of 5-amino-1-cyclopropyl-6,7,8-trifluoro-1,4-dihydro-4-oxo-3-quinolinecarboxylic acid L, 0.26 g (1.2 mmol) of pyrrolidine 20, 0.32 g (3.2 mmol) of triethylamine, and 15 mL of acetonitrile was heated at reflux for 6 hours. The suspension was cooled to room temperature and filtered. The solids were washed with water and ether, dried, and then dissolved in 20 mL of chloroform. The solution was cooled in an ice bath and treated with a steady stream of gaseous HCl for 10 minutes. The mixture was allowed to warm to room temperature. The solvent was evaporated and the residue was triturated with 30 mL of ethyl acetate. The solids were filtered, washed with ether, and dried in vacuo to give 0.33 g of the title compound as the hydrochloride salt, mp 251°–254 ° C.

EXAMPLE 59

3R,1S-5-amino-7-[3-(1-aminoethyl)-1-pyrrolidinyl]-1-cyclopropyl-6-fluoro-1,4-dihydro-8-methoxy-4-oxo-3-quinolinecarboxylic acid A solution of 0.34 g (1.1 mmol) of 5-amino-1-cyclopropyl-6,7-difluoro-1,4-dihydro-8-methoxy-4-oxo-3-quinolinecarboxylic acid K, 0.26 g (1.2 mmol) of pyrrolidine 20, 0.32 g (3.2 mmol) of triethylamine, 10 mL of DMSO, and 10 mL of acetonitrile was heated at reflux for 18 hours. The acetonitrile was evaporated in vacuo, and the solution was poured into water and extracted with chloroform. The organic layer was dried and concentrated. The residue was chromatographed (silica gel, 230–400 mesh, eluting with 90:10 $CHCl_3$:MeOH) to give 0.37 g of 5-amino-7-[(3R, 1'S)-3-(1'-N-t-butoxycarbonylaminoethyl)-1-pyrrolidinyl]-1-cyclopropyl-6-fluoro-1,4-dihydro-8-methoxy-4-oxo-3-quinolinecarboxylic acid.

$^1$H-NMR (CDCl$_3$) δ 15.08 (s, 1H), 8.64 (s, 1H), 6.39 (bs, 2H), 4.44 (m, 1H), 3.90–3.70 (m, 3H), 3.64 (m, 3H), 3.43 (s, 3H), 2.19 (m, 1H), 2.03 (m, 1H), 1.69 (m, 1H), 1.45 (s, 9H), 1.23 (d, J=6.8 Hz, 3H), 1.20 (m, 1H), 0.97 (m, 2H), 0.74 (m, 1H).

The above compound was dissolved in 20 mL of chloroform, cooled to 5° C., and treated with gaseous HCl for 10 minutes. The mixture was allowed to warm to room temperature and stirred at that temperature for 3 hours. The solution was concentrated to a paste which was triturated with ethyl acetate and filtered. The solids were washed with ether and dried in vacuo to give 0.27 g of the title compound as the hydrochloride salt; mp 234°–237° C.

$^1$H-NMR (DMSO-$d_6$) δ 8.51 (s, 1H), 8.23 (bs, 2H), 4.04 (m, 1H), 3.70 (m, 2H), 3.58 (m, 2H), 3.42 (s, 3H), 3.25 (m, 1H), 2.40 (m, 1H), 2.10 (m, 1H), 1.70 (m, 1H), 1.30 (d, J=6.5 Hz, 3H), 1.15 (m, 1H), 0.96 (m, 2H), 0.86 (m, 1H).

EXAMPLE 60

3R,1S-7-[3-(1-aminoethyl)-1-pyrrolidinyl]-1-cyclopropyl-6-fluoro-1,4-dihydro-4-oxo-8-trifluoromethyl-3-quinolinecarboxylic acid A solution of 0.36 g (1.1 mmol) of 1-cyclopropyl-6,7-difluoro-1,4-dihydro-4-oxo-8-trifluoromethyl-3-quinolinecarboxylic acid D, 0.25 g (1.2 mmol) of pyrrolidine 20, 0.32 g (3.2 mmol) of triethylamine, and 15 mL of acetonitrile was heated at reflux for 3 hours, then cooled to room temperature and concentrated. The residue was chromatographed (silica gel, 230–400 mesh, eluting with 90:10 $CHCl_3$:MeOH) to give 0.53 g of 3R,1S-7-[3-(1-N-t-butoxycarbonylaminoethyl)-1-pyrrolidinyl]-1-cyclopropyl-6-fluoro-1,4-dihydro-4-oxo-8-trifluoromethyl-3-quinolinecarboxylic acid.

$^1$H-NMR (CDCl$_3$) δ 8.78 (s, 1H), 7.94 (d, J=14.3 Hz, 1H), 4.40 (bd, 1H), 3.98 (m, 2H), 3.76 (m, 4H), 2.30 (m, 1H), 2.10 (m, 1H), 1.75 (m, 1H), 1.45 (bs, 9H), 1.24 (d, J=6.7 Hz, 3H), 1.21 (m, 2H), 1.05 (m, 1H), 0.8 (m, 1H).

The above compound was dissolved in 20 mL of chloroform, cooled to 5° C., and treated with a steady stream of gaseous HCl for 10 minutes. The solution was allowed to warm to room temperature and concentrated by half. The suspension was diluted with ether and filtered; the solids were washed with ether and dried in vacuo to give 0.42 g of the title compound as the hydrochloride salt, mp >300° C.

Anal. Calcd. for $C_{20}H_{21}F_4N_3O_3 \cdot 1.8HCl \cdot 1.3H_2O$: C, 46.51; H, 4.95; N, 8.14; Cl, 12.36. Found: C, 46.48; H, 4.79; N, 8.15; Cl, 12.40. $^1$H-NMR (DMSO-$d_6$) δ 8.76 (s, 1H), 8.32 (bs, 3H), 7.86 (d, J=14.6 Hz, 1H), 3.93 (m, 3H), 3.73 (m, 2H), 3.27 (m, 1H), 2.50 (m, 1H), 2.11 (m, 1H), 1.75 (m, 1H), 1.27 (d, 3H), 1.20 (m, 2H), 1.02 (m, 1H), 0.87 (m, 1H).

EXAMPLE 61

3R,1S-1-cyclopropyl-6-fluoro-7-[3-(1-N-methylaminoethyl)1-pyrrolidinyl]-5-methyl-8-methoxy-1,4-dihydro-4-oxo-3-quinolinecarboxylic acid From 1.0 g (2.8 mmol) of 7-fluoro-5-methyl-8-methoxyquinoline borate ester (from quinolone N), and 0.84 g (3.2 mmol) of pyrrolidine 60, and diisopropylethylamine (11.2 mmol) in acetonitrile was obtained 1.38 g (87%) of the desired product.

$^1$H-NMR (DMSO-$d_6$) δ 0.9–1.28 (m, 10H), 1.38 (s, 9H), 1.60–1.68 (m, 1H), 2.1–2.8 (m, 1H), 2.40–2.58 (m, 1H), 2.60–2.70 (d, 6H), 3.48 (s, 3H), 3.5–4.2 (m, 3H), 4.23–4.38 (m, 1H), 8.9 (s, 1H). M+b 1 566.

From 1.3 g (2.3 mmol) of the borate ester obtained above, 2.6 mmol of triethylamine and 60 mL of 80% ethanol was obtained 0.92 g (78%) of the ester which was purified by chromatography (silica gel, 10% $CH_3OH/CHCl_3$).

$^1$H-NMR (DMSO-$d_6$) δ 0.65–0.99 (m, 3H), 1.05–1.30 (m, 4H), 1.37 (s, 9H), 1.46–1.55 (m, 1H), 1.98–2.10 (m, 1H), 2.37–2.50 (m, 1H), 2.66 (d, 6H), 3.45 (s, 3H), 3.38–3.62 (m, 2H), 3.70–3.90 (m, 1H), 3.9–4.2 (m, 2H), 8.62 (s, 1H), 15.61 (s, 1H).

Anal. Calcd. for $C_{27}H_{36}FN_3O_6 \cdot 0.5H_2O$: C, 61.56; H, 7.08; N, 7.98. Found: C, 61.51; H, 6.80; N, 8.12.

From 0.90 g (1.74 mmol) of the ester above, using Method C and recrystallizing from ethanol, the title compound was obtained (0.51 g, 70%); mp 238°–241° C. (dec).

$^1$H-NMR (TFA) δ 1.02–1.38 (dm, 2H), 1.39–1.76 (m, 2H), 1.68 (d, J=6.57 Hz, 3H), 2.22–2.42 (m, 1H), 2.48–2.70 (m, 1H), 2.94 (s, 3H), 3.05 (s, 3H), 3.18–3.38 (m, 1H), 3.62–3.82 (m, 1H), 3.94 (s, 3H), 4.10–4.61 (m, 5H), 9.46 (s, 1H), 11.6 (s, 1H).

Anal. Calcd. for $C_{22}H_{28}N_3F_1O_4 \cdot HCl$: C, 58.21; H, 6.44; N, 9.26. Found: C, 58.08; H, 6.41; N, 9.39.

EXAMPLE 62

3R,1 S-1-difluorophenyl-6-fluoro-7-[3-(1-N-methylaminoethyl)-1-pyrrolidinyl]-1,4-dihydro-4-oxo-3-quinolinecarboxylic acid From 0.46 g (1.07 mmol) of 1-(2,4-difluorophenyl)-6,7-difluoro-5-methyl-8-methoxy quinoline borate ester (from quinolone N), 0.29 g (1.12 mmol) of pyrrolidine 60, and 4.28 mmol of diisopropylethylamine was obtained the coupled product. The resulting borate ester was carried on as described above to provide 0.17 g (61%) of the N-t-butoxycarbonyl derivative after chromatography (10% $CH_3OH/CHCl_3$).

$^1$H-NMR (CDCl$_3$) δ 1.12–1.70 (m, 3H), 1.42 (d, 3H), 1.59 (s, 9H), 2.69, 2.73 (2d, 3H), 2.81 (d, J=3.19 Hz, 3H), 3.02, 3.14 (28, 3H), 3.20–4.30 (m, 7H), 6.8–7.5 (m, 3H), 8.40–8.45 (m, 1H).

From 0.16 g (0.27 mmol) of the above compound, the protecting group was removed using Method C. After recrystallizing from isopropanol, the title compound was obtained, 0.09 g (70%) as an off-white solid; mp 233°–238° C. (dec).

Anal. Calcd. for $C_{25}H_{26}F_3N_3O_4 \cdot HCl \cdot 0.5H_2O$: C, 56.13; H, 5.28; N, 7.85. Found: C, 56.21; H, 0.18; N, 7.89. $^1$H-NMR (TFA) 6 1.62 (d, J=5.5 Hz, 3H), 2.09 (m, 1H), 2.4 (m, 1H), 2.98 (m, 1H), 2.97 (s, 3H), 3.01 (s, 3H), 3.28, 3.39 (28, 3H), 3.65 (m, 1H), 4.09 (m, 5H), 7.18 (m, 2H), 7.72 (m, 1H), 8.99 (m, 1H), 11.63 (s, 1H).

EXAMPLE 63

3R,1R-1-(2,4-difluorophenyl)-5-methyl-7-[3-(1-N-tert-butoxycarbonyl-N-methylaminoethyl)-1-pyrrolidinyl]-1,4-dihydro-4-oxo-3-quinolinecarboxylic acid From 0.70 g (2.0 mmol) of 1-(2,4-difluorophenyl)-5-methyl-1,4-dihydro-4-oxo-3-quinolinecarboxylic acid, J, 0.57 g (2.5 mmol) of pyrrolidine 61, and 1.03 g (8.0 mmol) of diisopropylethylamine, there was obtained the title compound (0.93 g).

$^1$H-NMR (CDCl$_3$) δ 1.07–1.15 (m, 3H), 1.45 (s, 9H), 1.65–1.79 (m, 1H), 1.82–2.01 (m, 1H), 2.25–2.40 (m, 1H), 2.68–2.73 (m, 3H), 2.80 (d, 3H), 3.11–3.40 (m, 3H), 3.50–3.63 (m, 1H), 3.80–4.20 (2×m, 1H), 5.60 (br d, 1H), 7.07–7.21 (m, 2H), 7.40–7.52 (m, 1H), 8.47 (s, 1H), 15.60–15.72 (m, 1H).

Anal. Calcd. for $C_{29}H_{32}F_3N_3O_5$: C, 62.25; H, 5.76; N, 7.51. Found: C, 61.90; H, 5.66; N, 7.51.

3R,1R-1-(2,4-difluorophenyl)-5-methyl-7-[3-(1-N-methylaminoethyl)-1-pyrrolidinyl]-1,4-dihydro-4-oxo-3-quinolinecarboxylic acid From 0.80 g (1.4 mmol) of 3R,1R-1-(2,4-difluorophenyl)-5-methyl-7-[3-(1-N-tert-butoxycarbonyl-N-methylaminoethyl)-1-pyrrolidinyl]-1,4-dihydro-4-oxo-3-quinolinecarboxylic acid, hydrolysis of the tert-butoxycarbonyl group with trifluoroacetic acid in dichloromethane provided the title compound (0.72 g); mp 140°–143° C.

$^1$H-NMR (DMSO-$d_6$) δ 1.16 (d, 3H, J=6.1 Hz), 1.63–1.78 (m, 1H), 2.02–2.18 (m, 1H), 2.32–2.60 (m, 1H), 2.50 (s, 3H), 2.78 (d, 3H, J=3.1 Hz), 3.14–3.40 (m, 4H), 3.50–3.65 (m, 1H), 5.71 (d, 1H, J=7.9 Hz), 7.37–7.49 (m, 1H), 7.65–7.79 (m, 1H), 7.82–7.95 (m, 1H), 8.20–8.70 (m, 2H), 8.69 (s, 1H).

Anal. Calcd. for $C_{24}H_{24}F_3N_3 O_3 \cdot 1.0CF_3CO_2H \cdot 0.6H_2O$: C, 53.45; H, 4.52; N, 7.19. Found: C, 53.47; H, 4.32; N, 7.45.

EXAMPLE 64

3R,1S-1-(2,4-difluorophenyl)-6-fluoro-1,4-dihydro-7-[3-[1-(methylamino)ethyl]-1-pyrrolidinyl]-4-oxo-1,8-naphthyridine-3-carboxylic acid, monohydrochloride A mixture of 7-chloro-1-(2,4-difluorophenyl)-6-fluoro-1,4-dihydro-4-oxo-1,8-naphthyridine-3-carboxylic acid G (0.50 g, 1.41 mmol), compound 60 (0.38 g, 1.66 mmol), Et$_3$N (1 mL, 7.18 mmol) in CH$_3$CN (20 mL) was heated at reflux for 3 hours. The mixture was cooled and concentrated. The residue was dissolved in CH$_2$Cl$_2$ (50 mL), cooled to 0°

C. and HCl was bubbled into the solution for 2 minutes. The reaction was allowed to warm to room temperature for 18 hours and concentrated. The residue was recrystallized from EtOH/H$_2$O to provide 0.56 g (82%) of the desired product; mp 278°–280° C. (dec). NMR (DMSO-d$_6$) δ 1.21 (d, 3H), 1.66 (m, 1H), 2.01 (m, 1H), 3.22 (m, 2H), 3.34 (s, 3H), 7.34 (t, 1H), 7.59 (t, 1H), 7.82 (q, 1H), 8.06 (d, 1H), 8.81 (s, 1H), 8.98 (bs, 2H).

EXAMPLE 65

3R,1S-7-[3-(1-aminoethyl)-1 -pyrrolidinyl]-1-(2,4 -difluorophenyl)-6-fluoro-1,4-dihydro-5-methyl-4-oxo-3 -quinolinecarboxylic acid, monohydrochloride A mixture of 6,7-difluoro-1-(2,4-difluorophenyl)-1,4-dihydro-5-methyl-4-oxo-3-quinolinecarboxylic acid J (0.41 g, 1.20 mmol), compound 20 (0.36 g, 1.44 mmol), ET$_3$N (1 mL, 7.18 mmol) in CH$_3$CN (25 mL) was heated at reflux for 3 hours. The reaction was worked up as described previously to provide 0.51 g (87%) of the desired product; mp >250° C. NMR (DMSO-d6) δ 1.22 (d, 3H), 1.75 (, 1H), 2.03 (m, 1H), 2.37 (m, 1H), 2.77 (m, 3H), 3.78 (m, 1H), 5.75 (d, 1H), 7.43 (t, 1H), 7.73 (t, 1H), 7.90 (t, 1H), 8.19 (bs, 2H), 8.66 (s, 1H).

EXAMPLE 66

3R,1S-1-(2,4-difluorophenyl)-6-fluoro-1,4-dihydro-5 -methyl-7-[3-(methylamino)ethyl]-1-pyrrolidinyl]-4-oxo-3-quinolinecarboxylic acid, monohydrochloride A mixture of 6,7-difluoro-1-(2,4-difluorophenyl)-1,4-dihydro-5-methyl-4-oxo-3-quinolinecarboxylic acid J (0.50 g, 1.47 mmol), compound 60 (0.38 g, 1.66 mmol), Et$_3$N (1 mL, 7.18 mmol) in CH$_3$CN 920 mL) was heated at reflux for 5 hours. The mixture was then cooled and concentrated. The residue was dissolved in CH$_2$Cl$_2$ (50 mL), cooled to 0° C. and HCl was bubbled into the solution for 2 minutes. The reaction was then allowed to stir at room temperature for 18 hours, and then concentrated. The residue was recrystallized from EtOH/H$_2$O to provide 0.58 g (78%) of the desired product; mp >300° C. (dec.).

NMR (DMSO-d$_6$) δ 1.24 (d, 3H), 1.69 (m, 1H), 2.01 (m, 1H), 2.77 (d, 3H), 3.33 (m, 6H), 3.67 (m, 1H), 5.73 (d, 1H), 7.42 (t, 1H), 7.70 (t, 1H), 7.89 (q, 1H), 8.66 (s, 1H).

EXAMPLE 67

3R,1S-1-cyclopropyl-6-fluoro-1,4-dihydro-5-methyl-7-[3 -[1-(methylamino)ethyl]-1-pyrrolidinyl]-4-oxo-3 -quinolinecarboxylic acid, monohydrochloride A mixture of 1-cyclopropyl-6,7-difluoro-1,4 -dihydro-5-methyl-4-oxo-3-quinolinecarboxylic acid I (0.41 g, 1.47 mmol), compound 60 (0.41 g, 1.55 mmol), Et$_3$N (1 mL, 7.13 mmol) and CH$_3$CN (20 mL) was heated at reflux for 3 hours. Workup was performed as described above to provide 0.49 g (79%) of the desired product; mp >250 ° C.
NMR (DMSO-d$_6$-TFA) δ 1.11 (m, 2H), 1.31 (d, 3H), 1.38 (m, 2H), 1.79 (m, 1H), 2.52 (s, 2H), 2.71 (d, 3H), 3.34 (t, 1H), 3.48 (t, 1H), 3.67 (m, 3H), 3.86 (m, 1H), 7.01 (d, 1H), 8.53 (s, 1H).

EXAMPLE 68

3R,1S-5-amino-1-cyclopropyl-6-fluoro-7-[ 3-[1-(methylamino)ethyl]-1-pyrrolidinyl]-4-oxo-3-quinolinecarboxylic acid, monohydrochloride A mixture of 5-amino-1-cyclopropyl-6,7-difluoro-4 -oxo-3-quinolinecarboxylic acid M (0.40 g, 1.42 mmol), compound 60 (0.42 g, 1.68 mmol), Et$_3$N (1 mL, 7.18 mmol) in pyridine (20 mL) was heated at reflux for 7 hours and then stirred at room temperature for 12 hours. The mixture was concentrated and chromatographed (silica gel, 5% MeOH/CHCl$_3$) to provide 0.60 g of material.
NMR (CDCl$_3$) δ 1.07 (m, 2H), 1.23 (m, 5H), 1.45 (m, 9H), 2.15 (m, 1H), 2.56 (m, 1H), 2.78 (m, 3H), 3.28–3.85 (m, 6H), 6.14 (d, 1H), 6.46 (bs, 2H), 8.52 (s, 1H).

This material was dissolved in CHCl$_2$ (25 mL), cooled to 0° C. and HCl was bubbled in for 2 minutes. The mixture was allowed to warm to room temperature, stirred for 18 hours, and concentrated. The residue was recrystallized from EtOH/H$_2$O to provide 0.28 g (45%) of the desired product; mp >250° C.
NMR (DMSO-d$_6$) δ 1.05 (6 s, 2H), 1.30 (m, 6H), 1.73 (m, 1H), 2.15 (m, 1H), 2.56 (s, 3H), 3.28–3.85 (m, 6H), 6.37 (d, 1H), 7.18 (bs, 1H), 8.41 (s, 1H), 9.11 (bs, 2H).

EXAMPLE 69

3S,1R-1-cyclopropyl-7-[3-[ 1-(dimethylamino)ethyl]-1 -pyrrolidinyl]-6-fluoro-1,4-dihydro-4-oxo-1,8-naphthyridine-3-carboxylic acid The title compound was prepared from naphthyridine A, pyrrolidine 35, and triethylamine using the procedure outlined in Example 50; mp 231°–234° C.

EXAMPLE 70

3S,1S-1-cyclopropyl-7-[3-[1-(dimethylamino.)ethyl]-1 -pyrrolidinyl]-6-fluoro-1,4-dihydro-4-oxo-1,8 -naphthyridine-3-carboxylic acid The title compound was prepared from naphthyridine A, pyrrolidine 34, and triethylamine using the procedure outlined in Example 50; mp 226°–228° C.

EXAMPLE 71

3R,1S-1-cyclopropyl-7-[3-[1-(dimethylamino)ethyl]-1 -pyrrolidinyl]-6-fluoro-1,4-dihydro-4-oxo-1,8 -naphthyridine-3-carboxylic acid The title compound was prepared from naphthyridine A, pyrrolidine 32, and triethylamine using the procedure outlined in Example 50; mp 231°–233° C.

EXAMPLE 72

3R,1R-1-cyclopropyl-7-[3-[1-(dimethylamino)ethyl]-1 -pyrrolidinyl]-6-fluoro-1,4-dihydro-4-oxo-1,8 -naphthyridine-3-carboxylic acid The title compound was prepared from naphthyridine A, pyrrolidine 33, and triethylamine using the procedure outlined in Example 50; mp 228°–230° C.

EXAMPLE 73

3R,1S-1-cyclopropyl-7-[3-[1-(dimethylamino)ethyl]-1-pyrrolidinyl]-6-fluoro-1,4-dihydro-4-oxo-3-quinolinecarboxylic acid The title compound was prepared from quinolone B, pyrrolidine 32, and triethylamine as outlined in Example 14; mp 273°–275° C.

EXAMPLE 74

3R,1R-1-cyclopropyl-7-[3-[1-(dimethylamino)ethyl]-1-pyrrolidinyl]-6-fluoro-1,4-dihydro-4-oxo-3-quinolinecarboxylic acid The title compound was prepared from quinolone B, pyrrolidine 33, and triethylamine as outlined in Example 14; mp 263°–265° C.

EXAMPLE 75

3S,1R-1-cyclopropyl-7-[3-[1-(dimethylamino)ethyl]-1-pyrrolidinyl]-6-fluoro-1,4-dihydro-4-oxo-3-quinolinecarboxylic acid The title compound was prepared from quinolone B, pyrrolidine 35, and triethylamine as outlined in Example 14; mp 262°–264° C.

EXAMPLE 76

3S,1S-1-cyclopropyl-7-[3-[1-(dimethylamino)ethyl]-1-pyrrolidinyl]-6-fluoro-1,4-dihydro-4-oxo-3-quinolinecarboxylic acid The title compound was prepared from quinolone B, pyrrolidine 34, and triethylamine as outlined in Example 14; mp 271°–274° C.

EXAMPLE 77

3R,1R-1-cyclopropyl-7-[3-[1-(ethylamino)ethyl]-1-pyrrolidinyl]-6-fluoro-1,4-dihydro-4-oxo-1,8-naphthyridine-3-carboxylic acid The title compound was prepared from naphthyridine A, pyrrolidine 45, and triethylamine using the procedure outlined in Example 50.

Anal. Calcd. for $C_{20}H_{25}FN_4O_3 \cdot 0.05$ HF: C, 59.75; H, 6.63; N, 13.94; F, 4.96. Found: C, 59.72; H, 6.75; N, 14.23; F, 5.18.

EXAMPLE 78

3R,1S-1-cyclopropyl-7-[3-[1-(ethylamino)ethyl]-1-pyrrolidinyl]-6-fluoro-1,4-dihydro-4-oxo-1,8-naphthyridine-3-carboxylic acid The title compound was prepared from naphthyridine A, pyrrolidine 44, and triethylamine using the procedure outlined in Example 50.

Anal. Calcd. for $C_{20}H_{25}FN_4O_3 \cdot 0.1$ HF $\cdot 0.4$ $H_2O$: C, 60.41; H, 6.57; N, 14.09; F, 5.26. Found: C, 60.75; H, 6.52; N, 13.61; F, 5.19.

EXAMPLE 79

3S,1R-1-cyclopropyl-7-[3-[1-(ethylamino)ethyl]-1-pyrrolidinyl]-6-fluoro-1,4-dihydro-4-oxo-1,8-naphthyridine-3-carboxylic acid The title compound was prepared from naphthyridine A, pyrrolidine 47, and triethylamine using the procedure outlined in Example 50.

Anal. Calcd. for $C_{20}H_{25}FN_4O_3 \cdot 0.45$ $H_2O$: C, 60.58; H, 6.58; N, 14.13; F, 4.79. Found: C, 60.57; H, 6.47; N, 14.29; F, 5.01.

EXAMPLE 80

3S,1S-1-cyclopropyl-7-[3-[1-(ethylamino)ethyl]-1-pyrrolidinyl]-6-fluoro-1,4-dihydro-4-oxo-1,8-naphthyridine-3-carboxylic acid The title compound was prepared from naphthyridine A, pyrrolidine 46, and triethylamine using the procedure outlined in Example 50.

Anal. Calcd. for $C_{20}H_{25}FN_4O_3 \cdot 0.5$ $H_2O$: C, 60.44; H, 6.59; N, 14.10; F, 4.78. Found: C, 60.83; H, 6.40; N, 14.15; F, 4.86.

We claim:

1. A process for the preparation of the individual stereoisomers of the formula

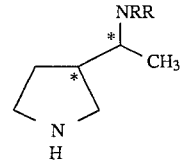

wherein * denotes asymmetric carbon atoms and R is hydrogen or alkyl of 1–3 carbon atoms which comprises:

(a) converting a chitally fixed pyrrolidin-5-one-3-carboxylic acid of the formula

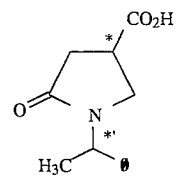

wherein *' is either R or S by known methods to a diastereomeric pair of oximes of the formula

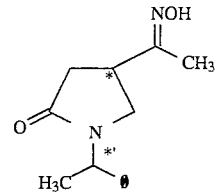

wherein * is an asymmetric carbon atom;

(b) separating the diastereomers by column chromatography;

(c) reducing each diastereomeric oxime by known means to a diastereomeric pair of amines of the formula

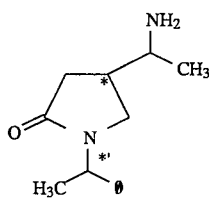

(d) separating each diastereomeric pair of amines into the individual diastereomers by column chromatography;
(e) reducing the 5-pyrrolidinone by known methods and protecting the free amino group with a suitable protecting group by known methods, if desired, and
(f) removing the fixed chiral α-methylbenzyl group by hydrogenolysis, and converting, if desired, by known means the resulting compounds where R is hydrogen to those where R is independently hydrogen or alkyl of 1–3 carbon atoms.

2. A substantially pure individual stereoisomer of the formula

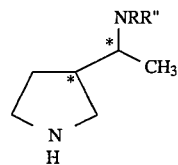

wherein
* denotes asymmetric carbon atoms;
R is hydrogen or alkyl or 1–3 carbon atoms;
R" is alkyl of 1–3 carbon atoms of the 3R,1'S configuration.

3. The stereoisomer of claim 2, wherein R is hydrogen, methyl or ethyl, and R" is methyl or ethyl.

4. The compound of claim 2 which is 3R,1'S-3-(1'-N-methylamino)ethyl)pyrrolidine.

* * * * *

UNITED STATES PATENT AND TRADEMARK OFFICE
CERTIFICATE OF CORRECTION

PATENT NO. : 5,461,165
DATED : Oct. 24, 1995
INVENTOR(S) : Domagala et al.

It is certified that error appears in the above-identified patent and that said Letters Patent is hereby corrected as shown below:

Column 100, line 14 after "alkyl", "or" should read "of".

Signed and Sealed this

Sixth Day of June, 2000

Attest:

Q. TODD DICKINSON

*Attesting Officer*    *Director of Patents and Trademarks*